(12) United States Patent
Kutryk

(10) Patent No.: US 11,129,926 B2
(45) Date of Patent: Sep. 28, 2021

(54) MEDICAL DEVICES COATED WITH POLYDOPAMINE AND ANTIBODIES

(71) Applicant: OrbusNeich Medical PTE. LTD., Singapore (SG)

(72) Inventor: Michael J. B. Kutryk, Toronto (CA)

(73) Assignee: OrbusNeich Medical PTE. LTD., Singapore (SG)

( * ) Notice: Subject to any disclaimer, the term of this patent is extended or adjusted under 35 U.S.C. 154(b) by 358 days.

(21) Appl. No.: 15/953,172

(22) Filed: Apr. 13, 2018

(65) Prior Publication Data
US 2018/0296732 A1 Oct. 18, 2018

Related U.S. Application Data

(60) Provisional application No. 62/645,606, filed on Mar. 20, 2018, provisional application No. 62/485,223, filed on Apr. 13, 2017.

(51) Int. Cl.
| | |
|---|---|
| *A61L 29/08* | (2006.01) |
| *A61L 29/16* | (2006.01) |
| *A61L 15/26* | (2006.01) |
| *A61L 31/10* | (2006.01) |
| *A61L 31/16* | (2006.01) |
| *B01D 71/36* | (2006.01) |

(52) U.S. Cl.
CPC ............ *A61L 29/085* (2013.01); *A61L 15/26* (2013.01); *A61L 29/16* (2013.01); *A61L 31/10* (2013.01); *A61L 31/16* (2013.01); *B01D 71/36* (2013.01); *A61F 2250/0067* (2013.01); *A61F 2310/0097* (2013.01); *A61L 2300/256* (2013.01); *A61L 2300/416* (2013.01); *A61L 2420/06* (2013.01)

(58) Field of Classification Search
CPC ........ A61L 29/085; A61L 15/26; A61L 29/16; A61L 31/10; A61L 31/16; B01D 71/36
See application file for complete search history.

(56) References Cited

U.S. PATENT DOCUMENTS

| | | | |
|---|---|---|---|
| 5,554,119 A * | 9/1996 | Harrison ........... | A61M 16/0481 604/103.01 |
| 7,037,332 B2 * | 5/2006 | Kutryk .................... | A61L 27/44 623/1.48 |
| 8,784,895 B2 | 7/2014 | Messersmith | |
| 9,272,075 B2 | 3/2016 | Antoni | |
| 2002/0049495 A1 | 4/2002 | Kutryk et al. | |
| 2002/0055759 A1 | 5/2002 | Shibuya | |
| 2008/0051868 A1 | 2/2008 | Cottone et al. | |
| 2012/0237605 A1 | 9/2012 | Messersmith et al. | |
| 2014/0221522 A1 | 8/2014 | Antoni et al. | |
| 2016/0081797 A1 * | 3/2016 | Cottone ................. | A61L 27/58 424/426 |
| 2016/0228549 A1 | 8/2016 | Messersmith et al. | |
| 2016/0303287 A1 | 10/2016 | Rajamannan et al. | |
| 2016/0331564 A1 | 11/2016 | Kangas | |
| 2018/0296732 A1 | 10/2018 | Kutryk | |

FOREIGN PATENT DOCUMENTS

| | | |
|---|---|---|
| EP | 0455705 B1 | 5/1997 |
| WO | 2010/006196 A2 | 1/2010 |
| WO | 2011/005258 A1 | 1/2011 |
| WO | 2016025922 | 2/2016 |

OTHER PUBLICATIONS

Gessner et al "Protein rejecting properties of PEG-grafted nanoparticles: Influence of PEG-chain length and surface density evaluated by two-dimensional electrophoresis and bicinchoninic acid (BCA)-proteinassay". 2006. Pharmazie 61, 4, pp. 293-297 (Year: 2006).*
Iqbal et al. "Contemporary stents and current recommendations". 2013. British Medical Bulletin, 106 pp. 193-211 (Year: 2013).*
Lansky et al. "Treatment of Coronary Artery Perforations Complicating Percutaneous Coronary Intervention With a Polytetrafluoroethylene-Covered Stent Graft" 2006. Am J Cardiol. 98:370-374. (Year: 2006).*
Lee et al. "Mussel-Inspired Surface Chemistry for Multifunctional Coatings"; Science Oct. 19, 2007: vol. 318, Issue 5849, pp. 426-430. (Year: 2007).*
Li et al. "Lysine-PEG-modified polyurethane as a fibrinolytic surface: Effect of PEG chain length on protein interactions, platelet interactions and clot lysis"; Acta Biomaterialia 5 (2009) 1864-1871. (Year: 2009).*
Liu and Yu. "Oriented immobilization of proteins on solid supports for use in biosensors and biochips: a review"; Microchim Acta (2016) 183:1-19. (Year: 2016).*
Kawai, F. "Biodegradation of Polyethers (Polyethylene Glycol, Polypropylene Glycol, Polytetramethylene glycol, and others)"; 2005 [online][accessed on Apr. 15, 2021 from onlinelibrary.wiley.com/doi/full/10.1002/3527600035.bpol9012] (Year: 2005).*
Belanger and Marois. "Hemocompatibility, Biocompatibility, Inflammatory and in Vivo Studies of Primary Reference Materials Low-Density Polyethylene and Polydimethylsiloxane: A Review"; J Biomed Mater Res. 2001;58(5):467-77 (Year: 2001).*
International Search Report and Written Opinion dated Jul. 10, 2018 corresponding to International Patent Application No. PCT/US2018/27597, 16 pages.
Dreyer et al.: "Perspectives on poly(dopamine)": Chem. Sci., 2013, 4, 3796-3802.
"Polydopamine/ PTFE Composite Coating for Large-Scale Journal Bearings in Next Generation Electric Machines.": DOE/EE-1585; Mar. 2018.
Ryu et al.: "Mussel-Inspired Polydopamine Coating as a Universal Route to Hydroxyapatite Crystallization." Advanced Functional Materials, vol. 20, Issue 13, Jul. 9, 2010, pp. 2132-2139. https://onlinelibrary.wiley.com/doi/abs/10.1002/adfm.200902347.

(Continued)

*Primary Examiner* — Joanne Hama
*Assistant Examiner* — Scott T. Humbarger
(74) *Attorney, Agent, or Firm* — Leason Ellis LLP

(57) ABSTRACT

The present disclosure provides for a medical device or a substrate coated with polydopamine which is further linked to ligands such as antibodies and/or antibody fragments. The polydopamine coating and the ligands may be linked through a linker such as an organic polymer.

9 Claims, 24 Drawing Sheets

(56) References Cited

OTHER PUBLICATIONS

Talon et al.: "Polydopamine Functionalization: A Smart and Efficient Way to Improve Host Responses to e-PTFE Implants." Frontiers in Chemistry, Jul. 2019, vol. 7, Article 482.
Beckford et al.: "The effects of polydopamine coated Cu nanoparticles on the tribological properties of polydopamine/ PTFE coatings." Tribology International, 103, (2016), 87-94.
Cheng et al.: "Conversion of Functional Group on PTFE Surface by Argon Plasma Pre-treatment and Polydopamine Coating." IOP Conf. Series: Materials Science and Engineering, 381, (2018), 012039.
Shen et al.: "Convenient surface functionalization of whole-Teflon chips with polydopamine coating." BIOMICROFLUIDICS 9, 044111, (2015).
Orishchin et al.: "Rapid Deposition of Uniform Polydopamine Coatings on Nanoparticle Surfaces with Controllable Thickness." Langmuir 2017, 33, 6046-6053.
Terrill, Helen C. Ms., "Optimization of Polydopamine Coatings" (2015). Honors Research Projects. 84. http://ideaexchange.uakron.edu/honors_research_projects/84.
Zhu et al., Polydopamine Nanoparticles for Combined Chemo- and Photothermal Cancer Therapy, Nanomaterials, 2017, 7, 160, p. 1-9.
Luo et al., Improved immobilization of biomolecules to quinone-rich polydopamine for efficient surface functionalization, Colloids and Surfaces B: Biointerfaces, 2013, 106: 66-73. Abstract.
Wan et al., Direct immobilisation of antibodies on a bioinspired architecture as a sensing platform. Biosens Bioelectron. 2011; 26(5):2595-600. Abstract.
Zelasko-Leon et al., MUC1-Targeted Cancer Cell Photothermal Ablation Using Bioinspired Gold Nanorods, PLoS ONE 2015, 10(7): e0128756.
Chen et al., Immobilization of serum albumin and peptide aptamer for EPC on polydopamine coated titanium surface for enhanced in-situ self-endothelialization, Mater Sci Eng C Mater Biol Appl. 2016; 60:219-229. Abstract.
Jeong et al. Polydopamine coatings enhance biointegration of a model polymeric implant, Soft Matter, 2011, 7, 8305-8312. Abstract.
Musilkova et al., Cell adhesion and growth enabled by biomimetic oligopeptide modification of a polydopamine-poly (ethylene oxide) protein repulsive surface, J Mater Sci: Mater Med (2015) 26:253.
Yang et al., Mussel-Inspired Coating of Polydopamine Directs Endothelial and Smooth Muscle Cell Fate for Re-endothelialization of Vascular Devices, Adv. Healthcare Mater. 2012, 1, 548-559.
Lynge et al. "Polydopamine—a nature-inspired polymer coating for biomedical science." Nanoscale. 2011; 3:4916-28.
Lee et al., Mussel-inspired surface chemistry for multifunctional coatings. Science. 2007; 318:426-30.
Wei et al. "Oxidant-induced dopamine polymerization for multifunctional coatings": Polym. Chem., 2010, 1, 1430-1433.
Kang et al. Langmuir, "Bioinspired Single Bacterial Cell Force Spectroscopy": 2009, 25, 9656-9659. Abstract.
Dreyer et al.: "Elucidating the Structure of Poly(dopamine)": Langmuir, 2012, 28, 6428-6435.
Sobocinski et al.: "Mussel Inspired Coating of a Biocompatible Cyclodextrin Based Polymer onto CoCr Vascular Stents", ACS Appl. Mater. Interfaces 2014, 6, 3575-3586.
Lee et al. "Polydopamine-mediated immobilization of multiple bioactive molecules for the development of functional vascular graft materials." Biomaterials. 2012, 33(33): 8343-52. Abstract.
Zeng et al. "A novel PEG coating immobilized onto capillary through polydopamine coating for separation of proteins in CE." Electrophoresis. 2010; 31:3334-41. Abstract.
Kausaite-Minkstimiene et al. "Comparative study of random and oriented antibody immobilization techniques on the binding capacity of immunosensor." Anal. Chem. 2010; 82:6401-08.
Rotmans et al. "In vivo cell seeding with anti-CD34 antibodies successfully accelerates endothelialization but stimulates intimal hyperplasia in porcine arteriovenous expanded polytetrafluoroethylene grafts." Circulation. 2005;112:12-18.
Mrówczyñski et al. "Biological effects of anti-CD34-coated ePTFE vascular graft. Early in vivo experimental results." Kardiochirurgia i Torakochirurgia Polska 2014; 11:182-90.
Lin et al. "In situ endothelialization of intravascular stents coated with an anti-CD34 antibody functionalized heparin-collagen multilayer" Biomaterials. 2010; 31:4017-25.
Yuan et al. "Site-directed immobilization of antibodies onto blood contacting grafts for enhanced endothelial cell adhesion and proliferation." Soft Matter. 2011; 7:7207-16. Abstract.
Kang et al. "Improving immunobinding using oriented immobilization of an oxidized antibody." J. Chromatogr. A. 2007;1161:9-14. Abstract.
Wei et al. "Improving the blood compatibility of material surfaces via biomolecule-immobilized mussel-inspired coatings." J. Biomed. Mater. Res. A. 2011; 96:38-45.
Luo et al., In vitro investigation of enhanced hemocompatibility and endothelial cell proliferation associated with quinone-rich polydopamine coating. ACS Appl. Mater. Interfaces. 2013;5:1704-14. Abstract.
Chen et al: "The effect of anti-CD34 antibody orientation control on endothelial progenitor cell capturing cardiovascular devices", Journal of Bioactive and Compatible Polymers. 2016, 31(6), S. 583-599.

* cited by examiner

Figure 1
A
Non-oriented antibody immobilization using dextran coating
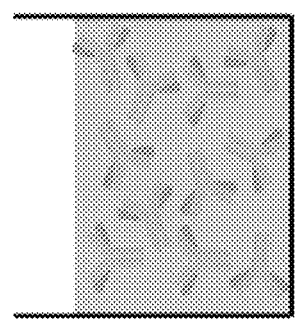
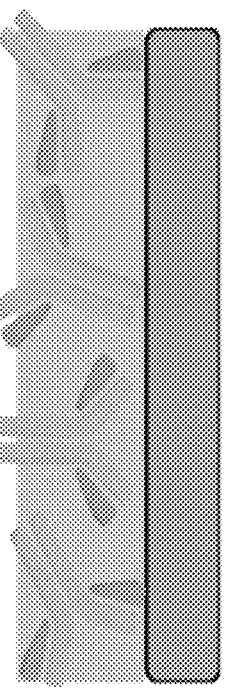
B
Non-oriented antibody immobilization using amine coating
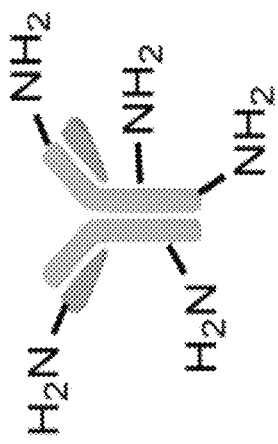
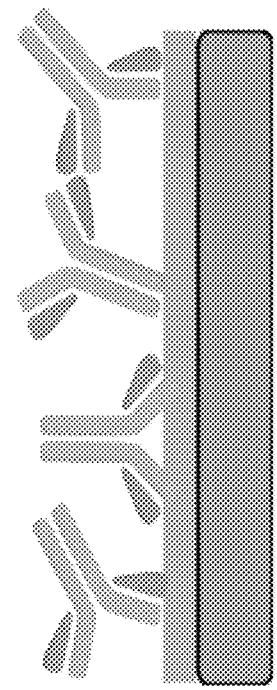

Step 1: Polydopamine deposit–basis of universal coating

Step 3: Oriented antibody coating

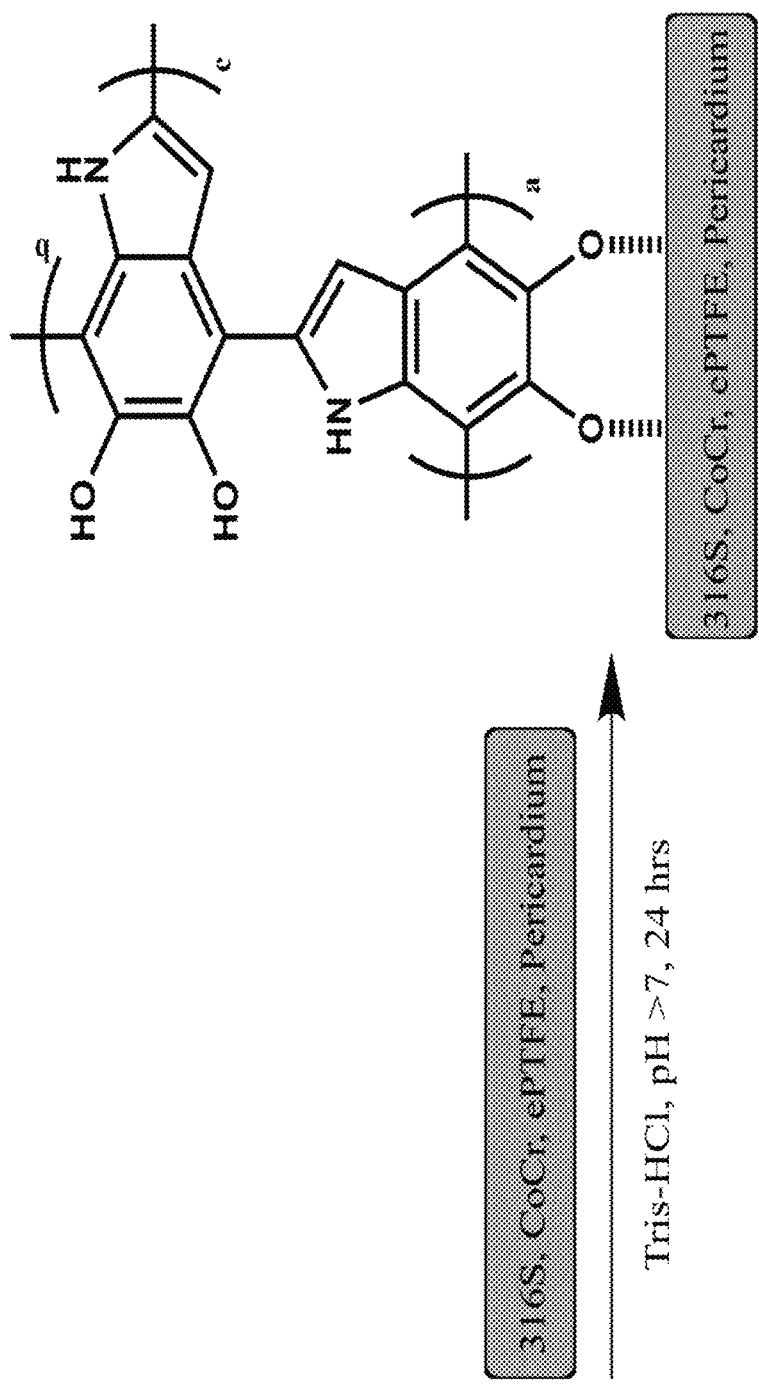
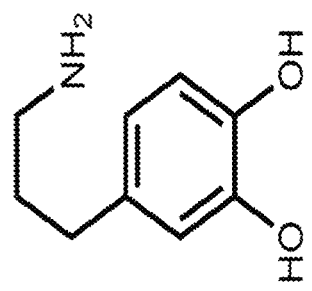
Figure 4B

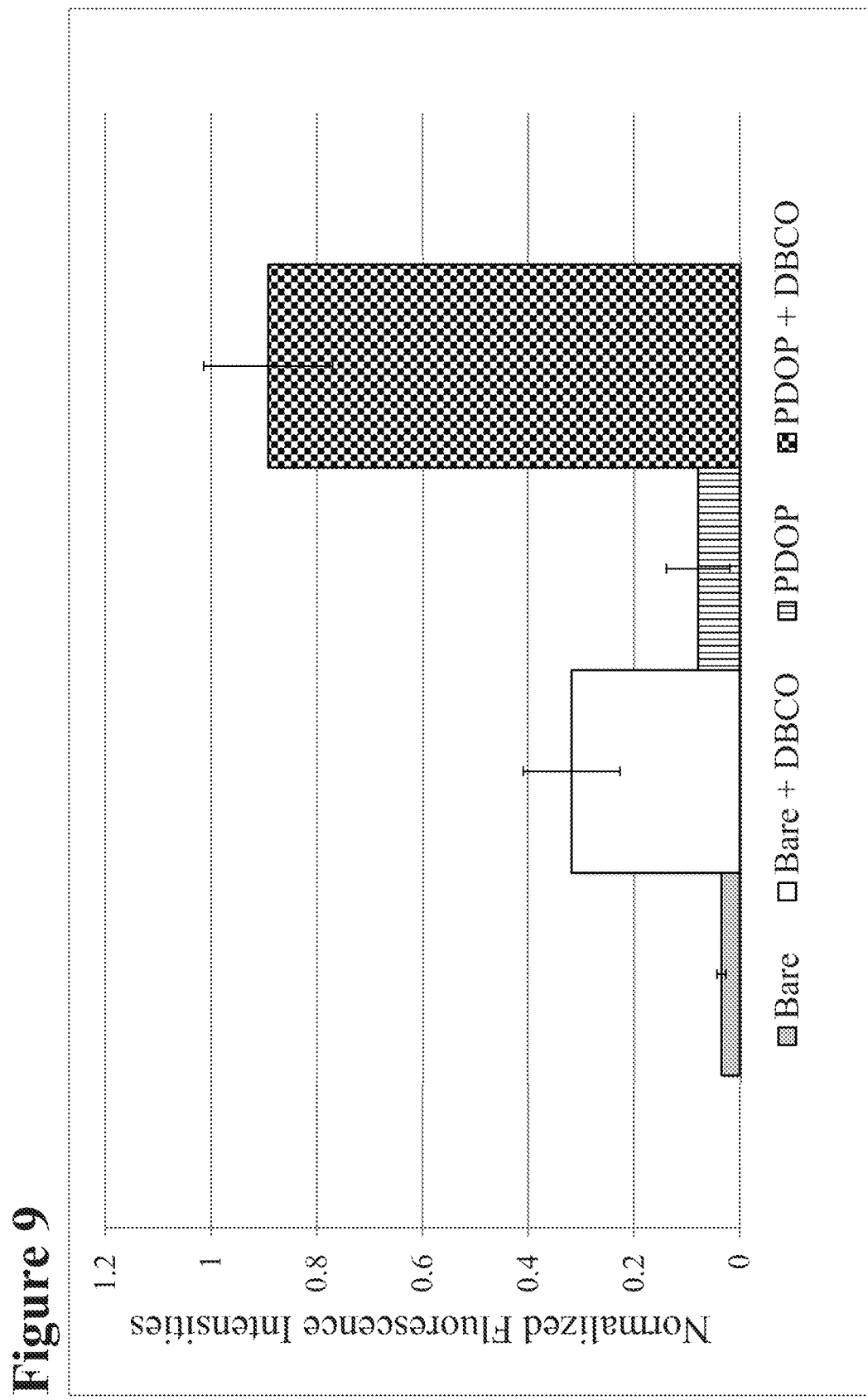

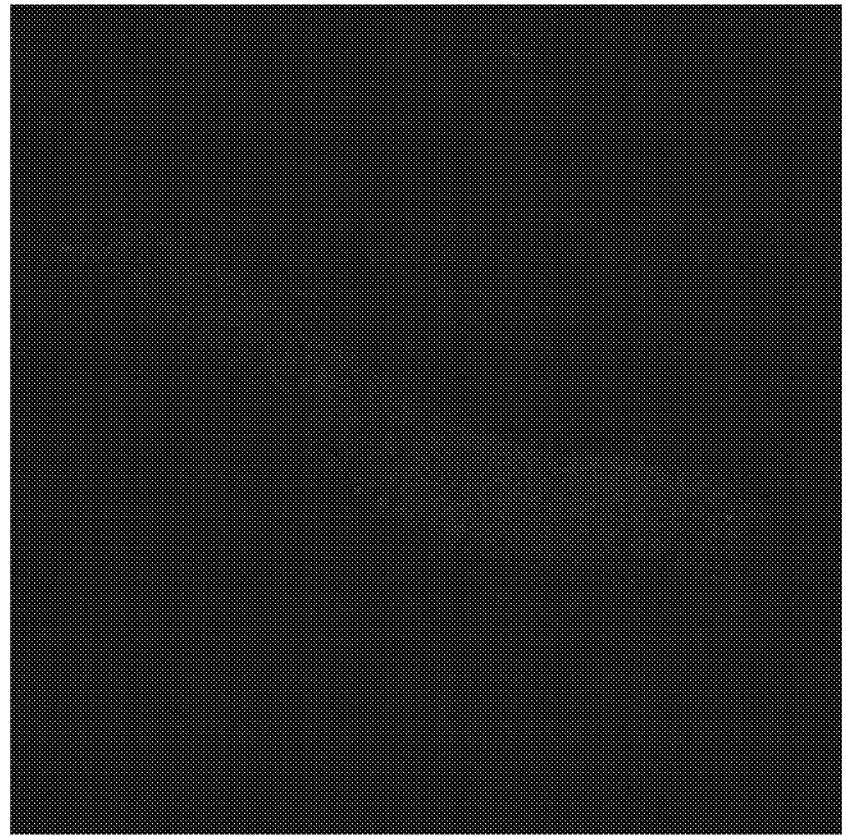
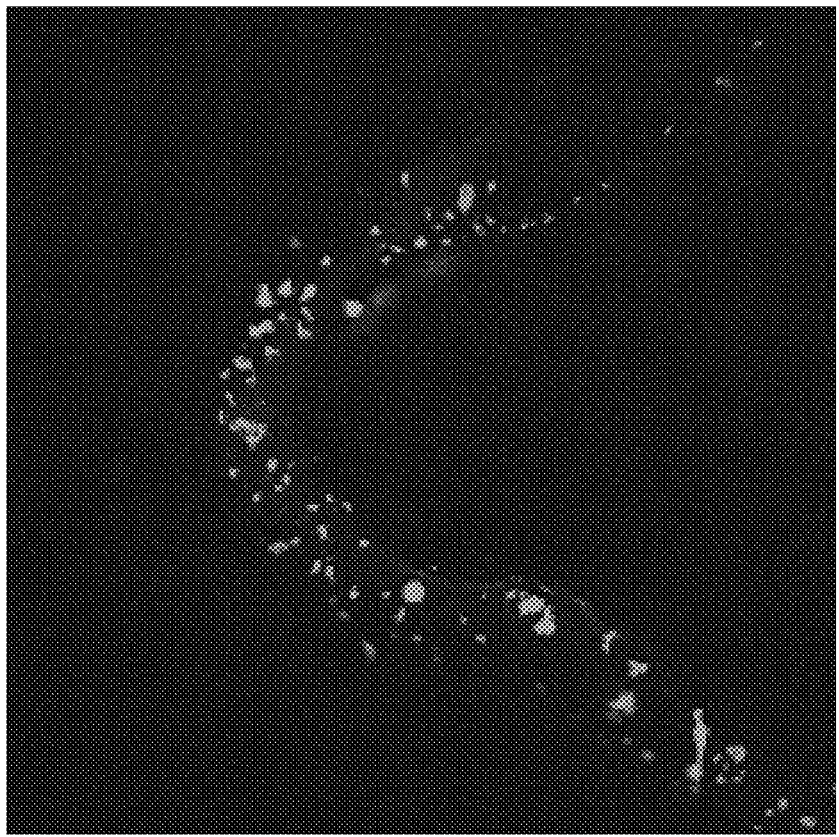
Figure 10

Figure 11
Cobalt chromium discs coated with dopamine-PEG-CD34-antibodies
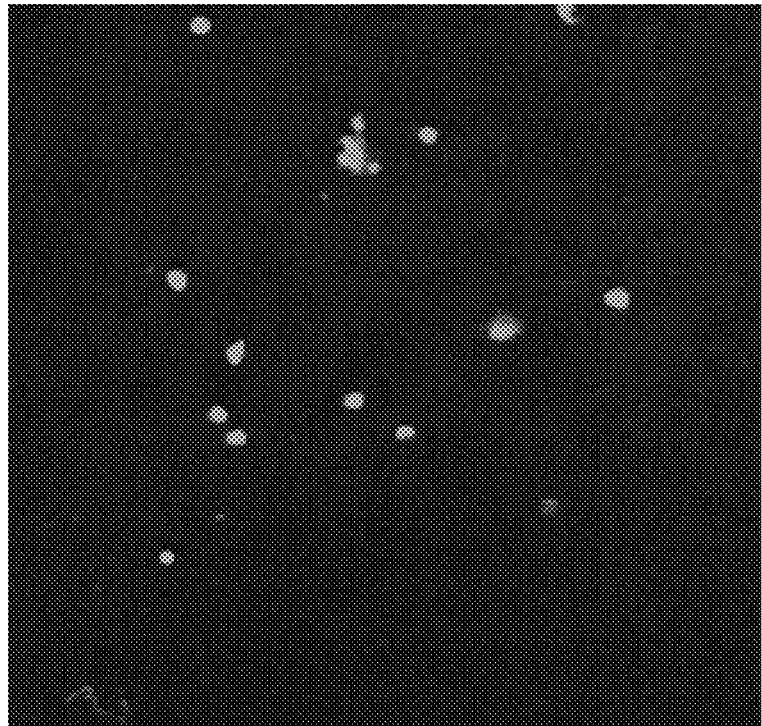
Negative
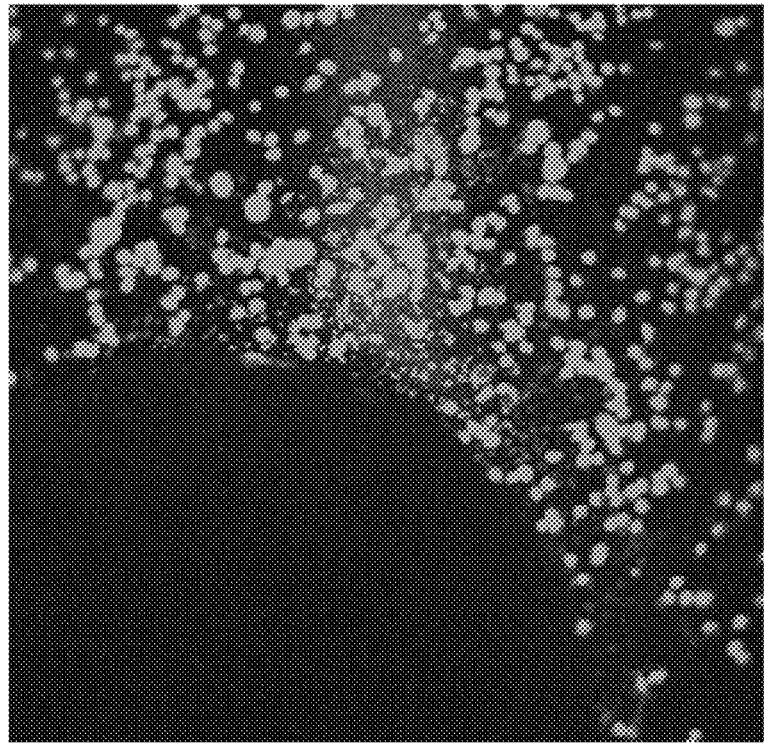
Positive Figure 12
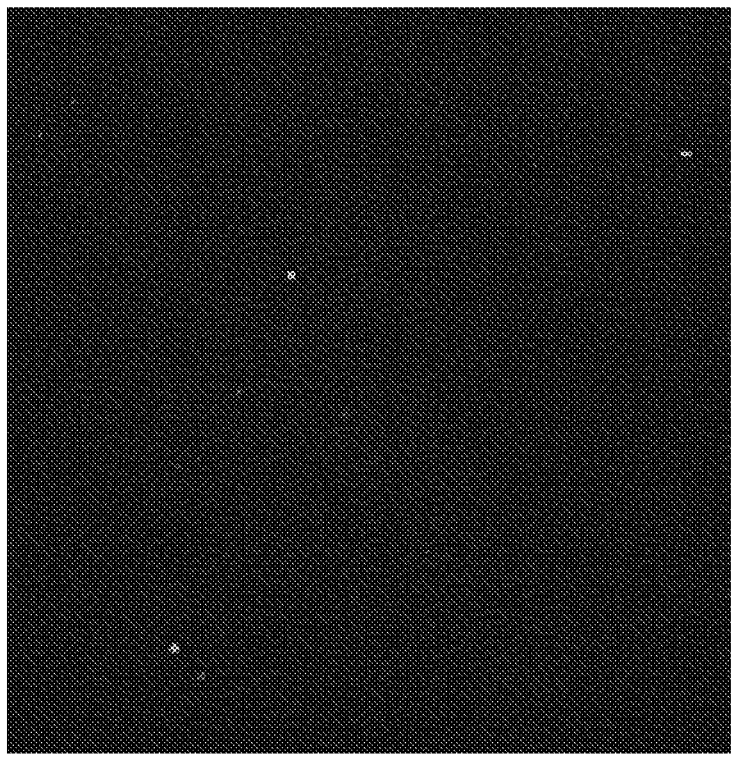
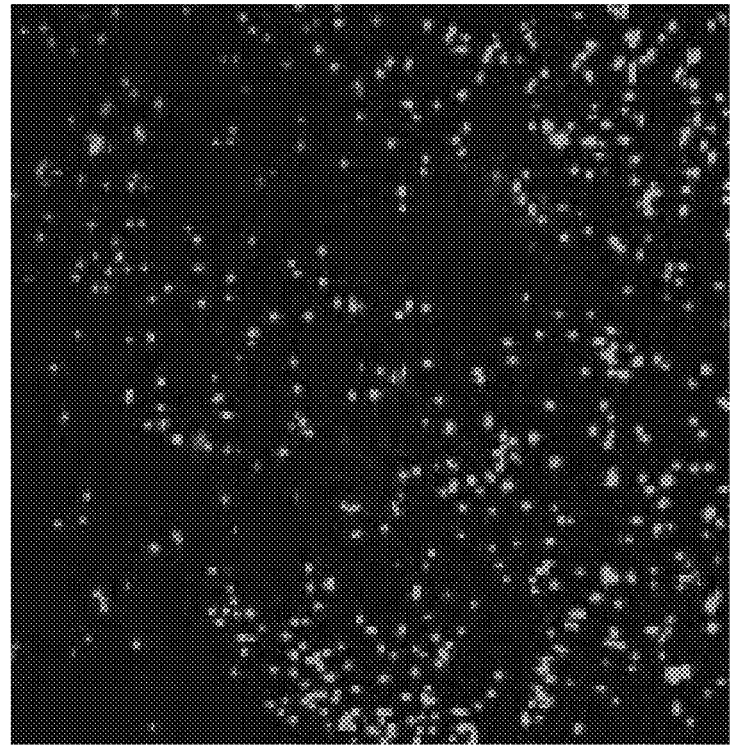

Figure 13
Stability assessment
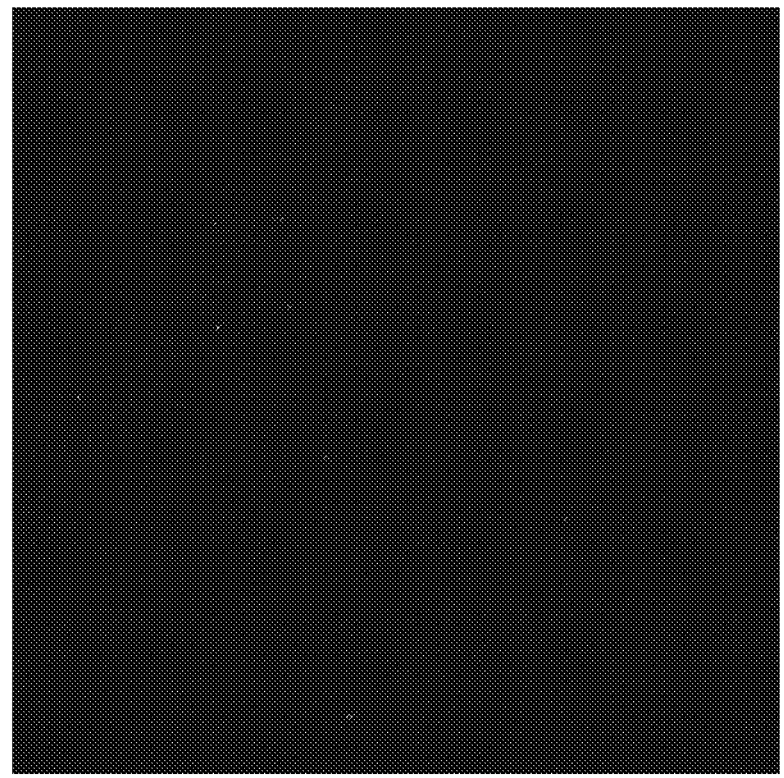
CD34− cells
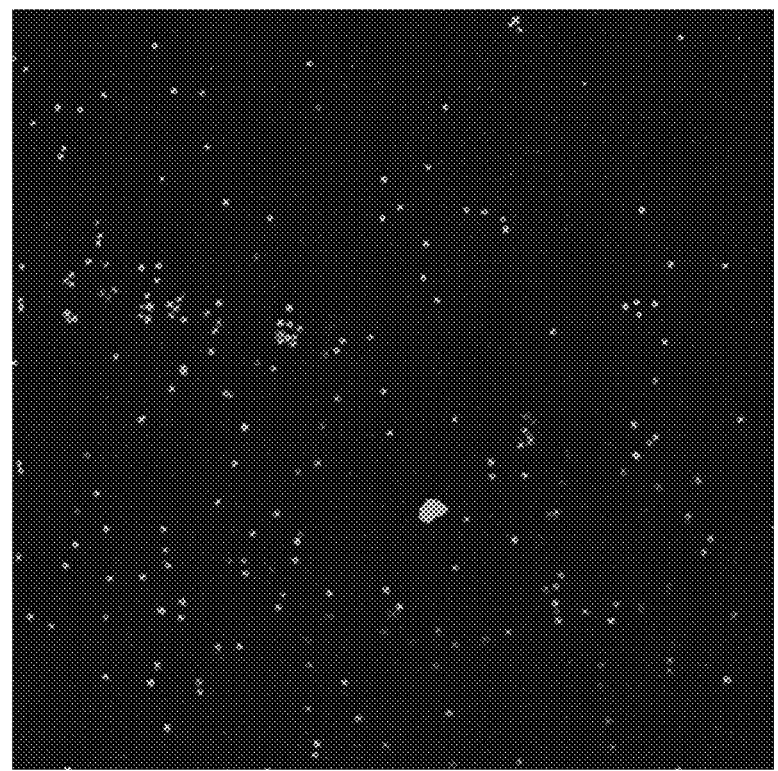
CD34+ cells

MEDICAL DEVICES COATED WITH POLYDOPAMINE AND ANTIBODIES

CROSS REFERENCE TO RELATED APPLICATIONS

This application claims priority to U.S. Provisional Application No. 62/485,223 (filed on Apr. 13, 2017) and U.S. Provisional Application No. 62/645,606 (filed on Mar. 20, 2018), which are incorporated herein by reference in their entirety.

FIELD

The invention relates to medical devices, such as intravascular devices, coated with polydopamine and antibodies.

BACKGROUND OF THE INVENTION

The immobilization of biomolecules is of great interest for both the biological and physical sciences. An active area of study in this field is the development of bioactive coatings for intravascular devices. These devices (coronary stents, vascular grafts, etc.) are used to treat coronary artery disease (CAD) and peripheral arterial disease (PAD), known to cause significant mortality and morbidity[1]. Although advances in treatment such as risk factor modification and the introduction of novel pharmacotherapies have markedly reduced the incidence and improved the outcome of atherosclerotic vascular disease; surgical vascular bypass grafting and percutaneous transluminal coronary angioplasty (PTCA) with endovascular stenting continue to rank amongst the most common procedures performed in North America annually[2]. These revascularization procedures are routinely used, but unfortunately the long-term success of stent implantation is limited by restenosis and late stent thrombosis at the treatment site; while the short- and medium-term success of synthetic grafts used for the treatment of PAD is limited by their thrombogenicity.

Intra-arterial stents are cylindrical meshes made from a wide range of materials (e.g., 316L stainless steel (SS), tantalum, nitinol, cobalt-chromium (CoCr) alloy, platinum-iridium, polymers, etc.). Restenosis, the reduction of luminal gain after stent implantation in a process called intimal hyperplasia, remains one of the most significant problems faced by interventional physicians. Drug-eluting stents, designed to reduce early restenosis through the release of cytotoxic compounds locally into the vessel wall, were found to result in complications such as late thrombosis, and late restenosis. It was soon recognized that drug-eluting stents not only inhibited the proliferation of smooth muscle cells (SMCs) responsible for restenosis but also inhibited the formation of a confluent endothelial cell (EC) layer to cover the stent, a process that is critical for healing.

Expanded polytetrafluoroethylene (ePTFE) has become the most frequently used conduit for arterial reconstruction. The high flow rates of large diameter vascular grafts provide long-term (>10 year) patency rates of 85-95% with only minimal adjunctive pharmacological therapy[3]. However, the successful development of small-diameter artificial vascular prostheses (<5 mm) continues to be a challenge due to the shortened patency caused primarily by the high thrombogenicity of ePTFE. This is further perpetuated by a lack of contact inhibition of ECs at this interface, that can lead to EC hyperplasia[4]. Failure of the synthetic grafts to completely endothelialize in humans results in continued thrombo-inflammatory events on the surface of the graft that ultimately contribute to the development of myointimal hyperplasia, a common cause of failure of arterial reconstructions[5-7]. In fact, less than 50% of small diameter femoral-popliteal grafts remain patent 5 years post-implantation[8].

Failure of complete surface re-endothelialization of prosthetic intravascular material is common in humans, while confluent EC coverage is usual in other mammalian species[9]. The source of endothelial cells established on prosthetic grafts was thought to be from capillary infiltration, or by ingrowth from the edges of the adjacent artery[10]. However, this paradigm has recently been questioned. It has been shown that in high porosity ePTFE grafts implanted in humans, capillary ingrowth rarely extended more than half the distance from the outside of the graft to the lumen[11]. Rather, it has been shown that the principal source of the sparse endothelial cell lining of a prosthetic implant in humans may be from the circulating blood, through a process which has been termed "fallout healing"[12]. Subsequent studies by Shi et al further demonstrated that the fallout ECs are bone marrow derived[13, 14], and are represented in the blood as circulating endothelial progenitor cells (EPCs).

The arterial endothelium is a dynamic organ, maintaining vessel homeostasis by controlling dynamic processes such as its relaxation and contraction as well as fibrinolysis, thrombogenesis, and platelet activation/inhibition. The formation of this active organ can provide favorable biological properties in vessels after stent implantation, and in interposition prosthetic grafts. ECs interrupt SMC proliferation by inhibiting cytokine release and passivate stented surfaces and prosthetic graft material preventing thrombosis[15-17]. The recognition of the importance of a confluent endothelial lining on implanted vascular devices prompted research into the seeding of vascular stents and grafts with ECs as a means to improve their long term patency. Since Herring first introduced EC seeding in 1978, many groups have contributed to the evolution of this technology, all with limited success[18-60]. It is generally agreed that autologous ECs would provide the best source of tissue, however the limited availability of autologous ECs, and the tedious process of seeding and implantation, coupled with the failure to achieve a predictable confluent monolayer of cells on the surface of the prosthesis, has been an overwhelming problem. Moreover, the structure and biochemical environments of venous, arterial, microvascular and macrovascular beds are all unique. Therefore, placement of ECs from one bed into another may result in dysfunctional cell performance. The best approach for the re-endothelialization of a material would be to promote the process of fallout healing by accelerating the attraction of EPCs to the prosthesis[61]. Based on an average EC area of 245 $\mu m^2$, capturing EPCs at a density of 4100 cells/mm$^2$ could provide full coverage of a material surface leading to effective endothelialization of vascular prostheses[62].

We have designed, developed and tested an EPC capture intracoronary stent[63-65]. The stent utilizes a polymeric dextran coating with embedded mouse monoclonal anti-human CD34 antibodies to capture EPCs and enhance the natural endothelialization process. The dextran coating technology has proven effective for CD34+ cell capture. Like our dextran coating, other antibody immobilization strategies for the capture of specific cell types have seen some success. Unfortunately, they too are often specific to a limited range of substrates, suffer from loss of bioactivity, and require labor-intensive chemistry. In this work, we aim to develop a universal method for the immobilization of biologically active molecules that can be effectively applied to a wide range of substrates.

Valves are integral to the normal physiological functioning of the cardiovascular system. For example, natural heart valves ensure unidirectional blood flow from one chamber of the heart to another. Natural heart or venous valves become dysfunctional for a variety of pathological causes. Some pathologies may require complete surgical replacement of the natural valve with a valve prosthesis. An artificial heart valve is a device implanted in the heart of a patient with valvular heart disease.

Despite the marked improvements in prosthetic valve design and surgical procedures over the past decades, valve replacement does not provide a definitive cure to the patient. Instead, the outcome of patients undergoing valve replacement is affected by prosthetic valve hemodynamics, durability, and thrombogenicity.

Dopamine (DA, contracted from 3,4-dihydroxyphenethylamine) is an organic chemical of the catecholamine and phenethylamine families that plays several important roles in the brain and body. Polydopamine (PDA) is a dopamine-derived synthetic eumelanin polymer. Polydopamine can deposit via the oxidative self-polymerization of dopamine at slightly basic pH onto many kinds of surfaces. However, a fundamental understanding regarding the mechanism of formation is still lacking. Lynge et al., Polydopamine—a nature-inspired polymer coating for biomedical science, Nanoscale, 2011, 3:4916.

An ideal primer coating is one that can be universally applied to any substrate. In this regard, the use of polydopamine as a primer has attracted great interest since the discovery that simple immersion of a substrate in a dilute aqueous solution of dopamine, buffered to alkaline pH, results in the spontaneous deposition of a polydopamine film on the substrate. Messersmith et al. (Science. 2007, 318, 426-430) demonstrated that a polydopamine coating is able to form on virtually any type of substrate surface, including metals, metal oxides, ceramics, synthetic polymers and a wide range of other hydrophilic and hydrophobic materials. Polydopamine coatings have been used as a platform for the conjugation of synthetic polymers or biomolecules to a surface. For example, WO2011/005258 discloses the attachment of amine-functionalized polyethylene glycol (PEG-NH$_2$) to a polydopamine coating, to provide a hydrophilic outer layer.

Considering durability, a coating can be removed from a substrate either by gradual erosion of the substance of the coating and/or by the coating being detached from surface of the substrate. Thus, one way to enhance the durability of a coating is to strengthen the binding between the coating and the surface of the substrate. This can be achieved, inter alia, by treating the surface to be coated with a primer in order to achieve better adhesion between the coating and the surface.

SUMMARY

The present disclosure provides for a medical device having a coating, wherein the coating comprises (i) polydopamine, (ii) a polyether derivative, and (iii) antibodies and/or antibody fragments, wherein the polydopamine is covalently linked to the polyether derivative, and wherein the polyether derivative is covalently linked to the antibodies and/or antibody fragments.

The antibodies and/or antibody fragments may specifically bind to a cell surface antigen of endothelial progenitor cells or endothelial cells.

The present disclosure provides for a medical device having a coating, wherein the coating comprises (i) polydopamine, (ii) a polyether derivative, and (iii) antibodies and/or antibody fragments, wherein the polydopamine is covalently linked to the polyether derivative, wherein the polyether derivative is covalently linked to the antibodies and/or antibody fragments, and wherein the antibodies and/or antibody fragments specifically bind to a cell surface antigen of endothelial progenitor cells or endothelial cells.

Also encompassed by the present disclosure is an artificial valve having a coating, wherein the coating comprises: (i) polydopamine, (ii) a polyether derivative, and (iii) antibodies and/or antibody fragments, wherein the polydopamine is covalently linked to the polyether derivative, wherein the polyether derivative is covalently linked to the antibodies and/or antibody fragments, and wherein the artificial valve is an artificial heart valve or artificial venous valve.

Non-limiting examples of the cell surface antigens include CD34, CD133, CDw90, CD117, HLA-DR, VEGFR-1, VEGFR-2, VEGFR-3, Muc-18 (CD146), Thy-1, Thy-2, CD130, CD30, stem cell antigen (Sca-1); stem cell factor 1 (SCF/c-Kit ligand), Tie-1, Tie-2, VE-cadherin, P1H12, TEK, CD31, Ang-1, Ang-2, HAD-DR, CD45, CD105, CD14, von Willebrand factor (vWF), and E-selectin.

The polyether derivative may be polyethylene glycol (PEG), a polyethylene glycol (PEG) derivative, polypropylene glycol (PPG), a polypropylene glycol (PPG) derivative, or combinations thereof.

The PEG may have an average molecular weight ranging from about 200 Daltons to about 20,000 Daltons, from about 200 Daltons to about 5,000 Daltons, from about 200 Daltons to about 1,000 Daltons, from about 200 Daltons to about 350 Daltons.

The medical device may be a stent, an artificial heart valve, a vascular prosthetic filter, a catheter, a pacemaker, a vascular graft, a synthetic graft, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, an artificial venous valve, a shunt, a wire, a sensor, a suture, a vascular anastomosis clip, an indwelling venous or arterial catheter, a vascular sheath or a chug delivery port.

The medical device may be an artificial heart valve or artificial venous valve, such as an artificial aortic valve, an artificial pulmonary valve, an artificial mitral valve, or an artificial tricuspid valve.

The medical device may comprise metal (such as stainless steel), an alloy, and/or a polymer. The polymer may be a biocompatible polymer, such as polytetrafluoroethylene (PTFE), dacron, polyurethane, polypropylene, or combinations or derivatives thereof.

The coating may or may not further comprise a pharmaceutical substance. In one embodiment, the pharmaceutical substance inhibits smooth muscle cell migration and/or proliferation. In another embodiment, the pharmaceutical substance is a vasodilator.

Non-limiting examples of the pharmaceutical substances include paclitaxel, rapamycin, a rapamycin derivative, sirolimus, everolimus, tacrolimus, biolimus, biolimus A-9, or combinations thereof.

The antibodies and/or antibody fragments may be monoclonal or polyclonal. The antibodies and/or antibody fragments may be humanized antibodies or antibody fragments, or chimeric antibodies or antibody fragments. The antibodies and/or antibody fragments may comprise Fab, F(ab')$_2$, or single chain Fv (scFv).

In one embodiment, the antibodies and/or antibody fragments specifically bind to different cell surface antigens.

The antibodies and/or antibody fragments of the medical device may capture endothelial progenitor cells and/or endothelial cells in vivo when the medical device is implanted into a subject.

The present disclosure provides for a method for treating or preventing a vascular disease, the method comprising the step of implanting into a patient the present medical device.

The vascular disease may be atherosclerosis, restenosis, thrombosis, and/or blood vessel occlusion.

BRIEF DESCRIPTION OF THE DRAWINGS

FIG. 1A: Non-oriented immobilization using a dextran coating. FIG. 1B: non-oriented immobilization using amine coupling. Both 1A and 1B can result in antigen binding regions buried. FIG. 1C: Oriented immobilization of antibody to PEG-modified surface via the modified Fc region of the antibodies. The antigen binding sites remain available for immunobinding.

FIG. 2A: Polydopamine deposit-basis of coating. FIG. 2B: Linker layer polyethylene glycol (PEG) deposit-basis of oriented-antibody coating. FIG. 2C: Oriented antibody coating.

FIGS. 4A and 4B illustrate exemplary structures and polymer configurations that polydopamine may form by oxidative self-polymerization which occurs when coating a substrate/medical device (e.g., 316L stainless steel (316S), cobalt-chromium (CoCr), ePTFE, or pericardium) from dopamine in a basic environment.

FIG. 8A: A polydopamine-coated substrate reacts with amino-PEG-dibenzocyclooctyne (DBCO). FIG. 8B: Functionalization of antibodies to create DBCO-reactive moieties (e.g., at the Fc region of the antibody). Step 1 shows removal of terminal galactose residues; Step 2 shows incorporation of GalNAz. See, Zeglis et al., Chem. 2013, 24 (6), 1057-1067. Qu et al., Adv. Healthc. Mater. 2014, 3 (1), 30-35. FIG. 8C: reaction of functionalized antibodies with the PEG linker.

FIG. 9 shows the fluorescence intensities of binding of an azide functionalized fluorescent probe (Carboxyrhodamine 110-Azide) on dibenzocyclooctyne (DBCO) functionalized substrates (e.g., disks). "Bare": a bare metal disk of CoCr that was not treated or coated. "Bare+DBCO": a bare metal disk that was coated with just DBCO but not with polydopamine. "PDOP": a bare metal disk that was coated with polydopamine. "PDOP+DBCO": a bare metal disk that was coated with polydopamine and then DBCO.

FIG. 10 shows capture of CD34-expressing Kg1a cells ("Positive") on 316L SS coronary stent coated with anti-CD34 antibodies (BioLegend, catalog #343602) via an intermediate Amino-dPEG$_8$-t-boc-hydrazide linker bound to polydopamine formed by oxidative self-polymerization of dopamine. Coatings were blocked with bovine serum albumin (BSA) before incubation with cells. Bound cells were visualized by the nuclear dye Sytox Green staining on confocal microscopy. Control cells were CHO cells that do not express CD34 ("Negative").

FIG. 11 shows capture of CD34-expressing Kg1a cells ("Positive") on cobalt chromium (CoCr) disks coated with anti-CD34 antibodies (BioLegend, #343602) via an intermediate Amino-dPEG$_8$-t-boc-hydrazide linker bound to polydopamine formed by oxidative self-polymerization of dopamine. Coatings were blocked with bovine serum albumin (BSA) before incubation with cells. Bound cells were visualized by the nuclear dye Sytox Green staining on confocal microscopy. Control cells were CHO cells that do not express CD34 ("Negative").

FIG. 12 shows capture of CD34-expressing Kg1a cells ("Positive") on medical grade expanded polytetrafluoroethylene (ePTFE) endograft coated with anti-CD34 antibodies (BioLegend, #343602) via an intermediate Amino-dPEG$_8$-t-boc-hydrazide linker bound to polydopamine formed by oxidative self-polymerization of dopamine. Coatings were blocked with bovine serum albumin (BSA) before incubation with cells. Bound cells were visualized by the nuclear dye Sytox Green staining on confocal microscopy. Control cells were CHO cells that do not express CD34 ("Negative").

FIG. 13 shows stability assessment of CD34+ cells or CD34− cells bound on anti-CD34 antibody-coated ePTFE. The ePTFE substrate was placed in PBS for 12 days and then used for cell binding. Bound cells were stained with fluorescence dye and observed under confocal microscope.

DETAILED DESCRIPTION OF THE INVENTION

Figure 1:
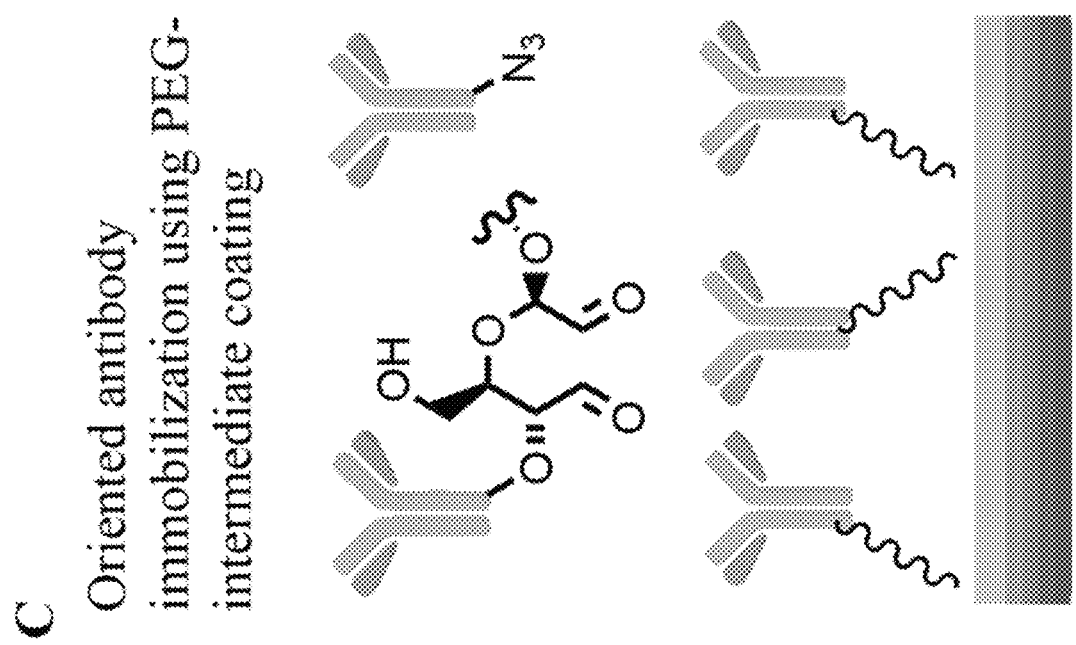
FIGS. 1A-1C show different antibody immobilization techniques.
Figure 2A:
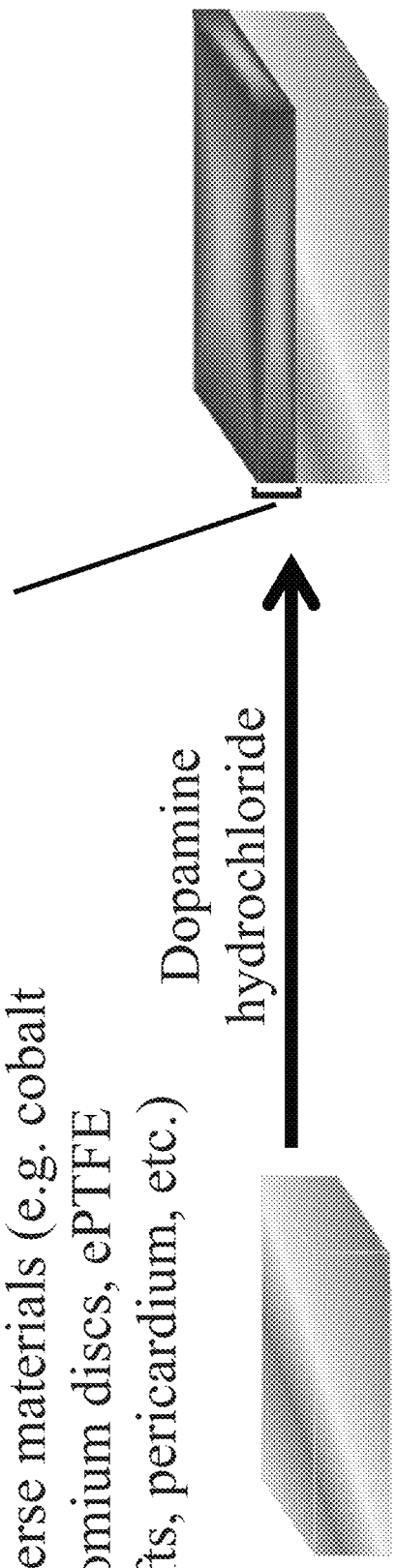
FIGS. 2A-2C show schemes forming the present coating.
Figure 2B:
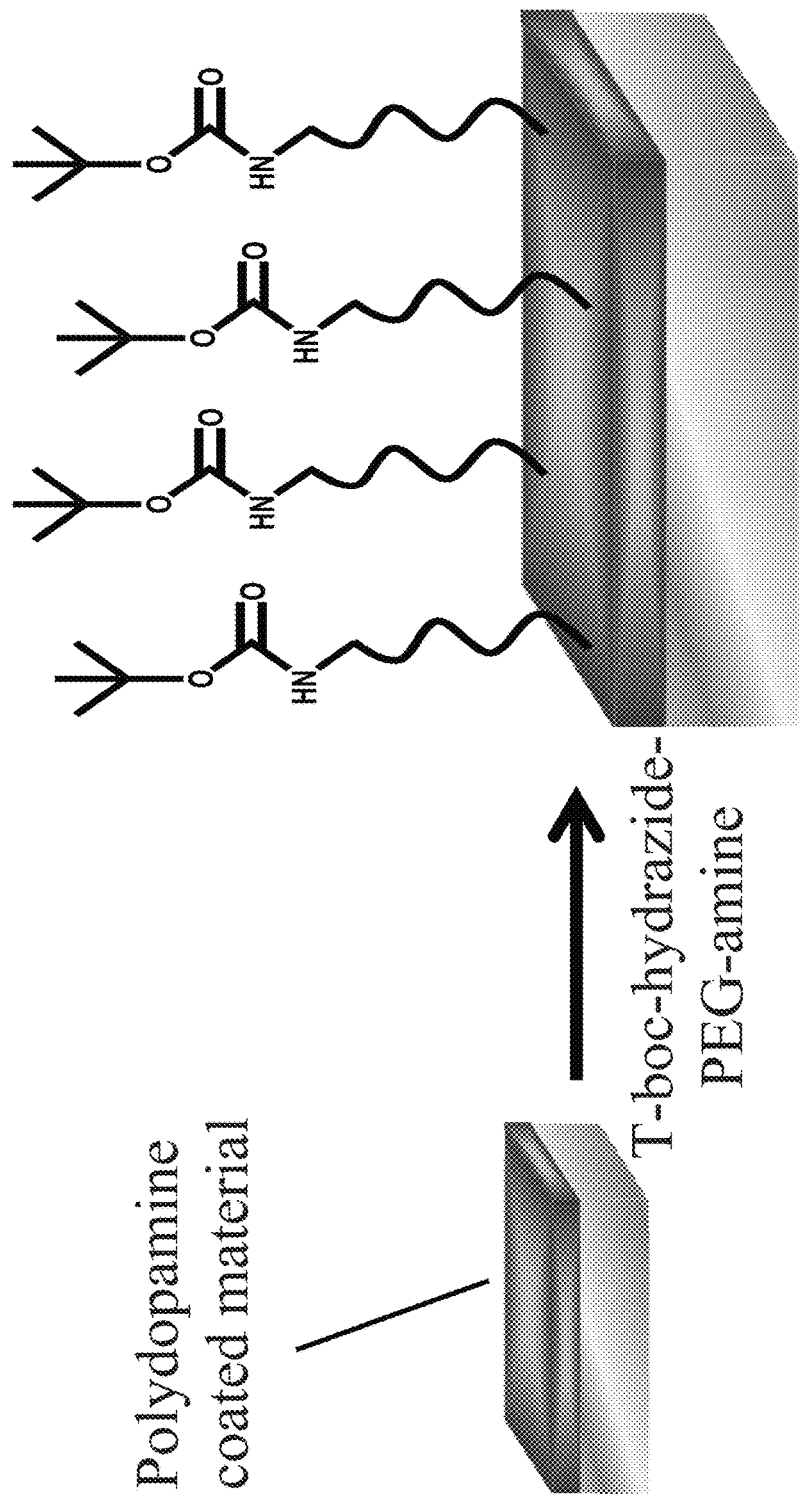
Figure 2C:
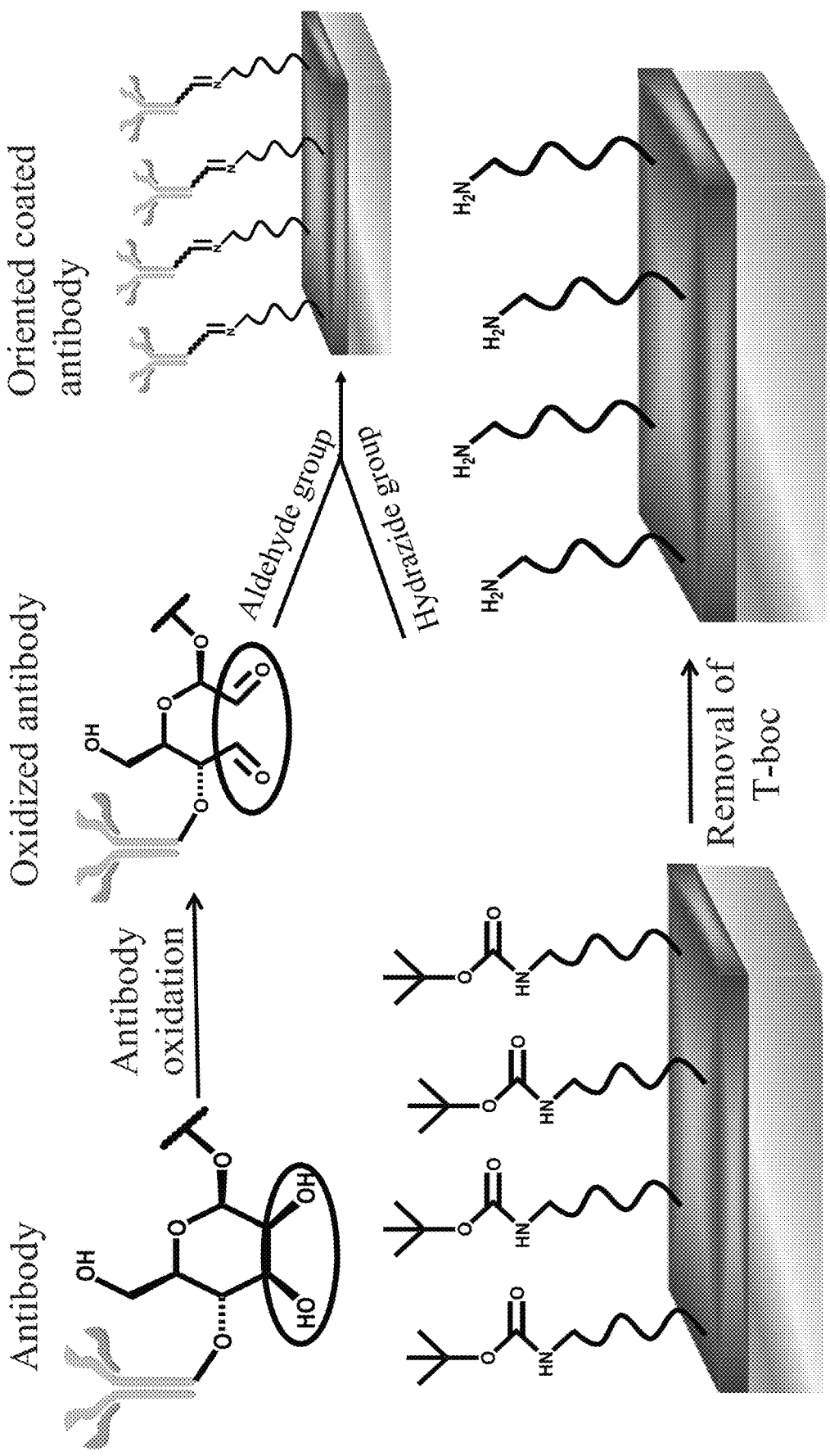
Figure 3:
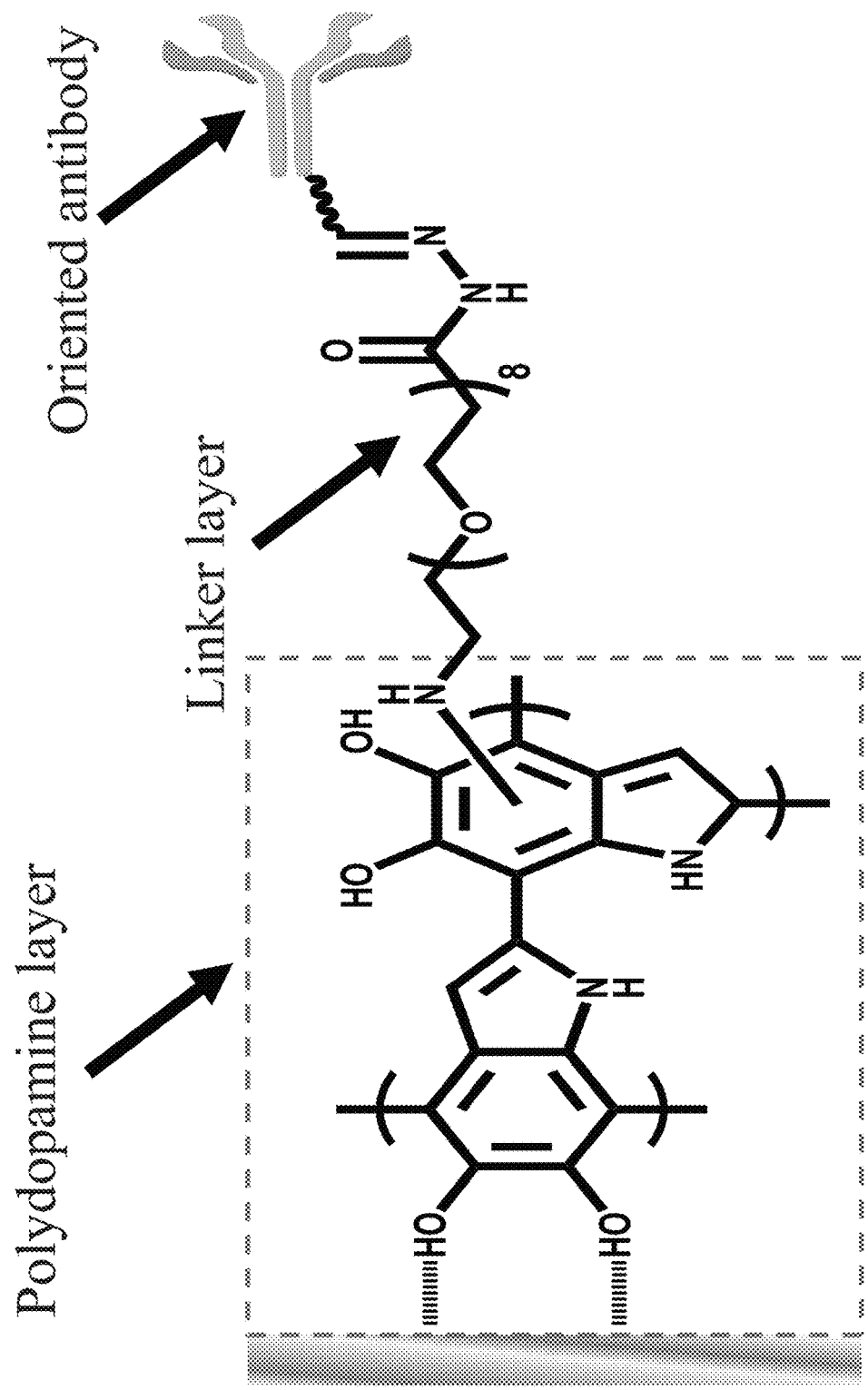
FIG. 3 shows the general structure of an embodiment of the present coating.

The present disclosure provides for a medical device or a substrate coated with a melanin, a melanin-like polymer, a synthetic version of melanin, or an aromatic catechol polymer (e.g., polydopamine or polymers of dopamine analogues) which is further linked to ligands/biomolecules such as antibodies and/or antibody fragments. The polydopamine coating and the ligands may be linked through a linker such as an organic polymer/oligomer. The present disclosure provides for a medical device (e.g., a stent, an artificial valve, etc.) coated with (i) polydopamine, (ii) an organic polymer (e.g., a polyether derivative, such as polyethylene glycol (PEG), as well as the other organic polymer/oligomer described herein), and (iii) antibodies and/or antibody fragments. The polydopamine may be covalently linked to the organic polymer/oligomer, and the organic polymer/oligomer may be covalently linked to the antibodies and/or antibody fragments. The antibodies and/or antibody fragments may specifically bind to a cell surface antigen/molecule of endothelial progenitor cells (EPCs) or endothelial cells, such as anti-CD34 antibodies. The antibodies and/or antibody fragments may capture endothelial progenitor cells and/or endothelial cells in vivo when the medical device is implanted into a subject. The medical device may also comprise a pharmaceutical substance or a therapeutic agent.

The present disclosure provides for a medical device coated with (i) a melanin, a melanin-like polymer, a synthetic version of melanin, or an aromatic catechol polymer (e.g., polydopamine or polymers of dopamine analogues), (ii) an organic polymer (e.g., a polyether derivative, such as polyethylene glycol (PEG), as well as the other organic polymer/oligomer described herein), and (iii) ligands/biomolecules (e.g., antibodies and/or antibody fragments). The melanin, melanin-like polymer, synthetic version of melanin, or aromatic catechol polymer (e.g., polydopamine or polymers of dopamine analogues) may be covalently linked to the organic polymer/oligomer, and the organic polymer/oligomer may be covalently linked to the ligands/biomolecules (e.g., antibodies and/or antibody fragments). The ligands/biomolecules (e.g., antibodies and/or antibody fragments) may specifically bind to a cell surface antigen/molecule of endothelial progenitor cells or endothelial cells.

The present coating may be applicable to a wide range of substrates/materials, is biocompatible, and provides facile chemistry and broad reactivity toward a wide range of ligands/biomolecules. The ligands/biomolecules can be bound to the coating in an oriented manner. The coating also has long-term chemical stability.

In one embodiment, the polydopamine coating is formed via the oxidative self-polymerization of dopamine under basic conditions (e.g., slightly basic conditions) on the surface of a medical device or a substrate. Subsequently, the polyethylene glycol (PEG) linker is applied, which conjugates with the polydopamine coating at one end, and conjugates at the other end with the Fc fragment of antibodies or antibody fragments.

The coating of the medical device may further comprise antibodies, antibody fragments or combinations thereof, wherein the antibodies, antibody fragments or combinations thereof specifically bind to a cell surface antigen of endothelial progenitor cells or endothelial cells. In certain embodiments, the cell surface antigen is CD133, CD34, CDw90, CD117, HLA-DR, VEGFR-1, VEGFR-2, VEGFR-3, Muc-18 (CD146), Thy-1, Thy-2, CD130, CD30, stem cell antigen (Sca-1), stem cell factor 1 (SCF/c-Kit ligand), Tie-1, Tie-2, VE-cadherin, P1H12, TEK, CD31, Ang-1, Ang-2, HAD-DR, CD45, CD14, CD105, E-selectin, von Willebrand factor (vWF), or combinations thereof.

The medical device may comprise a blood-contacting surface (or a luminal surface) for attaching the present coating. The ligands (such as antibodies and/or antibody fragments) may interact with an antigen on the target cell such as an endothelial progenitor cell (EPC) to immobilize the endothelial progenitor cell on the surface of the device to form endothelium.

The ligand may be a molecule that binds a cell membrane structure such as a receptor molecule on the circulating endothelial cell and/or endothelial progenitor cell. For example, the ligand can be an antibody, antibody fragment, small molecules such as peptides, cell adhesion molecule, basement membrane components, or combination thereof. In the embodiment using antibodies, the antibodies recognize and bind a specific epitope or structure, such as cell surface receptor on the cell membrane of the cell. The ligands may also be derived from a variety of sources such as cellular components including, fatty acids, peptides, proteins, nucleic acids, saccharides and the like and can interact, for example, with a structure such as an antigen on the surface of a progenitor endothelial cell with the same results or effects as an antibody.

The ability of antibodies to bind to target proteins at solid-liquid interfaces is central to in vitro diagnostic assays as well as in vivo therapeutics using antibodies. In order for the Fab domain of the immobilized antibody to bind to the antigen, the Fab domain (i) must be accessible, i.e., has an outward orientation from the interface, and (ii) is biologically active, i.e., has a molecular conformation with a low dissociation constant (Kd) for the target molecule. The activity of immobilized antibodies varies sensitively between different immobilization chemistries. Antibodies with more accessible Fab domains exhibit higher activity than randomly immobilized antibodies. Several techniques may be used to determine the activity, accessibility and orientation of immobilized antibodies, including, but not limited to, atomic force microscopy, neutron reflection, spectroscopic ellipsometry and mass spectrometry. Saha et al. Analyst, 2017, 142, 4247-4256. Quantitative radio-labelled assays may also be used to determine accessibility of the Fab domain. Id.

The ligands/biomolecules may be immobilized on the medical device in an oriented manner, to ensure accessibility of the active sites of the ligands/biomolecules. This may be achieved by conjugating the ligands/biomolecules at a specific site away/different from the active sites of the ligands/biomolecules. In one embodiment, the ligands/biomolecules (e.g., antibodies or antibody fragments) may be immobilized on the medical device via a site outside of their active site (e.g., Fab region or domain, antigen-binding site or domain).

For example, the ligands/biomolecules (e.g., antibodies or antibody fragments) of the coating have an accessibility (e.g., Fab accessibility) of their active site (e.g., Fab region or domain, antigen-binding site or domain) of at least 1%, at least 3%, at least 5%, at least 8%, at least 10%, at least 15%, at least 20%, at least 25%, at least 30%, at least 35%, at least 40%, at least 45%, at least 50%, at least 60%, at least 70%, at least 80%, or at least 90% of the total active sites of the ligands/biomolecules (e.g., antibodies or antibody fragments) of the coating.

In one embodiment, the ligands/biomolecules (e.g., antibodies or antibody fragments) of the coating have an accessibility of their active site (e.g., Fab region or domain, antigen-binding site or domain) about 5%, about 8%, about 10%, about 15%, about 20%, about 25%, about 30%, about 35%, about 40%, about 45%, about 50%, about 60%, about 70%, about 80%, about 90%, at least 1%, at least 3%, at least 5%, at least 8%, at least 10%, at least 15%, at least 20%, at least 25%, at least 30%, at least 35%, at least 40%, at least 45%, at least 50%, at least 60%, at least 70%, at least 80%, or at least 90%, greater than the accessibility of their active site (e.g., Fab region or domain, antigen-binding site or domain) of ligands/biomolecules (e.g., antibodies or antibody fragments) attached to a coating (e.g., polydopamine coating) in a non-oriented manner.

In another embodiment, at least 1%, at least 3%, at least 5%, at least 8%, at least 10%, at least 15%, at least 20%, at least 25%, at least 30%, at least 35%, at least 40%, at least 45%, at least 50%, at least 60%, at least 70%, at least 80%, or at least 90%, of the ligands/biomolecules have their active sites (e.g., Fab region or domain, antigen-binding site or domain) accessible. In other words, at least 1%, at least 3%, at least 5%, at least 8%, at least 10%, at least 15%, at least 20%, at least 25%, at least 30%, at least 35%, at least 40%, at least 45%, at least 50%, at least 60%, at least 70%, at least 80%, or at least 90%, of the active sites (e.g., Fab region or domain, antigen-binding site or domain) of the ligands/biomolecules are not blocked or denatured. This may be achieved by conjugating the ligands/biomolecules at a specific site away from the active sites of the ligands/biomolecules.

In yet another embodiment, at least 1%, at least 3%, at least 5%, at least 8%, at least 10%, at least 15%, at least 20%, at least 25%, at least 30%, at least 35%, at least 40%, at least 45%, at least 50%, at least 60%, at least 70%, at least 80%, or at least 90%, of the antibodies and/or antibody fragments are available for binding to the cell surface antigen.

Accessibility of Fab and/or Fc domains of immobilized antibodies may be analyzed according to Saha et al. Analyst 142:4247-4256 (2017). Fab domain accessibility assay—a known amount of an antibody-coated devices (e.g., disks, ePTFE grafts, stents) may be incubated with a molar excess (relative to the molar amount of bound antibody) of an antigen, which is capable of binding to the bound antibody. Using a molar excess will saturate available antibody domains. After incubation, the coated device is washed and a second, radiolabeled (e.g., 125I-labeled) antibody which binds to a different epitope from the first antibody may be added in a molar excess (relative to the amount of bound antibody). Stocks of different known concentrations of radiolabeled second antibody in solution may be taken as a control. The amount of bound second radiolabeled antibody in the Fab accessibility assay may then be calculated by subtracting the signal of antibody-coated devices from the final signal after binding of the second radiolabeled monoclonal antibody. Saha et al. Analyst 142:4247-4256 (2017). Other techniques used to determine the activity, accessibility and orientation of immobilized antibodies, include, atomic force microscopy, neutron reflection, spectroscopic ellipsometry and mass spectrometry. Id.

Cell adhesion may be assessed using a suitable method, such as cell adhesion assays. Adherent cells may be quantified using colorimetric or fluorometric detection.

The present disclosure provides for an artificial heart valve or an artificial venous valve having a coating comprising polydopamine. In certain embodiments, the valve is an artificial aortic valve, an artificial pulmonary valve, an artificial mitral valve, an artificial tricuspid valve.

The antibodies and/or antibody fragments may be monoclonal, or polyclonal. In one embodiment, the antibodies and/or antibody fragments comprises Fab or F(ab')$_2$ fragments. The antibodies and/or antibody fragments may specifically bind to different cell surface antigens.

The linker may be hetero- or homo-bifunctional. After covalent coupling to the matrix, the linker molecules provide the matrix with a number of functionally active groups that can be used to covalently couple one or more types of antibody. The linker may be coupled to the polydopamine coating directly (i.e., through the catechol groups), or through well-known coupling chemistries, such as, esterification, amidation, and acylation. The linker molecule may be a di-, tri- or tetra-amine functional compound that is coupled to the polydopamine coating through the direct formation of amine-carbon saturated and unsaturated bonds, and provides amine-functional groups that are available for reaction with the ligands (e.g., antibodies and/or antibody fragments). For example, the linker molecule may be polyethyleneglycol (PEG), a polyamine functional polymer such as polyethyleneimine (PEI), polyallylamine (PALLA), or a PEG derivative (e.g., mPEG-succinimidyl propionate or mPEG-N-hydroxysuccinimide). See, Weiner et al., Influence of a poly-ethyleneglycol spacer on antigen capture by immobilized antibodies. J. Biochem. Biophys. Methods 45:211-219 (2000), incorporated herein by reference. Mixtures of the polymers can also be used. These molecules contain a plurality of pendant amine-functional groups that can be used to surface-immobilize one or more ligands (e.g., antibodies and/or antibody fragments).

The coating of the medical device may further comprise a pharmaceutical substance, such as a pharmaceutical substance that inhibits smooth muscle cell migration and/or proliferation. In certain embodiments, the pharmaceutical substance is paclitaxel, rapamycin, a rapamycin derivative, sirolimus, everolimus, tacrolimus, biolimus, biolimus A-9, or combinations thereof. The pharmaceutical substance may be a vasodilator.

The coated medical device may provide targeted local drug delivery (e.g., of the pharmaceutical substance), and/or systemic therapies.

The medical device can be any device that is introduced temporarily or permanently into a mammal for the prophylaxis or therapy of a medical condition. These devices include any that are introduced subcutaneously, percutaneously or surgically to rest within an organ, tissue or lumen of an organ, such as arteries, veins, ventricles and/or atrium of the heart. Medical devices may include stents, stent grafts; covered stents such as those covered with polytetrafluoroethylene (PTFE), expanded polytetrafluoroethylene (ePTFE), or synthetic vascular grafts, artificial heart valves, artificial hearts and fixtures to connect the prosthetic organ to the vascular circulation, venous valves, abdominal aortic aneurysm (AAA) grafts, inferior venal caval filters, permanent drug infusion catheters, embolic coils, embolic materials used in vascular embolization (e.g., cross-linked PVA hydrogel), vascular sutures, vascular anastomosis fixtures, transmyocardial revascularization stents and/or other conduits.

The present disclosure provides for an artificial heart valve or an artificial venous valve having a coating comprising polydopamine. In certain embodiments, the valve is an artificial aortic valve, an artificial pulmonary valve, an artificial mitral valve, or an artificial tricuspid valve.

The coating of the artificial valve may further comprise a pharmaceutical substance, such as a pharmaceutical substance that inhibits smooth muscle cell migration and/or proliferation. In certain embodiments, the pharmaceutical substance is paclitaxel, rapamycin, a rapamycin derivative, sirolimus, everolimus, tacrolimus, biolimus, biolimus A-9, or combinations thereof.

In another embodiment, there is provided a method for treating a vascular disease such as restenosis and artherosclerosis, comprising implanting the present medical device in a patient in need of such medical device. The method comprises implanting a medical device with the present coating into a vessel or hollowed organ of a patient.

The term "endothelial progenitor cell" includes cells of any lineage that have the potential to differentiate into mature, functional endothelial cells. For example, the endothelial progenitor cells are endothelial cells at any developmental stage, from progenitor or stem cells to mature, functional endothelial cells from bone marrow, blood or local tissue origin and which are non-malignant, cells that are genetically-modified. Endothelial progenitor cells may include endothelial colony forming cells (ECFCs) and myeloid angiogenic cells (MACs). Endothelial colony forming cells may be CD31+, CD105+, CD146+, CD45−, and/or CD145−. Endothelial colony forming cells may possess intrinsic tube forming capacity in vitro and in vivo. Endothelial colony forming cells may be building blocks for new blood vessel formation or vascular repair. Myeloid angiogenic cells may be CD45+, CD14+, CD31+, CD146−, and/or CD34−. Myeloid angiogenic cells-conditioned media may enhance endothelial network formation in vitro and in vivo. MAC-derived paracrine factors may be stimulants of angiogenesis. Medina et al., Endothelial Progenitors: A Consensus Statement on Nomenclature. Stem Cells Translational Medicine, 2017; 6:1316-1320.

For in vitro studies or use of the coated medical device, fully differentiated endothelial cells may be isolated from an artery or vein such as a human umbilical vein, while endothelial progenitor cells may be isolated from peripheral blood or bone marrow. The endothelial cells are bound to the medical devices by incubation of the endothelial cells with a medical device with the present coating, in another embodiment, the endothelial cells can be transformed/transfected endothelial cells.

The ligands can be small molecules comprising synthetic or naturally occurring molecules or peptides which can be used in place of antibodies or antibody fragments, or in combination with antibodies or antibody fragments. For example, lectin is a sugar-binding peptide of non-immune origin which occurs naturally. The endothelial cell specific lectin antigen (Ulex Europaeus Uea 1) (Schatz et al. 2000 Human Endometrial Endothelial Cells: Isolation, Characterization, and Inflammatory-Mediated Expression of Tissue Factor and Type 1 Plasminogen Activator Inhibitor. Biol Reprod 62: 691-697) can selectively bind the cell surface of progenitor endothelial cells. Synthetic small molecules have been created to target various cell surface receptors. These molecules selectively bind a specific receptor(s) and can target specific cell types such as endothelial progenitor cells and/or endothelial cells. Small molecules can be synthesized to recognize endothelial cell surface markers such as VEGF. For example, SU11248 (Sugen Inc.) (Mendel et al. 2003 In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res. January; 9(1):327-37), PTK787/ZK222584 (Drevs J. et al. 2003 Receptor tyrosine kinases: the main targets for new anticancer therapy. Curr. Drug Targets. February; 4(2): 113-21) and SU6668 (Laird, A D et al. 2002 SU6668 inhibits Flk-1/KDR and PDGFRbeta in vivo, resulting in rapid apoptosis of tumor vasculature and tumor regression in mice, FASEB J. May; 16(7):681-90) are small molecules which bind to VEGFR-2. In another embodiment, another subset of synthetic small molecules which target the endothelial cell surface are, for example, the alpha(v)beta(3) integrin inhibitors. S5M256 and SD983 (Kerr J S. et al. 1999 Novel small molecule alpha v integrin antagonists: comparative anti-cancer efficacy with known angiogenesis inhibitors can be used. Anticancer Res March-April; 19(2A)-959-68). SM256 and SD983 are both synthetic molecules which target and bind to alpha(v)beta(3) present on the surface of endothelial cells.

In one embodiment, a substrate/medical device (comprising, or made of, cobalt chromium, stainless steel, ePTFE, and/or polystyrene, etc.) is coated with a polydopamine film, amine functionalized polyethylene glycol is deposited onto polydopamine-coated substrate/medical device. Functionalized ligands/biomolecules are introduced to react with functionalized PEG.

In another embodiment, ligands/biomolecules (e.g., antibodies or antibody fragments) are directly immobilized on a polydopamine film. For example, freshly prepared polydopamine-coated substrate/medical device is exposed to an unmodified antibody (or antibody fragment) solution in a buffer (e.g., PBS). The antibody (or antibody fragment) coated substrate/medical device is then rinsed thoroughly with a buffer (e.g., PBS) to remove adsorbed antibody.

The present coated medical device may be used to capture/bind native/normal cells, or genetically modified cells. The genetically modified cells may secrete a pharmaceutical substance as described herein constitutively or when stimulated to do so.

In one embodiment, circulating endothelial progenitor cells can be the target cells which can be captured and immobilized on the luminal or blood-contacting surface of the device to restore, enhance or accelerate the formation of a functional endothelium at the site of implantation of the device.

In another embodiment, the ligands/biomolecules (e.g., antibodies or antibody fragments) specifically bind only the genetically-modified cells (e.g., mammalian cells such as human cells) by recognizing only the cell surface a cell surface antigen/molecule of the genetically-modified cells which are genetically-modified to express the cell surface antigen/molecule. The binding of the target cells to the ligands/biomolecules may immobilize the cells on the surface of the device. In this manner, only the genetically-modified cells can bind to the surface of the medical device.

The ligands/biomolecules (e.g., antibodies or antibody fragments) may be specific for binding to cell surface antigen such as CD133, CD34, CD14, CDw90, CD117, HLA-DR, VEGFR-1, VEGFR-2, Muc-18 (CD146), CD130 stem cell antigen (Sca-1), stem cell factor 1 (SCF/c-Kit ligand), Tie-2, MHC such as H-2K$^k$ and HLA-DR, or a synthetic antigen.

In one embodiment, EPCs are genetically modified to express vasodilators, e.g., to promote flow-dependent positive remodeling of epicardial coronary arteries.

The melanin, melanin-like polymer, synthetic version of melanin, or aromatic catechol polymer include, but are not limited to, polydopamine, polymers of dopamine analogues, eumelanin, pheomelanin, and neuromelanin.

Polydopamine

Polydopamine is formed by the polymerization of the monomer dopamine. In certain embodiments, polydopamine (PDA) is a synthetic eumelanin polymer formed via the oxidative self-polymerization of dopamine under slightly basic conditions. In one embodiment, a PDA film can be formed by immersing a substrate/medical device into an aqueous dopamine solution.

The exact structure of polydopamine is not well understood, and a number of structures have been proposed.

Polymerization of dopamine may occur under oxidative conditions. Exposure to the air (i.e., oxygen) may be sufficient to initiate polymerization. In one embodiment, the initial oxidation of dopamine occurs on the catechol moiety, which then reacts with another molecule of dopamine, or can undergo an intermolecular cyclization (via the pendant primary amine) to form a nitrogen-containing bicycle. One structure (Structure A) of polydopamine (as described in WO2010/006196) suggests that polydopamine consists of repeating 5,6-dihydroxy-3H-indole units, cross-linked through positions 4 and 7. Another structure (Structure B, as described by Zhao et al. Polym. Chem., 2010, 1, 1430-1433) suggests a similar polymer, but every other 5,6-dihydroxy-3H-indole unit is replaced with a 5,6-dihydroxyindoline unit. Structure C is proposed as another possible structure for polydopamine, which again is similar to Structure A, but every other 5,6-dihydroxy-3H-indole unit is replaced with an un-cyclized dopamine molecule (U.S. Pat. No. 9,272,075). This structure of polydopamine therefore comprises primary amine functionalities. Structure D (described in Kang et al. Langmuir, 2009, 25, 9656-9659) is also proposed and suggests attachment between dopamine molecules at the five-membered nitrogen ring, as well as between the catechol rings. This structure also suggests that quinone rings as well as catechol rings are present in the polymeric structure. Finally, Structure E (described by Dreyer et al. Langmuir, 2012, 28, 642S-6435) illustrates a completely different structure in which polydopamine is not a covalent polymer but is instead a supramolecular aggregate of monomers, consisting primarily of 5,6-dihydroxyindoline and its dione derivative.

It should be noted that in the context of the present disclosure, the representation of the structure of polydopamine is immaterial for working the method and coating of the invention, and the discussion above is merely included for background reference.

As referred to herein, "polydopamine" is suitably formed by polymerization of dopamine and/or a dopamine analogue. In one embodiment, polydopamine is formed by polymerization of dopamine. Dopamine analogues include molecules involved in the same or similar biochemical pathways as dopamine and those that are similar in structure to dopamine, including oxidized derivatives of tyrosine. In one embodiment, a dopamine analogue is a compound of formula (I), wherein one or more of $R^1$-$R^9$ are not H:

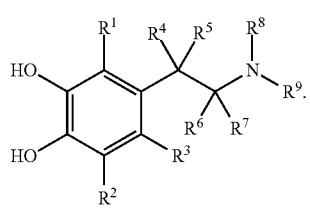

(I)

In another embodiment, a dopamine analogue is a compound of formula (I), wherein $R^1$-$R^9$ are independently selected from the group consisting of: H, $C_1$-$C_8$ alkyl, $C_2$-$C_8$ alkenyl, $C_2$-$C_8$ alkynyl, —OH, —$CO_2H$, —C(O)$C_1$-$C_8$ alkyl, —C(O)$C_2$-$C_8$ alkenyl, —C(O)$C_2$-$C_8$ alkynyl.

Naturally occurring dopamine analogues include:

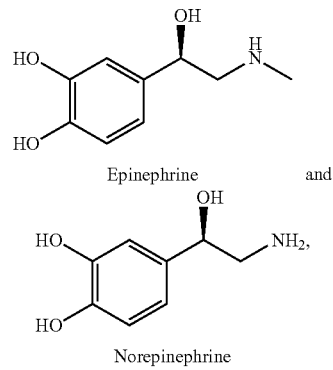

Epinephrine and Norepinephrine

Other exemplary dopamine analogues are illustrated below:

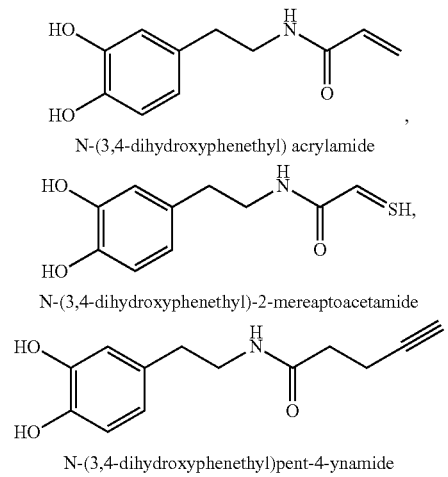

N-(3,4-dihydroxyphenethyl) acrylamide,

N-(3,4-dihydroxyphenethyl)-2-mereaptoacetamide

N-(3,4-dihydroxyphenethyl)pent-4-ynamide

Methods for Preparing a Polydopamine Coating

Dopamine in an aqueous alkaline solution exposed to the air (i.e., oxygen) may polymerize to form polydopamine without additional reactants. However, the rate of polymerization can be increased by the addition of a chemical oxidant to the solution or an oxidizing electrical current containing dopamine. Suitable chemical oxidants include, but are not limited to, ammonium persulfate and sodium persulfate. Thus, in one embodiment, a surface coating of polydopamine is formed by contacting the surface of the substrate with a mixture comprising oxidant and dopamine and/or a dopamine analogue.

Polymerization of dopamine has also been observed to be quicker in alkaline aqueous solution, presumably due to deprotonation and activation of the catechol hydroxyl groups to oxidation. The use of an oxidant may allow the polymerization of dopamine to proceed in a controlled manner at neutral or even acidic pH, within a reasonable time frame. Suitable oxidants include ammonium persulfate and sodium persulfate. U.S. Pat. No. 9,272,075.

In one embodiment, the surface coating of polydopamine is formed by contacting the surface of the substrate with a mixture comprising oxidant and dopamine and/or a dopamine analogue, at pH 4-10, for example pH>7 or pH 7. In another embodiment, the surface coating of polydopamine is formed at pH<7, e.g., pH 4-7. In a further embodiment, the surface coating of polydopamine is formed at pH 5-6.9, e.g., pH 5.5-6.5. The pH of the dopamine and/or dopamine analogue solution can be adjusted using any suitable acid or base, such as HCl or NaOH, respectively. The pH of the solution can be controlled with a suitable buffer, e.g., MES, ACES, PIPES, MOPSO, Bis-Tris propane, BES, MOPS, TES and HEPES buffer.

The amount of oxidant affects the rate of polymerization. In one embodiment, the amount of dopamine in the solution is between 1 g/L to 5 g/L and the amount of ammonium persulfate (APS) in the solution is between 0.6 g/L and 3 g/L. In another embodiment 1 g/L of dopamine and 0.6 g/L of APS are used for the polymerization. The polymerization rate may be increased by increasing the dopamine and/or APS concentration. In certain embodiments, the concentration of dopamine or analogue may be 0.5-10 g/L, and the concentration of APS may be 0.1-5 g/L.

Polymerization of dopamine can be performed in aqueous solutions or in aqueous/organic mixtures such as mixtures of Water with methanol, ethanol, propanol and/or isopropanol.

The time required to form a polydopamine coating may vary depending on the specific reaction conditions used. For example, the addition of an oxidant may speed up polymerization, or allow the use of a neutral or even acidic pH. The polydopamine coating may be formed within a time period that is feasible for efficient manufacture. For example, the desired polydopamine coverage can be formed within 24 hours, 12 hours, 6 hours, 5 hours, 4 hours, 3 hours, 2 hours, 1 hour, 30 minutes, 10 minutes, 5 minutes, or 2 minutes. Zangmeister et al., Langmuir 2013, 29 (27), 8619-8628. As a general principle, the longer the polymerization time, the thicker the coating of polydopamine formed. Thus, the optimum time for polymerization of dopamine is long enough to obtain sufficient coverage of polydopamine, but not so long as to allow uncontrolled particulate polydopamine to be formed in solution. In certain embodiments, polymerization time is no longer than 24 hours, for example up to 12 hours, 6 hours, 5 hours, 4 hours, 3 hours, 2 hours, 1 hour, 30 minutes, 10 minutes, 5 minutes, or 2 minutes. In one embodiment, post-processing techniques such as ultrasonication may be used to remove polydopamine aggregates and particulates.

The polydopamine coating may be formed at room temperature, although the polymerization can be carried out at higher/lower temperatures.

The thickness of the polydopamine coating may range from about 0.1 nm to about 10 nm, about 1 nm to about 50 nm, from about 1 nm to about 40 nm, from about 1 nm to about 30 nm, about 1 nm to about 20 nm, from about 1 nm to about 15 nm, from about 1 nm to about 10 nm, about 1 nm to about 100 nm, from about 5 nm to about 80 nm, from about 6 nm to about 60 nm, from about 10 nm to about 50 nm, from about 10 nm to about 30 nm, from about 0.1 μm to about 150 μm, or from about 1 μm to about 100 μm. Zangmeister et al., Langmuir 2013, 29 (27), 8619-8628.

A possible alternative approach for forming polydopamine using electric charges (voltage) is described in Kang et al. Angewandte Chemie, 2012, vol. 124. pp 1-5.

Prior to coating, the surface of the substrate can be cleaned or pretreated in order to improve adhesion to polydopamine. Prior cleaning or pretreatment of the surface may also improve the uniformity of the coating.

Suitable cleaning agents or pre-treatment agents include solvents as ethanol or isopropanol (IPA), solutions with high pH such as solutions comprising a mixture of an alcohol and an aqueous solution of a hydroxide compound (e.g. sodium hydroxide), sodium hydroxide solution per se, solutions containing tetramethyl ammonium hydroxide (TMAH), basic Piranha (ammonia and hydrogen peroxide), acidic Piranha (a mixture of sulfuric acid and hydrogen peroxide), and other oxidizing agents including sulfuric acid and potassium permanganate or different types of peroxysulfuric acid or peroxydisulfuric acid solutions (also as ammonium, sodium, and potassium salts e.g., ammonium persulfate), or combinations thereof.

Two specific pretreatment methods—Method A and Method B—are described. Method A involves treating the substrate with isopropanol, while in Method B the substrate is treated with isopropanol then a solution of APS (ammonium persulfate). In one embodiment, prior to forming the surface coating of polydopamine, the surface of the substrate is pretreated with an oxidant. In another embodiment, prior to forming the surface coating of polydopamine, the surface of the substrate is treated with isopropanol and an oxidant. In a further embodiment, prior to forming the surface coating of polydopamine, the surface to be coated is pretreated with isopropanol and ammonium persulfate.

The polydopamine layer may be functionalized, e.g., with alkene and/or alkyne groups or thiol groups. Such a polydopamine surface can be prepared by polymerization of dopamine and dopamine analogues including at least a proportion of an alkene and/or alkyne or thiol group functionalized dopamine (or analogue). A synthetic dopamine analogue may be formed by functionalizing the primary amine of dopamine.

After polydopamine film formation, the substrate/medical device can be further functionalized with molecules containing amine and/or thiol groups which are common moieties found in biomolecules (e.g., proteins). Biomolecules may be immobilized under very mild conditions (e.g., at near neutral pH or neutral pH and room temperature).

Organic Polymers/Oligomers

Polydopamine and the ligands (e.g., antibodies and/or antibody fragments) may be linked through a linker such as an organic polymer/oligomer.

Non-limiting examples of organic polymers include a polyether derivative (e.g. polyethylene glycol (PEG), a polyethylene glycol (PEG) derivative, polypropylene glycol (PPG) or a polypropylene glycol (PPG) derivative), polysilicon, polydimethylsiloxane, a siloxane derivative, polyurethane, a protein, a peptide, a polypeptide, hyaluronic acid, a hyaluronic acid derivative, poly-N-vinylpyrrolidone, a poly-N-vinylpyrrolidone derivative, polyethylene oxide, a polyethylene oxide derivative, a polyalkylene glycol, polyglycidol, polyvinylalcohol, a polyvinylalcohol derivative, polyacrylic acid, a polyacrylic acid derivative, silicone, a silicone derivative, polysaccharide, a polysaccharide derivative, polysulfobetaine, a polysulfobetaine derivative, polycarboxybetaine, a polycarboxybetaine derivative, a polyalcohol such as polyHEMA, a polyacid such as an alginate, dextran, agarose, poly-lysine, polymethacrylic acid, a polymethacrylic acid derivative, polymethacrylamide, a polymethacrylamide derivative, a polyacrylamide, polyacrylamide derivative, polysulfone, a polysulfone derivative, sulfonated polystyrene, a sulfonated polystyrene derivative, polyallylamine, a polyallylamine derivative, polyethyleneimine, a polyethyleneimine derivative, polyoxazoline, a polyoxazoline derivative, polyamine, a polyamine derivative, and combinations thereof. Block polymers of above mentioned polymers are also useful; e.g., poly(vinyl alcohol-co-ethylene), poly(ethyleneglycol-copropyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine).

In certain embodiments, the organic polymer is hyaluronic acid, a hyaluronic acid derivative, poly-N-vinylpyrrolidone, a poly-N-vinylpyrrolidone derivative, a polyether derivative (e.g. polyethylene glycol (PEG), a polyethylene glycol (PEG) derivative, polypropylene glycol (PPG) or a polypropylene glycol (PPG) derivative, polyvinylalcohol, a polyvinylalcohol derivative, or combinations thereof. In certain embodiments, the organic polymer is polyethylene glycol (PEG), a polyethylene glycol (PEG) derivative, polypropylene glycol (PPG), a polypropylene glycol (PPG) derivative), or combinations thereof. Copolymers thereof (e.g. copolymers of ethylene glycol and propylene glycol), terpolymers thereof, and mixtures thereof, are also contemplated.

The organic polymer that may be used in the present disclosure include PEG, polylactate, polylactic acids, sugars, lipids, polyglutamic acid (PGA), polyglycolic acid, poly(lactic-co-glycolic acid) (PLGA), polyvinyl acetate (PVA), and the combinations thereof. The attachment of the organic polymer to polydopamine or the medical device may be accomplished by a covalent bond or non-covalent bond, such as by ionic bond, hydrogen bond, hydrophobic bond, coordination, adhesive, and physical absorption.

Polyether polymers may terminate with a hydroxyl group, or other end groups including, but not limited to, amino and thiol.

The linker (e.g., an organic polymer) may be linked to polydopamine through any suitable linkage/bond. Polydopamine may be functionalized with molecules containing thiols or primary amines via Michael addition or Schiff base formation, e.g., under very mild conditions (such as at neutral pH and/or room temperature).

Heterobifunctional organic polymer (e.g., PEG) chains may be created with amine and thiol functional groups combined with hydrazides, azides, cyclooctynes, and/or biotin. In one embodiment, PEG may be grafted to a surface of the medical device by physical adsorption or covalent bonding[81]. In another embodiment, amine-PEG-alkyne is immobilized on PDA-coated medical device followed by ligands (e.g., antibodies and/or antibody fragments) containing an azide functional group. In yet another embodiment, polydopamine may be linked to thiolated linker (e.g., thiolated organic polymer such as thiolated PEG), animated linker (e.g., animated organic polymer such as animated PEG), etc. Other functional groups for PEG to form linkages to a melanin, a melanin-like polymer, a synthetic version of melanin, or an aromatic catechol polymer (e.g., polydopamine or polymers of dopamine analogues), or to the ligands/biomolecules (e.g., antibodies and/or antibody fragments) include maleimide and alkene.

The organic polymer (e.g., a polyether derivative such as PEG) can have multiple functional groups for attachment to polydopamine, and for attachment to ligands (e.g., antibodies and/or antibody fragments). The medical device can have different types of functionalized organic polymers (e.g., polyether derivatives such as PEGs) bearing different functional groups that can be attached to multiple ligands (e.g., antibodies and/or antibody fragments). The organic polymer may be attached to polydopamine covalently or non-covalently.

In one embodiment, a functionalized-PEG-amine (either hydrazide or dibenzocyclooctyne (DBCO) functionalized) or animated PEG is used to link polydopamine. For example, a dibenzocyclooctyne surface is formed on a PDA-coated substrate or medical device by immersing the substrate or medical device in a solution of amino-PEG-DBCO.

In one embodiment, the organic polymer is bi-functionalized with amine and/or sulfhydryl groups.

Polyethylene Glycol (PEG)

PEG is a polyether compound, which in linear form has general formula $H[O-CH_2-CH_2]_n-OH$. Branched PEGs, including hyperbranched and dendritic PEGs are also contemplated and are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(-PEG-OH)_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; US 2003/0143596; WO 96/21469; and WO 93/21259 may also be used.

PEG may have an average molecular weight ranging from about 100 Daltons to about 20,000 Daltons, from about 200 Daltons to about 10,000 Daltons, from about 200 Daltons to about 5,000 Daltons, about 250 Daltons to about 8,000 Daltons, about 200 Daltons to about 6,000 Daltons, about 300 Daltons to about 5,000 Daltons, about 200 Daltons to about 400 Daltons, about 200 Daltons to about 300 Daltons, or about 500 Daltons to about 1,000 Daltons.

The coating may comprise two or more PEG molecules with different average molecular weights.

PEG, when immobilized on a substrate, may effectively prevent nonspecific binding of proteins to the substrate.

PEG may be functionalized with amine and/or thiol functional groups which can be reactive towards polydopamine coatings. Additionally, the PEG chains may be further modified to include hydrazides, azides, cyclooctynes, and/or biotin, etc., allowing PEG to conjugate with biomolecules. Examples of functionalized PEG are shown below.

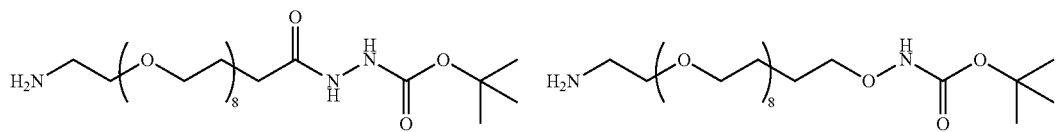

Hydrazide-PEG          Amino Oxy-PEG

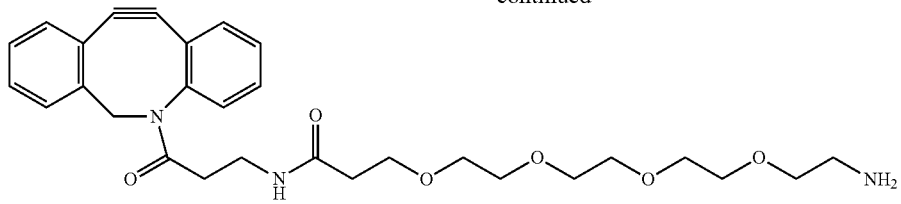

Combined with polydopamine functionalization, PEG may be deposited via a simple dip coating under mild conditions.

PEG has been shown to remain stable in the body for extended periods of time with minimal degradation. This stability limits inflammation due to microparticle formation and contributes to the materials overall biocompatibility.

Antibodies

The ligands (e.g., antibodies and/or antibody fragments) may be linked to a linker (e.g., an organic polymer) or polydopamine through any suitable linkage/bond. In one embodiment, the ligands (e.g., antibodies and/or antibody fragments) have exposed sugars so that they can be oxidized for binding the linker (e.g., an organic polymer) or polydopamine.

The coating of the medical device may further comprise antibodies, antibody fragments or combinations thereof. The antibodies, antibody fragments or combinations thereof may specifically bind to a cell surface antigen of endothelial progenitor cells or endothelial cells. In certain embodiments, the cell surface antigen is CD133, CD34, CD45, CD31, CD14, CDw90, CD117, HLA-DR, VEGFR-1, VEGFR-2, VEGFR-3, Muc-18 (CD146), Thy-1, Thy-2, CD130, CD30, stem cell antigen (Sca-1), stem cell factor 1 (SCF/c-Kit ligand), Tie-1, Tie-2, VE-cadherin, P1H12, TEK, CD31, Ang-1, Ang-2, HAD-DR, CD45, CD14, CD105, E-selectin, or combinations thereof. The cell surface antigen may be MHC such as H-2K$^k$ and HLA-DR.

In one embodiment, antibodies and/or antibody fragments that specifically bind to CD34, and/or CD133 are used. Hybridomas producing monoclonal antibodies directed against CD34 can be obtained from the American Type Tissue Collection (Rockville, Md.). In another embodiment, antibodies and/or antibody fragments that specifically bind to VEGFR-1 and VEGFR-2, CD133, or Tie-2 are used.

The antibodies, antibody fragments or combinations thereof may be monoclonal. The antibodies, antibody fragments or combinations thereof may be polyclonal. The antibodies, or antigen-binding portions thereof, include, but are not limited to, humanized antibodies, human antibodies, monoclonal antibodies, chimeric antibodies, polyclonal antibodies, recombinantly expressed antibodies, as well as antigen-binding portions of the foregoing.

An antigen-binding portion of an antibody may include a portion of an antibody that specifically binds to a cell surface antigen of endothelial progenitor cells or endothelial cells. The antibodies, antibody fragments or combinations thereof may comprise (consist of, or consist essentially of) Fab or F(ab')$_2$ fragments. The antibodies, antibody fragments or combinations thereof may specifically bind to the same cell surface antigen, or may bind to different cell surface antigens. In certain embodiments, the antibodies, antibody fragments or combinations thereof capture endothelial progenitor cells and/or endothelial cells in vivo when the medical device is implanted into a subject.

In certain embodiments, the antibodies, antibody fragments or combinations thereof comprise exposed sugars which can be oxidized for binding to the intermediate linker such as an organic polymer as described herein.

Also within the scope of the disclosure are antibodies or antigen-binding portions thereof in which specific amino acids have been substituted, deleted or added. These alternations do not have a substantial effect on the peptide's biological properties such as binding activity.

The present peptides may be the functionally active variant of antibodies of antigen-binding portions thereof disclosed herein, e.g., with less than about 30%, about 25%, about 20%, about 15%, about 10%, about 5% or about 1% amino acid residues substituted or deleted but retain essentially the same immunological properties including, but not limited to, binding to the cell surface antigen.

The antibodies or antigen-binding portions thereof may also include variants, analogs, orthologs, homologs and derivatives of peptides, that exhibit a biological activity, e.g., binding of an antigen such as a cell surface antigen. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

The antibody, or antigen-binding portion thereof, can be derivatized or linked to another functional molecule. For example, an antibody can be functionally linked (by chemical coupling, genetic fusion, noncovalent interaction, etc.) to one or more other molecular entities, such as another antibody, a detectable agent, an immunosuppressant, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. Cytotoxic agents may include radioactive isotopes, chemotherapeutic agents, and toxins such as enzymatically active toxins of bacterial, fungal, plant, or animal origin, and fragments thereof. Such cytotoxic agents can be coupled to the antibodies of the present disclosure using standard procedures, and used, for example, to treat a patient indicated for therapy with the antibody.

One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Useful detectable agents with which a protein can be derivatized (or labeled) include fluorescent agents, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin.

The present antibody or antibody fragment may be monoclonal, polyclonal, humanized, or chimeric antibody or a combination thereof.

The present antibody or antibody fragment may modulate adherence of circulating endothelial progenitor cells and/or endothelial cells to the medical device. The present antibody or antibody fragment may recognize and bind specifically to endothelial progenitor cells and/or endothelial cells surface antigens in the circulating blood so that the cells are immobilized on the surface of the device. The cell surface antigen may be vascular endothelial growth factor receptor-1, -2 and -3 (VEGFR-1, VEGFR-2 and VEGFR-3 and VEGFR receptor family isoforms), Tie-1, Tie2, CD34, Thy-1, Thy-2, Muc-18 (CD146), CD30, stem cell antigen-1 (Sca-1), stem cell factor (SCF or c-Kit ligand), CD133 antigen, VE-cadherin, P1H12, TEK, CD31, Ang-1, Ang-2, or an antigen expressed on the surface of endothelial progenitor cells and/or endothelial cells. In one embodiment, a single type of antibody and/or antibody fragment that reacts with one antigen can be used. Alternatively, a plurality of different types of antibodies and/or antibody fragments directed against different cell surface antigens can be used. In one embodiment, anti-CD34 and anti-CD133 antibodies and/or antibody fragments are used in combination.

As used herein, a "therapeutically effective amount of the antibody or antibody fragment" means the amount of an antibody that promotes adherence of endothelial progenitor cells and/or endothelial cells to the medical device.

The antibodies and/or antibody fragments may be immobilized on the medical device in an oriented manner, to ensure accessibility of the antibodies and/or antibody fragments to their antigens. For example, at least 1%, at least 3%, at least 5%, at least 8%, at least 10%, at least 15%, at least 20%, at least 25%, at least 30%, at least 35%, at least 40%, at least 45%, at least 50%, at least 60%, at least 70%, at least 80%, or at least 90%, of the antibodies and/or antibody fragments are available for binding to the cell surface antigen. In other words, at least 1%, at least 3%, at least 5%, at least 8%, at least 10%, at least 15%, at least 20%, at least 25%, at least 30%, at least 35%, at least 40%, at least 45%, at least 50%, at least 60%, at least 70%, at least 80%, or at least 90%, of the antigen-binding sites of the antibodies and/or antibody fragments are not blocked or denatured. For example, at least 1%, at least 3%, at least 5%, at least 8%, at least 10%, at least 15%, at least 20%, at least 25%, at least 30%, at least 35%, at least 40%, at least 45%, at least 50%, at least 60%, at least 70%, at least 80%, or at least 90%, of Fab regions of the antibodies and/or antibody fragments are fully exposed and available for antigen binding.

For example, the antibodies and/or antibody fragments may be immobilized on the medical device in an oriented manner, with the Fc domain fixed and the antigen-binding Fab domain fully exposed. In certain embodiments, as most antibodies possess at least one N-linked carbohydrate in the Fc region of the heavy chain, an immobilization strategy involves the modification of the oligosaccharides found in the Fc domain to introduce novel reactive moieties to the antibody structure. For example, there are two types of oligosaccharide modification that may be utilized for antibody modification. The first involves the oxidation of the oligosaccharides found in the Fc region to yield reactive aldehyde groups[103, 104]. After oxidation, the newly formed aldehyde moieties can be covalently conjugated to amine terminated surfaces[105,106]. Another technique that uses a mutated β1,4 galactosyltransferase enzyme to replace the native acetylglucosamine residues with a modified sugar. The modified sugar has a unique chemical handle incorporated into the molecular structure, often a ketone or azide. The incorporation of the modified sugar introduces an Fc specific target that can be used to immobilize the antibody. In the case of azide moieties, the antibody can be covalently conjugated to cyclooctyne bearing surfaces in an oriented manner via a catalyst free "click" cycloaddition reaction. By specifically modifying the Fc region of the antibody, both of these techniques provide covalent immobilization of the antibody with the Fab regions exposed (FIG. 1).

In one embodiment, an oxidation method is used to immobilize antibodies or antibody fragments. t-Boc-hydrazide-PEG-amine (Quanta Biodesign) is immobilized onto the PDA-coated surface of a substrate or medical device. For example, freshly prepared polydopamine-coated substrate/medical device is exposed to a t-Boc-hydrazide-PEG-amine in PBS/DMSO. The substrate/medical device is then rinsed with acetone, sonicated for 15 min in methanol, rinsed with acetone, and dried under a stream of nitrogen. After successful immobilization of the PEG chains, the modified surface is subjected to trifluoroacetic acid (TFA) in methylene chloride followed by a rinse in ammonium hydroxide to remove the tert-butyloxycarbonyl (t-Boc) protecting group and form a hydrazide-rich surface for additional immobilization. Antibodies or antibody fragments are oxidized to create the necessary aldehyde moieties (e.g., in the Fc region of the antibody). The antibodies or antibody fragments are dissolved in a buffer (e.g., PBS). Sodium m-periodate is added to the antibody solution, and the reaction allowed to proceed. After oxidation, the residual sodium m-periodate is removed using a desalting column (e.g., Sephadex G-25). The PEG functionalized material is then immersed in the oxidized antibody solution and allowed to react. Sodium cyanoborohydride is added to stabilize the Schiff base formed between the antibodies and the hydrazide rich coating.

Oxidation of the antibodies or antibody fragments may be carried out at a suitable pH, e.g., ranging from about pH 3 to about pH 7, from about 3.5 to about pH 6.8, from about pH 4 to about pH 6.5, from about 4.5 to about pH 6, from about pH 5 to about pH 6, from about 4 to about pH 6, about pH 5, about pH 5.5, about pH 5.6, about pH 5.8, or about pH 6.

In another embodiment, an enzyme method is used to immobilize antibodies or antibody fragments. Amino-PEG4-DBCO is immobilized onto the PDA-coated surface of a substrate or medical device. For example, freshly prepared polydopamine-coated substrate/medical device is exposed to an amino-PEG-dibenzocyclooctyne in PBS. The substrate/medical device is then rinsed with acetone, sonicated for 15 min in methanol, rinsed with acetone, and dried under a stream of nitrogen.

To functionalize antibodies or antibody fragments, DBCO reactive moieties may be created, e.g., at the Fc region of the antibody. Biomolecules (e.g., antibodies) can be modified using enzymatic methods to incorporate DBCO reactive moieties away from the active sites of the biomolecules (e.g., in the Fc region of an antibody). Step 1 may include removing terminal galactose residues from the biomolecules (e.g., antibodies or antibody fragments) (e.g., using β-1,4-galactosidase, 37° C., 16 hours), (β-1,4-galactosidase is a highly specific exoglycosidase that catalyzes the hydrolysis of β1-4 linked D-galactopyranosyl residues from oligosaccharides. This particular residue can be present in the Fc regions of a number of antibodies. After removal of the terminal galactose sugars, the biomolecules (e.g., antibodies or antibody fragments) may be combined with UDP-Gal-NAz to introduce the azide moiety. For example, step 2 may include incorporating GalNAz (e.g., Gal-T(Y289L), UDP-GalNAz, 37° C., 16 hours). In one embodiment, antibodies or antibody fragments may be modified using the Click-IT® GlcNAc Enzymatic Labeling System (Life Technologies Inc) as per the manufacturer's instructions. Briefly, the antibodies or antibody fragments are buffer exchanged into the pre-treatment buffer using a micro-spin column prepared with P30 resin (Bio-Rad, 1.5 mL bed volume). The antibodies or antibody fragments are then added to a pretreated column and centrifuged. The resultant antibody solution is supplemented with β-1,4-galactosidase and placed in an incubator at 37° C. A buffer exchange of the sample into Tris buffered saline (TBS) is performed using a micro-spin column prepared with P30 resin. After the buffer exchange, the antibody solution is combined with UDP-GalNAz, MnC12, and Gal-T(Y289L) and incubated at 30° C. After modification, the antibodies or antibody fragments are buffer exchanged into PBS. Finally, DBCO-coated substrate or medical device is immersed in the antibody solution, then washed with PBS to remove physically attached antibodies.

In still another embodiment, a UV immobilization technique is used to immobilize antibodies or antibody fragments. It may utilize indole-3-butyric acid-PEG to bind antibodies or antibody fragments via a conserved nucleotide binding site found on virtually all antibodies, regardless of isotype[183].

Antibody Fragments

The antibodies can be full-length or can include a fragment (or fragments) of the antibody having an antigen-binding portion, including, but not limited to, Fab, F(ab')2, Fab', F(ab)', Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present disclosure. Bird et al. Science, 1988, 242:423-426. Huston et al., Proc. Natl. Acad. Sci. USA, 1988, 85:5879-5883.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

Fv is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

Single-chain Fv or scFv antibody fragments comprise the $V_H$ and $V_L$ domains of antibody, where these domains are present in a single polypeptide chain. Generally, the scFv polypeptide further comprises a polypeptide linker between the $V_H$ and $V_L$ domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

Diabodies are antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, European Patent No. 404,097; PCT Publication WO 1993/01161; Hudson et al., Nat Med. 9:129-34, 2003; and Hollinger et al., Proc. Natl. Acad. Sci. USA 90:6444-8, 1993. Triabodies and tetrabodies are also described in Hudson et al., Nat. Med. 9:129-34, 2003.

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. Nat. Med. 9:129-134, 2003.

Various techniques have been developed for the production of antibody fragments. Traditionally, these fragments were derived via proteolytic digestion of intact antibodies (see, e.g., Morimoto et al., *J. Biochem. Biophys. Methods* 24:107-17, 1992; and Brennan et al., Science 229:81-3, 1985). However, these fragments can now be produced directly by recombinant host cells. Fab, Fv, and ScFv antibody fragments can all be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab')$_2$ fragments (Carter et al., *Bio/Technology* 10:163-7, 1992). In another approach, F(ab')$_2$ fragments are isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner.

The present antibody or antibody fragment may comprise at least one constant domain, such as, (a) an IgG constant domain; (b) an IgA constant domain, etc.

All antibody isotypes are encompassed by the present disclosure, including IgG (e.g., IgG1, IgG2, IgG3, IgG4), IgM, IgA (IgA1, IgA2), IgD or IgE. The antibodies or antibody fragments may be mammalian (e.g., mouse, human) antibodies or antibody fragments. The light chains of the antibody may be of kappa or lambda type. An alternative antibody can comprise sequences from more than one immunoglobulin class or isotype, and selecting particular constant domains to optimize desired effector functions is within the ordinary skill in the art.

The antibodies or antibody fragments of the present disclosure may be monospecific, bi-specific or multi-specific. Multi-specific or bi-specific antibodies or fragments thereof may be specific for different epitopes of one target polypeptide (e.g., a cell surface antigen) or may contain antigen-binding domains specific for more than one target polypeptide (e.g., antigen-binding domains specific for a cell surface antigen and other antigen, or specific for more than one cell surface antigens). In one embodiment, a multispecific antibody or antibody fragment comprises at least two different variable domains, wherein each variable domain is capable of specifically binding to a separate antigen or to a different epitope on the same antigen. Tutt et al., 1991, J. Immunol. 147:60-69. Kufer et al., 2004, Trends Biotechnol. 22:238-244. The present antibodies can be linked to or co-expressed with another functional molecule, e.g., another peptide or protein. For example, an antibody or antibody fragment can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for a cell surface antigen, and the other arm of the immunoglobulin is specific for a second therapeutic target (e.g., a different cell surface antigen, or another antigen) or is conjugated to a therapeutic moiety.

Generation of Antibodies

In one embodiment, the antibodies are monoclonal antibodies and may be produced according to the standard techniques of Kohler and Milstein (Continuous cultures of fused cells secreting antibody of predefined specificity. Nature 265:495-497, 1975, incorporated herein by reference), or can be obtained from commercial sources. Endothelial cells can be used as the immunogen to produce monoclonal antibodies directed against endothelial cell surface antigens.

For example, the monoclonal antibodies directed against endothelial cells may be prepared by injecting HUVEC or purified endothelial progenitor cells into a mouse or rat. After a sufficient time, the mouse is sacrificed and spleen cells are obtained. The spleen cells are immortalized by fusing them with myeloma cells or with lymphoma cells, generally in the presence of a non-ionic detergent, for example, polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity, i.e., reactivity with endothelial cell antigens.

Function Groups

The coating or substrate, and/or polydopamine, the linker, and/or the ligand (antibody or antibody fragment), can be modified by using known cross-linking agents to introduce surface functional groups. Crosslinking agents include, but are not limited to, divinyl benzene, ethylene glycol dimethacrylate, trimethylol propane trimethacrylate, N,N'-methylene-bis-acrylamide, alkyl ethers, sugars, peptides, DNA fragments, or other known functionally equivalent agents. The ligand may be conjugated to the coating or substrate by, for example, through coupling reactions using carbodiimide, carboxylates, esters, alcohols, carbamides, aldehydes, amines, sulfur oxides, nitrogen oxides, halides, or any other suitable compound known in the art. U.S. Pat. No. 6,268,222.

The surface of the coating or substrate, and/or polydopamine, the linker, and/or the ligand (antibody or antibody fragment), may be modified to incorporate at least one functional group. The organic polymer (e.g., PEG) may be modified to incorporate at least one functional group. For example, the functional group can be a maleimide or N-Hydroxysuccinimide (NHS) ester. The incorporation of the functional group makes it possible to attach various ligands, and/or pharmaceutical substances/therapeutic agents.

Click Chemistry

In order for the present coating or substrate to readily accommodate large ranges of ligands, the surface of the coating or substrate may be modified to incorporate a functional group. The coating or substrate may also be modified with organic polymers (e.g., PEGs) that can incorporate a functional group. In the meantime, the ligand, or therapeutic agent is modified to incorporate a functional group that is able to react with the functional group on the coating or substrate, or on the PEGs attached to the coating or substrate under suitable conditions. Accordingly, any ligand or therapeutic agent that has the reactive functional group is able to be readily conjugated to the coating or substrate. This generalizable approach is referred herein as "click chemistry", which would allow for a great deal of versatility. Any suitable reaction mechanism may be adapted for "click chemistry", so long as facile and controlled attachment of the ligand to the coating or substrate can be achieved. In one embodiment, a free triple bond is introduced onto PEG, which is already covalently conjugated with the coating or substrate. In the meantime, an azide bond is introduced onto the desired ligand. When the PEGylated coating or substrate and the ligand are mixed in the presence of a copper catalyst, cycloaddition of azide to the triple bond will occur, resulting in the conjugation of the ligand with the coating or substrate. In a second embodiment, a maleimide functional group and a thiol group may be introduced onto the coating or substrate and the desired ligand, with the coating or substrate having the maleimide functional group, the ligand having the thiol group, or vice versa. The double bond of maleimide readily reacts with the thiol group to form a stable carbon-sulfur bond. In a third embodiment, an activated ester functional group, e.g., a succinimidyl ester group, and an amine group may be introduced onto the coating or substrate and the desired ligand. The activated ester group readily reacts with the amine group to form a stable carbon-nitrogen amide bond.

Medical Devices

The medical device may be a device that is introduced temporarily or permanently into a mammal for the prophylaxis or therapy of a medical condition. These devices include any that are introduced subcutaneously, percutaneously or surgically to rest within an organ, tissue or lumen of an organ, such as arteries, veins, ventricles or atrium of the heart. Medical devices may include stents, stent grafts, covered stents such as those covered with polytetrafluoroethylene (PTFE), expanded polytetrafluoroethylene (ePTFE), uncoated stents, synthetic vascular grafts, catheters, artificial heart valves, artificial hearts and fixtures to connect the prosthetic organ to the vascular circulation, artificial venous valves, abdominal aortic aneurysm (AAA) grafts, inferior venal caval filters, permanent drug infusion catheters, embolic coils, embolic materials used in vascular embolization (e.g., cross-linked PVA hydrogel), vascular replacements, vascular sutures, vascular anastomosis fixtures, transmyocardial revascularization stents and/or other conduits.

The medical device can be any device that is implantable into a patient. For example, in one embodiment the device is for insertion into the lumen of a blood vessels or a hollowed organ, such as stents, stent grafts, heart valves, catheters, vascular prosthetic filters, artificial heart, external and internal left ventricular assist devices (LVADs), and synthetic vascular grafts.

The medical device can be any device used for implanting into an organ or body part comprising a lumen. The medical device may be implanted into the lumen of an organ or a blood vessel. The medical device can be, but is not limited to, a stent, a stent graft, a synthetic vascular graft, a heart valve, a catheter, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a sensor, a suture, a vascular anastomosis clip, an indwelling venous or arterial catheter, a vascular sheath and a drug delivery port.

The medical device may be a patent foramen ovale (PFO) closure device, a circulatory support device (e.g., a left ventricular assist devices (LVAD), an extracorporeal membrane oxygenation (ECMO) device, a neurovascular clip, a prosthetic joint, a vena cava filter, a component of an artificial heart, etc.

A stent may be any medical device which when inserted or implanted into the lumen of a vessel may expand the cross-sectional lumen of a vessel. Stents may be stainless steel stents, biodegradable stents, covered stents such as those covered with PTFE or ePTFE. In one embodiment, a stent is delivered percutaneously to treat coronary artery occlusions or to seal dissections or aneurysms of the splenic, carotid, iliac and popliteal vessels. In another embodiment, a stent is delivered into a venous vessel. The stent may comprise a polymeric and/or metallic structural element. Stents may comprise stainless steel, polymers, nickel-titanium, tantalum, gold, platinum-iridium, or Elgiloy and MP35N and other ferrous materials. A stent may be delivered through the body lumen on a catheter to the treatment site where the stent is released from the catheter, allowing the stent to expand into direct contact with the lumenal wall of the vessel. Stents include, but are not limited to, a metallic coronary stent, a metallic peripheral artery stent, a bioabsorbable peripheral stent, and a bioabsorbable coronary stent.

A synthetic graft may be any artificial prosthesis having biocompatible characteristics. In one embodiment, the synthetic graft can be made of polyethylene or polytetrafluoroethylene. In another embodiment, a synthetic graft comprises polyurethane, cross-linked PVA hydrogel, and/or biocompatible foams of hydrogels. In yet a third embodiment, a synthetic graft comprises an inner layer of meshed polycarbonate urethane and an outer layer of meshed polyethylene terephthalate. Synthetic grafts can be used for end-to-end, end to side, side to end, side to side or intraluminal and in anastomosis of vessels or for bypass of a diseased vessel segments, for example, as abdominal aortic aneurysm devices.

An artificial valve may be an artificial heart valve or an artificial venous valve. An artificial valve may be an artificial aortic valve, an artificial pulmonary valve, an artificial mitral valve, an artificial tricuspid valve, etc. Prosthetic heart valves (artificial heart valves) may include, but are not limited to, a transcatheter aortic valve (TAVR), a transcatheter mitral valve, a transcatheter tricuspid valve, a surgically implanted bioprosthetic aortic valve, a surgically implanted bioprosthetic mitral valves, a surgically implanted metallic mitral valve, and a surgically implanted metallic aortic valve.

Vascular replacements include, but are not limited to, endovascular aneurysm repair (or endovascular aortic repair) (EVAR), and ePTFE bypass graft material.

The medical device may a coronary medical device, including, but not limited to, a mitral clip, a tricuspid clip, an atrial appendage closure device, a pacemaker lead, an automated implantable cardioverter defibrillator (AICD) lead, a pacemaker box, and an automated implantable cardioverter defibrillator (AICD) box.

The medical device may have a luminal surface (or blood-contacting surface), and an outer surface (or abluminal surface or tissue-contacting surface). The present coating may be on the luminal surface (or blood-contacting surface), and/or the outer surface (or abluminal surface or tissue-contacting surface)

The present coating of the medical device may stimulate the development of an endothelial cell monolayer (confluent or sub-confluent) on the surface of the medical device, and/or modulate local chronic inflammatory response and other thromboembolic complications that result from blood vessel injury during implantation of the medical device.

The medical device can be made of numerous materials. The medical device may comprise stainless steel, Nitinol, MP35N, gold, tantalum, platinum or platinum iridium, or other biocompatible metals and/or alloys such as carbon or carbon fiber, cellulose acetate, cellulose nitrate, silicone, cross-linked polyvinyl acetate (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhidride, polyether sulfone, polycarbonate, polypropylene, high molecular weight polyethylene, polytetrafluoroethylene, or other biocompatible polymeric material, or mixture of copolymers thereof polyesters such as, polylactic acid, polyglycolic acid or copolymers thereof, a polyanhydride, polycaprolactone, polyhydroxybutyrate valerate or other biodegradable polymer, or mixtures or copolymers, extracellular matrix components, proteins, collagen, fibrin or other bioactive agent, or mixtures thereof.

For example, a stent can be made of stainless steel, Nitinol (NiTi), or chromium alloy and biodegradable materials. In one embodiment, the stent can be made from a biodegradable material. Synthetic vascular grafts can be made of a cross-linked PVA hydrogel, polytetrafluoroethylene (PTFE), expanded polytetrafluoroethylene (ePTFE), porous high density polyethylene (HDPE), polyurethane, and polyethylene terephthalate, or biodegradable materials such as polylactide polymers and polyglycolide polymers or copolymers thereof.

In one embodiment, the medical device can be a preserved blood vessel denuded or stripped of cells and can be from human, porcine or bovine origin. The preserved blood vessels form a scaffold suitable for, for example, as vascular graft segments.

The present method may be for treating a mammal with a vascular disease, the method comprising implanting a coated medical device into the patient's organ or vessel. Once in vivo, endothelial progenitor cells and/or endothelial cells are captured on the surface of the coated medical device by the recognition and binding of the cell surface antigens of the endothelial progenitor cells and/or endothelial cells by the antibody or antibody fragment present on the coating. Once the endothelial progenitor cells and/or endothelial cells are adhered to the medical device, they may grow and differentiate and form a confluent or sub-confluent, and functional endothelium on the blood-contacting surface of the medical device. Alternatively, or additionally, the medical device is coated with the endothelial progenitor cells and/or endothelial cells in vitro before implantation of the medical device. The endothelial progenitor cells and/or endothelial cells may be derived from progenitor cells, stem cells, and/or mature endothelial cells isolated from the patient's blood, bone marrow, or blood vessel. The presence of endothelial cells on the blood-contacting surface of the medical device may inhibit or reduce excessive intimal hyperplasia and/or thrombosis.

Human umbilical vein endothelial cells (HUVEC) may be obtained from umbilical cords according to the methods of Jaffe, et al., J. Clin. Invest., 52:2745-2757, 1973, incorporated herein by reference. Briefly, cells are stripped from the blood vessel walls by treatment with collagenase and cultured in gelatin-coated tissue culture flasks in MI99 medium containing low endotoxin fetal calf serum, preservative-free porcine heparin, endothelial cell growth supplement (ECGS) and glutamine.

Endothelial progenitor cells (EPCs) may be isolated from human peripheral blood according to the methods of Asahara et al. (Isolation of putative progenitor endothelial cells for angiogenesis. Science 275:964-967, 1997, incorporated herein by reference). Briefly, magnetic beads coated with antibody to CD34 are incubated with fractionated human peripheral blood. After incubation, bound cells are eluted and can be cultured in EBM-2 culture medium. Alternatively, enriched medium isolation can be used to isolate these cells. Briefly, peripheral venous blood is taken from healthy male volunteers and the mononuclear cell fraction is isolated by density gradient centrifugation, and the cells are plated on fibronectin coated culture slides in EC basal medium-2 (EBM-2) supplemented with fetal bovine serum, human VEGF-A, human fibroblast growth factor-2, human epidermal growth factor, insulin-like growth factor-1, and ascorbic acid. EPCs are grown for 7-days, with culture media changes every 48 hours. Cells may be characterized by fluorescent antibodies to CD133, CD45, CD34, CD31, VEGFR-2, Tie-2, and E-selectin.

Conditions to be Treated/Prevented

The present disclosure provides methods for treating, preventing (or treating prophylactically), or eradicating or ameliorating one or more of the symptoms associated with, a variety of diseases/conditions using the present medical device. Conditions to be treated or prevented include, but are not limited to, a vascular disease, such as restenosis, atherosclerosis, thrombosis, blood vessel obstruction (e.g., resulting from thrombosis), aneurysm and coronary artery disease; cancer; blood vessel remodeling; etc. In one embodiment, there is provided a method for retaining or sealing the medical device to the vessel wall, such as a stent or synthetic vascular graft, heart valve, abdominal aortic aneurysm devices and components thereof, and for establishing vascular homeostasis, thereby preventing excessive intimal hyperplasia as in restenosis.

The present medical device may decrease or inhibit tissue-based excessive intimal hyperplasia and restenosis by decreasing or inhibiting smooth muscle cell migration, smooth muscle cell differentiation, and/or collagen deposition along the inner luminal surface at the site of implantation of the medical device.

The present medical device and method can be used for any vessel such as any artery or vein. Included within the scope of the present disclosure is any artery including coronary, infrainguinal, aortoiliac, subclavian, mesenteric and renal arteries. The present medical device and method can be used for a peripheral artery, such as the femoral artery. Other types of vessel obstructions, such as those resulting from a dissecting aneurysm are also encompassed by the present disclosure. The present medical device and method may be used for any conduit or cavity in a mammal. The subjects that can be treated using the stent and devices of this invention are mammals, including a human, horse, dog, cat, pig, rodent, monkey and the like.

The present disclosure provides a method for treating a vascular disease in a mammal comprising implanting a medical device into the lumen of a vessel or tubular organ of the mammal, wherein the medical device is coated as described herein.

The present disclosure provides a method for recruiting cells to a blood-contacting surface of the medical device in vivo. In one embodiment, the method comprises implanting a medical device into a blood vessel of a subject. The medical device has a blood-contacting surface configured to bind target cells circulating in the blood of the subject. The target cells attached to the blood contacting surface proliferate and form functional endothelium in situ or self-endothelialize the surface of the device in restoring normal endothelium at the site of blood vessel injury. In one embodiment, the medical device can be biodegradable or can be coated with a biodegradable, biocompatible material. In this aspect, when implanted into a blood vessel, the biodegradable medical device may undergo in situ degradation and the neo-endothelium formed on the luminal surface of the device restores the blood vessel continuity through the injured site so as to form a functional neo-vessel.

Intimal hyperplasia may be the undesirable increase in smooth muscle cell proliferation and/or matrix deposition in the vessel wall. As used herein "restenosis" refers to the recurrent narrowing of the blood vessel lumen. Vessels may become obstructed because of restenosis. After PTCA or PTA, smooth muscle cells from the media and adventitia, which are not normally present in the intima, proliferate and migrate to the intima and secrete proteins, forming an accumulation of smooth muscle cells and matrix protein within the intima. This accumulation causes a narrowing of the lumen of the artery, reducing blood flow distal to the narrowing. As used herein, "inhibition or reduction of restenosis" refers to the inhibition or reduction of migration and/or proliferation of smooth muscle cells accompanied by prevention of protein secretion so as to prevent restenosis and the complications arising therefrom.

The present medical device may be administered to a subject (e.g., implanted into a subject) to achieve a therapeutic benefit ("treating") or prophylactically to achieve a prophylactic benefit ("preventing"). By therapeutic benefit is meant eradication or amelioration of a condition being treated, and/or eradication or amelioration of one or more of the symptoms associated with a condition. By prophylactic benefit is meant prevention or delay of the onset of a condition, and/or prevention or delay of the onset of one or more of the symptoms associated with a condition. In certain embodiments, administration (e.g., implantation) of the present medical device prevents a condition from developing or being exacerbated into more serious conditions.

"Treating" or "treatment" of a state, disorder or condition includes: (1) preventing or delaying the appearance of clinical symptoms of the state, disorder, or condition developing in a subject who may be afflicted with or predisposed to the state, disorder or condition but does not yet experience or display clinical symptoms of the state, disorder or condition: or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

Pharmaceutical Substances

The coating of the present device may comprise one or more pharmaceutical substances. The pharmaceutical substance may inhibit smooth muscle cell migration and/or proliferation, inhibit or reduce thrombus formation, promote endothelial cell growth and differentiation, and/or can inhibit or reduce restenosis after implantation of the medical device. The pharmaceutical substance may work downstream of the device to affect vessel properties or target solid organs. The medical device may exert local effects and/or systemic effects (e.g., distal to the device).

The pharmaceutical substance may be a vasodilator (such as prostacyclin (PG12), calcitonin gene-related peptide (α-CGRP), etc.).

The pharmaceutical substance may be effective in treating a vascular disease, such as artherosclerosis and restenosis. For example, the pharmaceutical substances include, but are not limited to, a cytotoxic or cytostatic agent, antiproliferatives, antineoplastics, antibiotics/antimicrobials, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, peptides, proteins, extracellular matrix components, vasodialators, thrombolytics, anti-metabolites, growth factor agonists, antimitotics, statins, steroids, steroidal and nonsterodial anti-inflammatory agents, angiotensin converting enzyme (ACE) inhibitors, free radical scavengers, PPAR-gamma agonists, anti-cancer chemotherapeutic agents such as aromatase inhibitors. Some of the aforementioned pharmaceutical substances include, for example, cyclosporins A (CSA), rapamycin, rapamycin derivatives, mycophenolic acid (MPA), retinoic acid, n-butyric acid, butyric acid derivatives, vitamin E, probucol, L-arginine-L-glutamate, everolimus, sirolimus, biolimus, biolimus A-9, paclitaxel, puerarin, platelet factor 4, basic fibroblast growth factor (bFGF), fibronectin, simvastatin, fluvastatin, dihydroepiandrosterone (DHEA)) and 17beta-estradiol.

Examples of pharmaceutical substances which can be incorporated in the coating, also include, but are not limited to, prostacyclin, prostacyclin analogs, alpha-CGRP, alpha-CGRP analogs or alpha-CGRP receptor agonists: prazosin; monocyte chemoattactant protein-1 (MCP-1); immunosuppressant drugs such as rapamycin, drugs which inhibit smooth muscle cell migration and/or proliferation, anti-thrombotic drugs such as thrombin inhibitors, immunomodulators such as platelet factor 4 and CXC-chemokine; inhibitors of the CX3CR1 receptor family; anti-inflammatory drugs, steroids such as dihydroepiandrosterone (DHEA), testosterone, estrogens such as 17.beta.-estradiol; statins such as simvastatin and fluvastatin; PPAR-alpha ligands such as fenofibrate and other lipid-lowering drugs, PPAR-delta and PPAR-gamma agonists such as rosglitazone; nuclear factors such as NF-κB, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angionesis inhibitor compound; peptides or antibodies which inhibit mature leukocyte adhesion, antibiotics/antimicrobials, and other substances such as tachykinins, neurokinins or sialokinins, tachykinin NK receptor agonists: PDGF receptor inhibitors such as MLN-518 and derivatives thereof, butyric acid and butyric acid derivatives puerarin, fibronectin, erythropoietin, darbepotin, serine proteinase-1 (SERP-1) and the like. The aforementioned pharmaceutical substances can be applied to the coating on the device alone or in combinations and/or mixtures thereof.

Prostacyclin (PG12) is an autocrine and paracrine mediator that binds to the specific G protein-coupled receptor, IP receptor and/or to the nuclear receptor, peroxisome proliferators-activated receptor (PPAR) δ. Following its synthesis and release, prostacyclin exerts local anticoagulant and vasodilator properties, is not stored, and is rapidly converted by non-enzymatic processes to an inactive metabolite, 6-keto prostaglandin F1α (PGF1α). Prostacyclin causes relaxation of vascular smooth muscle predominantly via the adenylyl cyclase/cyclic-AMP transduction system and causes vasodilation of all vascular beds studied. Stable prostacyclin analogues may be used in the present coating and methods.

Calcitonin gene-related peptide (α-CGRP) can stimulate vasodilation in the absence of endothelium-derived NO. Vasodilatation may be mediated via the CGRP1 receptor.

The pharmaceutical substance may be released locally into the adjacent or surrounding tissue in a slow or controlled-release manner. The pharmaceutical substance may have therapeutic effects locally and/or systemically.

Combination Therapy

The present medical device can be administered/implanted alone or in combination with one or more other therapies, such as surgery, another medical device, and/or another therapeutic agents (e.g., a second therapeutic agent).

Such combination therapy can have an additive or synergistic effect on condition parameters (e.g., severity of a symptom, the number of symptoms, or frequency of relapse).

The present medical device may be administered/implanted concurrently with the second therapy. In another specific embodiment the second therapy is administered prior or subsequent to administration/implantation of the present medical device.

In some embodiments, the second therapeutic agent is a cytotoxic agent which may be a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin, rhizoxin, and palytoxin can be used.

The subjects that can be treated using the medical device, methods and compositions of this invention are mammals, and include a human, horse, dog, cat, pig, rodent, monkey and the like.

The following are examples of the present disclosure and are not to be construed as limiting.

Example 1 Preclinical Assessment of Orthotopic Prosthetic Aortic Valve Implantation Animal Model Experimental evaluation will be performed on 6 adult Yorkshire swine (~60 kg) after institutional review board approval. The animals will be fasted ~12 hours prior to the induction of anesthesia. The pigs will be pre-medicated via IM injection with an anesthetic cocktail containing Ketamine, Xylazine and Atropine. Pigs will be transported to the pre-operative room of the Vivarium, where anesthesia will be induced via face mask using 5% isoflurane with 70% nitrous oxide/oxygen. Once anesthetized, an IV catheter will be placed in an ear vein. Once IV access has been achieved, the pigs will be intubated and placed on a ventilator for the remainder of the procedure. The pigs will then be transferred to the operating suites of the Vivarium, where the pigs will be maintained at surgical plane of anesthesia with ~2-3% isoflurane with 70% nitrous oxide/oxygen and monitored (EKG, Pulse ox, jaw tone etc) throughout the procedure. Once the animal is at a surgical plane of anesthesia (confirmed by the absence of the jaw tone reflex, and stable parameters on the EKG) the surgical procedure will be performed.

Surgical Procedure

Valve implantations will be performed in a sterile setting with full anaesthesiological, surgical and angiographic equipment. The setup will include a monoplane fluoroscopic angiography system (Siemens, Munich, Germany) and a transthoracic echocardiographic console (GE E95s). Fluoroscopic, angiographic, and echocardiographic imaging of the aortic root during the procedure will be performed prior to implantation to obtain an optimal perpendicular view of the implantation site. The distance of the left and right coronary ostia from the aortic annulus in relation to the THV frame height will be determined. In addition, a pigtail-catheter will be placed deep within the right coronary sinus to further facilitate positioning by providing a reliable landmark for correct alignment of the aortic valve prosthesis, and a pacemaker lead will be positioned in the right ventricle.

Devices 23 mm Edwards SAPIEN valves will be used, 3 as supplied by the manufacturer, and 3 that have been coated with the endothelial progenitor cell capture coating as described herein (e.g., a coating comprising polydopamine, or polydopamine plus antibodies, or polydopamine, PEG plus antibodies). The Edwards SAPIEN 3 Transcatheter Heart Valve (THV) is comprised of a balloon-expandable, radiopaque, cobalt-chromium frame, trileaflet bovine pericardial tissue valve, and polyethylene terephthalate (PET) fabric skirt. The Edwards Commander delivery system consists of a Flex Catheter to aid in valve alignment to the balloon, tracking, and positioning of the THV. The handle contains a Flex Wheel to control flexing of the Flex Catheter, and a Balloon Lock and Fine Adjustment Wheel to facilitate valve alignment and positioning of the valve within the native annulus. The Balloon Catheter has radiopaque Valve Alignment Markers defining the working length of the balloon. A radiopaque Center Marker in the balloon is provided to help with valve positioning. A radiopaque Triple Marker proximal to the balloon indicates the Flex Catheter position during deployment.

A 14F expandable introducer sheath will be surgically inserted into the common femoral artery for the transfemoral approach and into the subclavian artery for the transsubclavian approach. The delivery catheter will be advanced over an Amplatz extra stiff 0.035-inch guidewire (Cook, Inc., Bloomington, Ind.) into the left ventricle. Accurate positioning of the THV will be ascertained by aortic root angiograms with a pigtail catheter and by transthoracic echocardiographic (TTE) guidance. Final deployment position will be documented by aortic root angiography and TTE. Rapid pacing will then be commenced and once systolic blood pressure has decreased to 50 mmHg or below, the balloon will be inflated. Once the barrel of the inflation device is empty, the balloon will be deflated. When the balloon catheter has been completely deflated, the pacemaker will be turned off.

Follow-Up

At 7 and 14 days, assessment of the valve will be performed by transthoracic echocardiography after the induction of general anesthesia. After the 14-day echocardiographic assessment, the animals will be sacrificed by lethal injection, and the prosthetic TAVR valves explanted for gross inspection and histologic and scanning electron microscopic assessment of the valve leaflets. Important parameters to be assessed will include the presence of gross and microscopic thrombi, and degree of coverage of the valve leaflets with endothelium.

Procedural Considerations

Aortic valve sizing in preclinical studies requires a different strategy than typically used in human clinical cases. In the clinic, valves being replaced are diseased and typically have a rigid/calcified annulus; while in the animal model, they are healthy. A healthy annulus is malleable and tends to dilate upon waking from anesthesia; so valves in the animal model need to be appropriately oversized to avoid migration and stability issues. However, too much oversizing can cause an increase in other complications such as fatal arrhythmias, which have been seen preclinically and reported in human clinical studies. In addition to the initial annulus size, it is important to keep in mind the growth of the animal (and annulus) over the timeframe of the study. If the growth of the annulus exceeds the dimensions of the prosthetic valve, large paravalvular leaks can occur, causing complications in the later stages of the study.

Mitigation strategy—Adult swine (60 kg) will be used for these studies, minimizing annulus growth.

The studies will be sub-acute (up to 14 days). The sheep model is more commonly selected as selected for chronic valve evaluation due to moderate weight and size increase during follow-up, limiting the risk of paravalvular leak due to mismatch.

Transcatheter delivery of prosthetic valves has introduced new challenges in the animal model. Not only does the size of the annulus and proper valve oversizing need to be considered, but the diameter of the peripheral vessel used for vascular access and delivery has to be of suitable size. If the animal's annulus is within the target dimensions but the catheter profile is too large to fit through the peripheral vascular, vessel complications may result or the valve may not be able to be delivered.

Mitigation strategy—Adult swine (60 kg) will be used for these studies, minimizing annulus growth.

In addition to annulus size and peripheral artery diameters, the dimensions of the ascending aorta and location of other vascular structures also impact the success of the TAVR implant and study. In the animal model, the length of the ascending aorta has a direct impact on the success of higher-profile implants.

Mitigation strategy—In contrast to sheep that tend to have the brachiocephalic artery that originates off the ascending aorta, the pig's brachiocephalic artery originates at the arch of the aorta, yielding a longer ascending aorta, which permits implants to sit correctly in the annulus.

Occlusion of the left main coronary artery, and ultimately heart bloc, can be a common complication in TAVR preclinical studies within pig models. Swine have coronary ostia that originate close to the aortic valve. This differs from humans where the coronary arteries originate further away from aortic annulus. With the shorter distance between the aortic annulus and the coronary ostia in the animal model, there is a higher tendency to occlude the coronary ostia.

Example 2 Development of a Universal Coating Method for Oriented-Antibody Immobilization on the Surface of Implantable Materials Objectives: Surface endothelialization of implanted endovascular devices leads to speedy heal and reduced thrombogenicity. We have developed the Genous technology-Dextran mediated coating of anti-human CD34 antibodies on the stent that can capture circulating endothelial progenitors for enhanced endothelialization. This method, however fails to coat other materials such as ePTFE. The goal of this study was to develop a universal coating method that can be used for immobilization of anti-CD34 antibodies on the surface of a variety of materials.

Methods: The polydopamine film was formed via the oxidative self-polymerization of dopamine under slightly basic conditions on the surface of a variety of materials, i.e., metal stents, ePTFE grafts and pig pericardium. Subsequently, the polyethylene glycol (PEG) crosslinker was applied, which conjugated with the polydopamine coating at one end, and at the other end bound the Fc fragment of antibodies. The coating layer was analyzed using the profilometer, X-Ray photoelectron spectroscopy and scanning electron microscopy. The functionality of CD34 antibody coated surface was assessed by cell binding assay.

Results: The CD34 antibody-coated surface of different materials bound CD34+ cells but did not bind CD34− cells. The surfaces without antibodies but functionalized with polydopamine and PEG did not bind CD34+ cells. The thickness of coating layer was within the micrometer range, and the surface was homogeneous and smooth.

Conclusions: A universal coating method for oriented antibody immobilization was developed, which can be applied for the purpose of thrombogenicity reduction in bioprothetic and mechanical valves, as well as ePTFE grafts.

Example 3 Surface Modification of Implantable Materials for Novel Therapeutic Applications Objectives To develop a means for the immobilization of biomolecules that can be applied to a wide range of solid surfaces and to test the effectiveness of the coating by developing novel antibody functionalized vascular prostheses.

To demonstrate the potential of antibody functionalized materials as a novel platform for local drug delivery.

Study 1

We hypothesize that a polydopamine (PDA) surface modification in combination with an appropriately functionalized polyethylene glycol layer will produce a universal platform to immobilize bioactive molecules on a wide range of biomedical materials.

Background—Biomolecule Immobilization

Current Immobilization Techniques

Most standard biomaterials are produced from inert substances lacking functional moieties for chemical conjugation: therefore, non-covalent physical adsorption is a commonly used method for biomolecule immobilization. This technique however, results in randomly distributed molecules, loss of bioactivity, and coatings that can be easily removed from a material's surface. An alternative method that provides more reliable results involves the introduction of novel chemical moieties for covalent immobilization through chemical, plasma, or gamma ray treatment. These techniques have been used to immobilize biomolecules such as fibronectin, collagen, gelatin, and RGD[66], but unfortunately they still often result in randomly distributed and inactive molecules. Additionally, these techniques have limited penetration depth, can negatively affect the mechanical properties of the material[67], and cannot be used universally on all substrates. It is therefore desirable to develop a method for surface functionalization that effectively covers the surface, maintains the mechanical properties of the substrate and can be applied to a wide range of materials.

Polydopamine Films

Polymeric coatings have been utilized in a number of applications to effectively control surface properties[68-70]. Recently, thin polymer films assembled through the sequential deposition of interacting polymers, known as layer-by-layer (LbL) deposition, have shown promise as surface modifiers providing desirable traits such as capacity for drug loading and potential for modification with biomolecules. Unfortunately, most LbL deposition techniques suffer from the same issues described above, involving multiple steps and requiring complex initial surface modifications.

A new form of LbL deposition, that has recently attracted a great deal of interest, overcomes these issues by utilizing the spontaneous formation of PDA films to functionalize materials. PDA films are synthetic eumelanin polymers formed via the oxidative self-polymerization of dopamine (DA) under slightly basic conditions. These films have the ability to form onto virtually any solid surface. This unique property allows for the formation of thin, functionalizing films on a wide range of materials simply by immersing the substrate in an aqueous DA solution. Work by Lee et al. confirmed the presence of PDA films on a multitude of different materials after a simple dip coating. Examples of these materials include metals, glass and synthetic polymers (PTFE and PDMS)[71]. X-ray photoelectron spectroscopy (XPS) of 25 materials after a 3-hour immersion revealed the complete absence of substrate specific signals, implying a cohesive coating thickness of at least 10 nm.

In addition to the universal and facile nature of the deposition process, PDA coatings have been found to be an extremely versatile platform for secondary reactions. The films can be functionalized with molecules containing thiols or primary amines via Michael addition or Schiff base formation under very mild conditions (at neutral pH and room temperature). Previous work has utilized the reactivity of PDA-coated substrates to immobilize thiolated polyethylene glycol (PEG), aminated-PEG, trypsin, bovine serum albumin (BSA), concanavalin A, RNase B, and several antibodies. In most cases where biomolecules were directly immobilized, bioactivity was maintained[72].

Polyethylene Glycol Cross Linkers

A major factor that influences the biocompatibility of a material is its ability to resist fouling (non-specific protein and cell adhesion). PEG is a hydrophilic polyether compound that has found a wide range of applications in both medicine and industry for its excellent biocompatibility and anti-fouling properties[73]. Modification of a surface with hydrophilic polymer chains has been shown to decrease protein adsorption and drastically reduce non-specific cell adhesion[74-77]. A number of techniques are currently used to modify surfaces with PEG including physical adsorption, self-assembled monolayers, chemical coupling, and graft polymerization. Investigations examining the antifouling properties of PEG have shown that it can effectively prevent nonspecific binding on a number of substrates. Chen et al. demonstrated that PEG films could be formed on polyaniline surfaces and showed a significant reduction in both protein adsorption and platelet adhesion[78]. Zhang et al. showed that a PEG coating formed on SS was very effective in preventing bovine serum albumin and gamma-globulin adsorption[79]. PEG chains were used by Wang et al. to modify PTFE surfaces and demonstrated that the PEG modified PTFE showed increased hydrophilicity and was very effective in preventing bovine serum albumin adsorption[80].

In addition to its excellent antifouling properties, PEG has also been utilized as a crosslinking molecule for peptide modification A growing catalogue of functionalities allows PEG to form conjugates with virtually any biomolecule. Heterobifunctional PEG chains have been created with amine and thiol functional groups combined with hydrazides, azides, cyclooctynes, and biotin. The versatility and widespread use of PEG chains for biomolecule modification make them an attractive tool to expand the functionality of PDA coated materials. Zeng et al. demonstrated that with a PDA intermediate coating. PEG could be grafted to a surface with the ease of physical adsorption and the stability of covalent bonding[81]. Proks et al. showed that PEG could be used for both antifouling and as a crosslinking agent[82]. They immobilized amine-PEG-alkyne on PDA coated silicon wafers followed by synthetic peptides containing an azide functional group. After peptide immobilization, the surfaces showed improved binding of target cells and maintained repulsive properties towards non-specific proteins[82]. Combined with biologically active molecules, PEG modification has the exciting potential to provide new bioactive materials.

Current Techniques for Antibody Immobilization

Effective immobilization of antibodies onto surfaces has the potential to improve the development of biosensors, bioanalytical technologies, and biomedical devices[83,84]. Non-covalent fixation techniques are common methods for the immobilization of antibodies to inert surfaces, either through physical adsorption[85-91], or through entrapment of the antibody within a coating matrix. Though these techniques successfully immobilize the antibody on the surface, they result in randomly oriented antibody molecules with up to 90% of the antibodies left inactive due to blocking of the antigen binding sites[92-94]. Using an entrapment method, we have shown biologically active antibody immobilization in a porcine model using a Dextran coating. This method creates a blend of dextran and the desired antibody, the dextran-antibody mixture is then applied to the substrate using plasma reactor technology creating a coating with a fraction of antigen binding sites exposed. This method has demonstrated successful capture of CD34 positive cells[63]. However, when this coating was used to immobilize an alternative antibody (H-2$K^k$), the immunobinding activity of the surface was very poor. Although the presence of imbedded antibody could be demonstrated on dextran/antibody coated SS disks, the surfaces failed to capture H-2$K^k$ expressing EPCs. The lack of effective cell capture is likely due to a combination of non-oriented antibody immobilization (with many of the anti-H-2$K^k$ antibody Fab domains buried in the dextran), and antibody denaturing. Similarly, when applied to ePTFE graft material, the dextran/anti-CD34 coating was ineffective in binding circulating EPCs in two different porcine AV-shunt models[95,96]. These results indicate that the dextran coating, while effective in specific cases, does not provide a universal method of antibody immobilization.

An alternate immobilization method involves nonspecific-targeted chemical immobilization (FIG. 1). This method utilizes functionalized surfaces that react to the exposed amino acid side chains of antibodies. One limitation of this method is that it is not possible to control whether the antibody binds via Fab region side chains or those of the Fc region. Although specific functional groups are targeted, the antibody orientation is still random. As with physical methods, this results in denaturation of the antibodies and loss of immunobinding activity[97-100]. These nonspecific techniques have shown some promise but as with the physical methods described above, they are only effective in specific cases and no one method is applicable to all surfaces. It is therefore desirable to develop a new immobilization method that is applicable to many different surfaces and affixes antibodies in an oriented manner, with the Fab regions fully exposed and available for antigen binding.

Oriented Antibody Immobilization

As described, immobilization processes can often block binding sites or denature antibodies, leading to partial or complete loss of immunobinding ability[101]. A technique to overcome this problem involves immobilizing antibodies in an oriented manner, with the Fc domain fixed and the antigen-binding Fab domain fully exposed[102]. It has been well established that most antibodies possess at least one N-linked carbohydrate in the Fc region of the heavy chain. As such, an immobilization strategy that is gaining popularity involves the modification of the oligosaccharides found in the Fc domain to introduce novel reactive moieties to the antibody structure. There are two types of oligosaccharide modification that have been increasingly utilized for antibody modification. The first involves the oxidation of the oligosaccharides found in the Fc region to yield reactive aldehyde groups[103, 104]. After oxidation, the newly formed aldehyde moieties can be covalently conjugated to amine terminated surfaces[105,106]. Another technique that has recently been described uses a mutated β1,4 galactosyltransferase enzyme to replace the native acetylglucosamine residues with a modified sugar. The modified sugar has a unique chemical handle incorporated into the molecular structure, often a ketone or azide. The incorporation of the modified sugar introduces an Fc specific target that can be used to immobilize the antibody. In the case of azide moieties, the antibody can be covalently conjugated to cyclooctyne bearing surfaces in an oriented manner via a catalyst free "click" cycloaddition reaction. By specifically modifying the Fc region of the antibody, both of these techniques provide covalent immobilization of the antibody with the Fab regions exposed (FIG. 1).

Work by Yuan et al.[107] demonstrated the effectiveness of oligosaccharide oxidation by successfully immobilizing anti-CD34 antibodies on SS slides. They produced an amine rich surface using 3-Aminopropyltriethoxysilane as a crosslinking molecule, and the functionalized SS was immersed into the oxidized antibody solution. The oriented antibodies retained their immunobinding ability and exhibited a 3-fold increase in cell capture efficiency when compared with a conventional immobilization strategy (glutaraldehyde)[107]. Kang et al.[108] further explored this method of immobilization by fixing anti-mouse IgG antibodies onto magnetic microparticles. Again an amine rich surface was created, and a hydrazide coating was formed on the magnetic particles. Hydrazides have the benefit of reacting with aldehydes at lower pHs thereby preventing non-specific cross-linking between the amine residues on the antibody and the newly formed aldehydes. The oriented antibodies showed a 2-fold improvement in immunobinding efficacy over amine coupling (N-hydroxysuccinimide)[108].

Though it is still a relatively new technology, the enzymatic introduction of unique chemical moieties to the Fc region has also produced impressive results. Boeggeman et al. utilized this technique to functionalize several monoclonal antibodies (mAb) with either biotin or fluorescent molecules. They first removed sugars found in the heavy chain region of the antibody using β1,4 galactosidase from *Streptococcus pneumonia*, exposing the terminal N-acetylglucosamine residues. They then introduced a modified sugar bearing a ketone chemical handle using a mutant β1,4 galactosyltransferase (β1,4-Gal-T1-Y289L) enzyme. The modified antibodies were then reacted with either aminooxy functionalized Alexa 488 or biotin. Their results indicated that not only were the desired molecules (Alexa 488 and biotin) successfully incorporated into the antibody structure, but also that the linking of the desired molecule to the mAb via the N-linked carbohydrates did not modify the antibody's affinity for the antigen[109]. Zeglis et al. utilized a similar technique for the radiolabeling of a prostate antigen-targeting antibody (J591). Again they first removed the sugars found in the heavy chain region of the antibody using β1,4 galactosidase, exposing terminal N-acetylglucosamine residues. They then utilized the same mutated enzyme (β1,4-Gal-T1-Y289L) to incorporate azide-modified sugars into the Fc region of the antibody. The azide-functionalized antibodies were then reacted with desferrioxamine-modified dibenzocyclooctynes via a catalyst-free "click" conjugation. Finally the chelator modified antibodies were radiolabeled with $^{89}$Zr. Their results indicated that $^{89}$Zr was successfully bound to the Fc region of the antibody, and that its incorporation into the antibody structure did not affect the antibody's affinity for its antigen[110].

Research Design

Polydopamine Film

PDA anchors will be used for the initial functionalization of all materials. A dopamine HCl (dopamine hydrochloride, Sigma-Aldrich) solution (2 mg/ml) will be prepared in 10 mM Tris-HCl (pH 8.5). The substrate (SS, CoCr, electrospun polyurethane, and ePTFE graft material) will be immersed in the solution for 24 h in a dark environment. After the reaction, the material will be removed, thoroughly rinsed, and dried in a pure nitrogen stream[111,112]. We have been able to successfully deposit PDA films onto 316L SS and CoCr disks, ePTFE graft material, as well as coronary stents. These results together with those described by Lee et al.[71] indicate that this functionalization method is viable and can be applied to common cardiovascular platforms. The reactivity of the PDA films has been demonstrated by the creation of a variety of preliminary bioactive surfaces through the immobilization of biomolecules (BSA and Avidin) on the PDA coated material. Simple immersion of the coated SS substrates in a 2% BSA solution created an antifouling surface that effectively inhibited cell adhesion. PDA coated SS and COCR substrates exposed to an avidin solution exhibited capture of biotinylated fluoroescent molecules.

Polyethylene Glycol Functionalization

For the formation of the polyethylene glycol crosslinking layer, a functionalized-PEG-amine (either hydrazide or dibenzocyclooctyne (DBCO) functionalized) solution (25 mg/mL) will be prepared in phosphate buffered saline (PBS, pH 7.4). The pH of the solution will be adjusted to 8.6 and the PDA coated material will be immersed for 30 h at 50° C. The material will then be rinsed thoroughly and dried in a pure nitrogen stream[113]. We have been able to immobilize animated PEG chains onto PDA functionalized material. A dibenzocyclooctyne surface was formed on PDA coated SS and CoCr by immersing the substrates in a solution of amino-PEG4-DBCO. The DBCO surface exhibited effective capture of azide functionalized fluorescent molecules (FIG. 9).

Biocompatibility Assessment

Biocompatibility testing will be performed in accordance with International Standard ISO 10993 guidelines for the preclinical evaluation of biomedical devices[114-117]; 60 New Zealand White rabbits will be used. The rabbits wall be sedated with an intramuscular injection of ketamine (40 mg/kg) and xylazine (5 mg/kg). The fur along the spinal column will be clipped to expose an area of approximately 10 cm². The skin will be disinfected using isopropyl alcohol and painted with a Betadine solution. A single incision, approximately 8 cm long, will be made along the mid-line of the back, to expose the paravertebral muscle. The muscle will be incised ~1 cm parallel to the fiber axis, and a small pocket will be created. Hemostasis will be achieved by the application of direct pressure. Four pieces (5×5 mm) of coated test material (SS, CoCr, electrospun polyurethane, ePTFE) and 4 uncoated controls will be implanted into the left and right paravertebral muscles in a random fashion, at least 1 cm apart (4 per side). The muscle incision, subcutaneous tissue, and fascia will be closed with absorbable sutures and the skin incision will be closed with non-absorbable sutures or skin staples. The animals will be sacrificed by lethal intravenous injection of pentobarbital after 1, 7, 14 and 28 days, as well as at 12 weeks. The implantation sites will be exposed, and inspected for signs of hemorrhage, necrosis, fluid accumulation, discoloration, infection or encapsulation. Tissue from the implantation sites will be harvested and fixed in 10% neutral buffered formalin. The final tissue analysis will be based on gross and histopathological data. We have extensive experience with this model and have used it to evaluate various stent platforms and coatings as well as ePTFE and bioabsorbable stent material.

Validation of Surface Coating

The US Food and Drug Administration (FDA) has recently provided guidance to the intravascular device industry to evaluate the safety and efficacy of coated devices[118]. Characteristics such as adhesion, barrier effectiveness, and stability of the coating need to be assessed. Surface coating thickness: It has been well established that the thickness of a vascular stent strut is directly related to the degree of neoinitmal hyperplasia seen at follow up[119]. Therefore, it is important that the coating thickness be determined. Coaled substrates (316L SS, CoCr, electrospun polyurethane, ePTFE) will be analyzed using contact profilometry (KLA Tencor P16+, Surface Interface (SI) Ontario, University of Toronto). The various materials will be coated such that only one half of the surface is covered. The samples will then be analyzed using the profilometer and the difference in height between the coated and uncoated halves will be compared. The prolifometer will be operated by the SI Ontario staff using their standard protocols. All data analysis will be performed on site with guidance from SI Ontario staff. This technique will also provide information on surface topography (roughness).

Surface Coating Homogeneity, Confluence and Barrier Effectiveness

Scanning Electron Microscopy (SEM): The surface topography, integrity and confluence of the coated surfaces will be assessed by SEM. For SEM study, samples (316L SS, CoCr, electrospun polyurethane, ePTFE) will be prepared with standard dehydration and 20 nm gold sputter coating techniques. A scanning electron microscope (Philips XL-30 series, Netherlands) will be used.

X-Ray photoelectron spectroscopy (XPS): XPS is a quantitative spectroscopic test that calculates the empirical formula, chemical state and electronic state of elements on a material surface. Spectra are obtained by measuring the kinetic energy and number of electrons that escape from the top 1-10 nm of the surface with X-ray irradiation. XPS will be conducted with coated samples of 316L SS, CoCr, electrospun polyurethane, and ePTFE on a K-Alpha XPS instrument (Thermo Scientific) equipped with a monochromatic Al Kα X-ray source (SI Ontario)). The X-Ray source will be operated by SI Ontario staff using their standard protocols (detection angle of 45°, Kα line of a standard aluminum x-ray source operated at 300 W). The thickness, homogeneity, confluence and integrity of the surface coating can be assessed by XPS. In the case of non-confluence, signals from metallic compounds from the substrate will appear. It has been shown that XPS is more sensitive than SEM to assess coating integrity and coherence[120].

Surface coating adhesion and cohesion after deformation: Plastic deformation occurs in Critical parts of a stent depending on stent design and material[121-126]. According to finite element modeling, this plastic deformation could be up to 25%[126].

SEM: The adherence and deformability of the PDA coated surfaces (316L SS stents, CoCr stents, electrospun polyurethane covered stents (PK-Papyrus Stent, Biotronik, Germany), ePTFE covered stents (Jostent Graftmaster™, Abbott Vascular, Ill.), will be assessed by scanning electron microscopy before and after balloon expansion. Three of each device will be mounted onto standard angioplasty balloons for expansion. The expanded stents will be examined using SEM for any evidence of cracking, flaking or peeling. Luo et al have recently reported that PDA films are resistant to the deformation of compression and expansion of vascular stents using similar techniques[127]. To evaluate the stability of the PDA films, the surface microstructure of the coating will be examined using SEM before and after immersion in 37° C. PBS for 7, 15 and 30 days for any evidence of swelling or peeling.

XPS: Coated 316L SS and CoCr disks, 1 cm in diameter and 0.5 mm in thickness will be plastically deformed up to 25% using a punch test device mounted on a SATEC 3340 testing system (Instron, Norwood, Mass.—on loan from OrbusNeich Medical Technologies, FL). All deformations will be performed at room temperature at a displacement rate of 0.05 mm/s and a maximal load of 2200N to obtain 25% deformation as described by Lewis et a[128,129]. The adhesion and cohesion of the surface coating will be determined by spectral analysis as described above.

Surface hydrophilicity and surface energy: The water contact angle will be measured by sessile drop analysis using a Krüss DSA machine and Drop Shape Analysis software (EasyDrop DSA20E, Krüss, Hamburg, Germany). The droplet volume and dispensing rate will be kept constant at 5.0 µL and 195 µL/min respectively within 10 s of dispensing. Surface energy will be calculated by the method described by Owens and Wendt with data from water contact angle (polar solvent) and diiodomethane (nonpolar solvent)[130].

Antibody Coating

The final goal of this proposal is regional drug delivery using an intravascular device, e.g. coronary stent, vascular graft, etc., as a platform. As proof of principle, we aim to capture EPCs that are genetically engineered to produce vasodilators (section 4.1.2) for potential therapeutic purposes. Genetic engineering techniques make it possible to produce EPCs that not only contribute to the endothialization of a device, but also produce therapeutic compounds. A key issue with using these genetically engineered EPCs, is ensuring that the device binds modified EPCs exclusively. Targeting CD34 leads to competition between the rare modified cells and the ubiquitous endogenous naive EPCs. To address this issue, cells can be further modified to produce a unique surface marker not found naturally in human cells to provide a target to exclusively capture compound producing cells. H-2K$^k$, a Major Histocompatibility Complex Class 1 molecule, has been found only in some rare murine strains (eg. AKR/JA or CBA/J). The absence of H-2K$^k$ within other mammalian cells makes it, and the monoclonal antibody to the H-2K$^k$ surface protein, attractive options to ensure exclusive capture of modified EPCs. The pMACSKk.tag (C) plasmid vector (Miltenyi Biotec) is a bioistronic vector containing H-2K$^k$ gene and a multiple cloning site (MCS) where a gene of interest can be cloned. Using pMACSKk.tag (C) plasmid vector, we have constructed a vector (pMACS-H-2K$^k$-hCGRP; also see section 4.2.1) that will express both H-2K$^k$ and the vasodilator calcitonin gene-related peptide (α-CGRP). We believe that H-2K$^k$ antibody coated vascular devices will selectively capture the genetically modified H-2K$^k$ expressing cells. Clinically available drug "eluting" stents deliver minute amounts of cytostatic drug to the vessel wall, only to tissue immediately adjacent to the stent struts, with no therapeutically relevant distal delivery. The goal of the technology described is to deliver therapeutic amounts of bioactive compound distal to the implanted device.

Oxidation method: t-Boc-hydrazide-PEG-amine (Quanta Biodesign) will be immobilized onto the PDA coated materials as described earlier (section 3.2.2). After successful immobilization of the PEG chains, the modified surfaces will be subjected to 25% trifluoroacetic acid (TFA) in methylene chloride followed by a 3 min rinse in 10% ammonium hydroxide to remove the t-Boc protecting group and form a hydrazide rich surface for additional immobilization[131,132]. Anti-H-2K$^k$ antibodies (IgG2a; Miltenyi Biotec, CA) will be oxidized to create the necessary aldehyde moieties[107, 108]. The antibody will be dissolved in PBS (0.05 mg/ml). Sodium m-periodate (Sigma-Aldrich) will then be added to the antibody solution (2 mg of sodium m-periodate per ml of antibody), and the reaction allowed to proceed for 30 minutes in the dark. After oxidation, the residual sodium m-periodate will be removed using a desalting column (Sephadex G-25). The PEG functionalized material will then be immersed in the oxidized antibody solution and allowed to react for 1 hour. Sodium cyanoborohydride (10 µL of 5.0 M sodium cyanoborohydride per ml of antibody) will be added to stabilize the Schiff base formed between the antibodies and the hydrazide rich coating. This reaction will proceed overnight at 4° C. Finally the material will be washed with PBS to remove physically adsorbed antibodies.

Enzyme method: Amino-PEG4-DBCO (Click Chemistry Tools) will be immobilized onto the PDA coated materials. Anti-H-2K$^k$ antibodies will be modified using the Click-IT® GlcNAc Enzymatic Labeling System (Life Technologies Inc) as per the manufacturer's instructions. Briefly, the antibodies (0.5 mg/mL, in PBS) will be buffer exchanged into the pre-treatment buffer (50 mM Na-phosphate, pH 6.0) using a micro-spin column prepared with P30 resin (Bio-Rad, 1.5 mL bed volume). 200 µL anti-H-2K$^k$ antibody will then be added to a pretreated column and centrifuged for 5 minutes at 850×g. The resultant antibody solution will be supplemented with 4 µL of β1,4-galactosidase (from S. pneumonia, 2 mU/µL) and placed in an incubator at 37° C. overnight. A buffer exchange of the sample into Tris buffered saline (TBS, 20 mM Tris HCl, 0.9% NaCl, pH 7.4) will be performed using a micro-spin column prepared with P30 resin. After the buffer exchange, 30 µL of the antibody solution (2 mg/ml) will be combined with 4 µL of UDP-GalNAz (40 mM), 15 µL of MnCl$_2$ (0.1M), and 100 µL of Gal-T(Y289L) (0.29 mg/mL) and incubated overnight at 30° C. After modification, the antibodies will be buffer exchanged into PBS. Finally, DBCO coated materials will be immersed in the antibody solution (100 µg/ml) for 120 min then washed with PBS to remove physically attached antibodies.

Isolation of porcine endothelial progenitor cells: EPCs are obtained at 4-7 days after culture of peripheral blood mononuclear cells in VEGF containing medium. They represent cells of hematopoietic origin and exert their angiogenic effects through the release of paracrine factors. Late EPCs (also termed endothelial colony-forming cells or late-outgrowth endothelial cells), appear after 2-4 weeks in culture. Late EPCs, unlike early EPCs, are believed to function as endothelial cells and can incorporate into vessels. Muscari et al compared different cell sources and culture conditions and found bone marrow-derived EPCs cultured for 3-4 weeks are committed to endothelial cell phenotypes[133]. We have adopted this method to procure the porcine EPCs to be used in the proposed research. Porcine bone marrow mononuclear cells will be isolated by Ficoll gradient centrifugation, plated at a density of 0.75×10$^6$/cm$^2$ in fibronectin coated T75 flasks and cultured in EGM-2 medium (Lonza). Our results show that porcine bone marrow derived EPCs express VEGFR2 and eNOS, 2 important endothelial markers. We will use EPCs expanded from bone marrow at week 3 after isolation as these demonstrate similar properties as late EPCs isolated from human peripheral blood mononuclear cells[133].

Cell culture and genetic engineering: COS-1 cells and CHO cells (both from ATCC) will be maintained in Dulbecco's Modified Eagle's Medium (DMEM, Life Technologies) supplemented with 10% FBS (Life Technologies). Transfection will be performed using Superfect Reagent (Qiagen) for COS-1 and Lipofectamine Reagent (Life Technologies) for CHO cells respectively, according to the manufacturers' instructions. EPCs will be transfected using a nucleoporation method according to the manufacturer's instructions (Amaxa Nucleofector). We have shown that all modified cells express H-2K$^k$ surface protein.

Evaluation of immunobinding efficiency and cell growth: H-2K$^k$ antibody coated materials (316L SS, CoCr, electrospun polyurethane and ePTFE) will be evaluated for their ability to selectively bind H-2K$^k$ expressing cells. In one embodiment, the antibodies were directly immobilized on the polydopamine-coated materials in the absence of any linker. For example, freshly prepared polydopamine-coated materials were exposed to an anti-H2kk antibody solution in PBS. The coated materials were then rinsed thoroughly with PBS to remove adsorbed antibody.

Transfected CHO cells will be detached, washed with and resuspended in PBS at a density of 10$^{6^6}$ cells/ml. Antibody coated disks, non-coated disks and disks coated with intermediate only will be blocked with PBS containing 2% BSA and incubated with 100 µl of cells followed by thorough washes with PBS to remove unbound cells. Bound cells will be fixed with 2% paraformaldehyde and visualized using fluorescent microscopy after nuclear staining with Sytox Green (Invitrogen). In addition, the fluorescent intensity of the disks will be measured using a SpectraMax M5e plate reader (Molecular Devices). Non-transfected cells will be used as a control. Our preliminary data have shown that immobilized H-2K$^k$ antibody is able to capture H-2K$^k$ expressing CHO cells on a number of different materials. To assess whether the coating impacts cell growth, H-2K$^k$ expressing EPCs will be detached, washed with PBS and resuspended in culture medium and added to antibody coated materials (316L SS, COCR, electrospun polyurethane, and ePTFE) placed in 24-well cell culture plates (each device in triplicate). At different time points after culture (day 1, 3 and 5), the samples will be taken out, washed with PBS and the attached cells will be lifted with 0.25% trypsin-EDTA (Life Technologies). Cell numbers will be determined and compared with those from uncoated material.

Cell capture using in vitro flow model: To test cell capture under flow conditions, an in vitro model of arterial blood flow has been developed in our lab. The model has a synthetic arterial space for stent deployment with flow controlled by a Harvard Apparatus syringe pump to provide alternating flow through the vascular device. Coated stents, uncoated stents, and stents coated with only the intermediate will be deployed within the synthetic artery. 10 ml of transfected cells ($10^5$ cells/ml) will be circulated for 1 hour at a flow rate of 3.1 mL/min[134]. The stents will then be recovered and washed with PBS to remove unbound cells. Bound cells will then be fixed and visualized as described in section 3.2.5.5. The fluorescent intensity will also be measured as described in section 3.2.5.5. Non-transfected cells will be used for control purposes.

Our results show capture of pig EPCs expressing H-2K$^k$ by anti-H-2K$^k$ antibody-coated vascular materials in vivo.

Cell toxicity assay for anti-H-2K$^k$ antibody-coated ePTFE graft was conducted. Coated grafts were incubated with CHO H-2K$^k$ (+) cells for 1, 2 or 3 days. They were then fixed and imaged by fluorescence microscope. Three sets were prepared for each day. Additional multiple spots on each graft was counted. One graft from each day was also fixed and taken for SEM.

Figure 15:
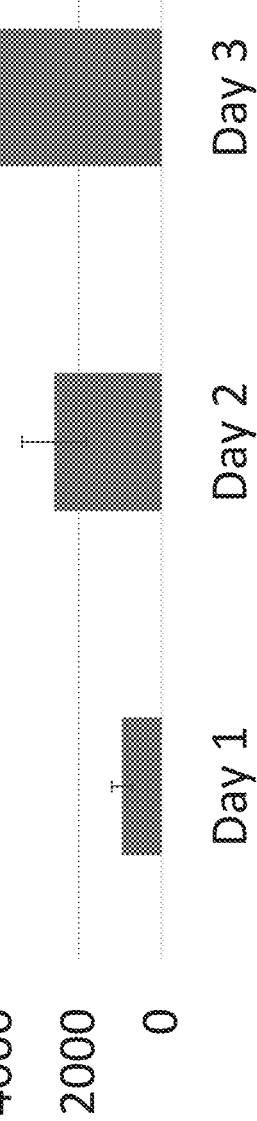
FIG. 15 shows cell toxicity assay for anti-H-2K$^k$ antibody-coated ePTFE graft. Coated grafts were incubated with CHO H-2K$^k$ (+) cells for 1, 2 or 3 days. They were then fixed and imaged by fluorescence microscope.

Cell Counts were determined by taking imaging multiple focal planes and coalescing all the images together. Ellipsoid or spherical shapes were deemed cells fitting into the following parameters (size: greater than 12 um×12 um and z: >40 um). This ensured that we were imaging and counting cells rather than any false positives. On Day 1, the average cell count was 960± 250 cells/mm$^2$. On Day 2, the average cell count was 2595±779 cells/mm$^2$. On Day 3, the average cell count was 10002±1745 cells/mm$^2$ (FIG. 15).

Grafts were incubated with CHO H-2K$^k$ (+) cells for 1, 2 and 3 days. They were then fixed (with multiple fixatives), critically point dried, gold-sputtered and then imaged by SEM. Additional multiple spots on each graft were analyzed. Only one graft from each day was imaged. Cell numbers increased; cell morphology also changed from spherical to flat and polygonal. This occurs as the cells grow and adhere to the graft.

Study 2

We hypothesize that antibody-functionalized stents can be employed to achieve protracted intracoronary administration of therapeutic substances (regional drug delivery) using a novel cell based delivery mechanism.

Background—Development of Cell-Based Drug Delivery System

Vascular Remodeling

The arterial wall is not a rigid tube, but rather an organ capable of reshaping in response to hemodynamic, mechanical, and biochemical stimuli. It has been known for more than a century that blood vessels enlarge to accommodate increasing flow to the organ downstream[135]. An obvious example of this process is the enlargement of coronary vessels during natural growth or in myocardial hypertrophy. Interest in this phenomenon was stimulated by histological observations that the radial enlargement of vessels (outward or positive remodeling) can compensate for progressive growth of atherosclerotic plaques, thus postponing the development of flow-limiting stenosis[136,137]. These pathological findings were subsequently supported by in vivo intravascular ultrasound (IVUS) studies that revealed the occurrence of outward remodeling in the presence of atheroma and how such outward remodeling could hide sizable plaques from angiographic detection[138,139]. Although most atherosclerotic segments exhibit some compensatory enlargement, it is often inadequate to completely preserve lumen size, and some vessels may paradoxically shrink at the lesion site (inward or negative remodeling), exacerbating rather than compensating for lumen loss[140]. This type of constrictive remodeling is reported to occur in 24% to 42% of culprit lesions in coronary arteries[141,142]. The clinical importance of negative remodeling is highlighted by the observation that luminal stenosis correlates more closely with the direction and magnitude of remodeling rather than with plaque size[140,143].

In normal arteries, remodeling is a homeostatic response to changes in the flow and circumferential stretch to restore normal shear stress and wall tension, respectively[144]. Outward remodeling, shown to occur in response to increased flow in coronary arteries from atherosclerotic monkeys[145], is largely dependent on shear-responsive endothelial production of nitric oxide and the matrix metalloproteinases (MMPs)[146,147]. Most of the mediators of shear-sensitive remodeling are also stretch responsive, and significant interaction between stretch and shear signals appears to exist[148]. Vessel elasticity is the chief determinant of resting vessel size, and recent data suggest that altered production of elastin may also be important in remodeling[149].

The presence of cardiac risk factors affects the remodeling process as well. Inadequate positive remodeling and negative remodeling are more common in insulin-using than non-insulin-using diabetics and in smokers compared with non-smokers[150,151]. Paradoxically, negative remodeling is less frequent in those with hypercholesterolemia[152]. Transplant vasculopathy, the most common cause of graft failure and death after heart transplantation, is characterized by diffuse angiographic narrowing. Recently it has become apparent that in addition to progressive intimal thickening, negative or inadequate positive remodeling is common in transplanted hearts[152].

Vasodilators

Prostacyclin: Prostacyclin (Prostaglandin I2, PGI2), a member of the prostaglandin family of lipid mediators, has potent vasodilator and antithrombotic activities[153,154]. Prostacyclin is an autocrine and paracrine mediator that binds to the specific G protein-coupled receptor, IP receptor, and/or to the nuclear receptor, peroxisome proliferators-activated receptor (PPAR) δ[155-158]. Prostacyclin exerts local anticoagulant and vasodilator properties, is not stored, and is rapidly converted by non-enzymatic processes to an inactive metabolite, 6 keto prostaglandin F1α (PGF1α). Prostacylin causes relaxation of vascular smooth muscle predominantly via the adenylyl cyclase/cyclic-AMP transduction system and causes vasodilation of all vascular beds studied[159].

Stable prostacyclin analogues are used clinically in the treatment of patients with peripheral and pulmonary vascular disorders, however their use is hindered by the fact that the substances are unstable and require continuous administration[154,160]. This limitation has led to the pre-clinical investigation of gene transfer technologies to provide continuous delivery of prostacyclin. Transfer of the human prostacyclin synthase (PGIS) gene has been shown to provide effective gene therapy for vascular diseases such as primary pulmonary hypertension[161-163] and for restenosis after vascular injury[164-166].

Calcitonin gene-related peptide ($\alpha$-CGRP): $\alpha$-CGRP, is distributed throughout the central and peripheral nervous systems (in vascular plexi) and exhibits biological effects including effects on the cardiovascular system. $\alpha$-CGRP is one of the most potent arterial and venous vasodilators identified to date, with a potency roughly 10-fold greater than the prostaglandins, 100-1000 times greater than other classic vasodilators (e.g., acetylcholine, adenosine, 5-hydroxytryptamine, and substance P), and 3-30 times more potent than the related peptide, adrenomedulin.

There are several mechanisms by which $\alpha$-CGRP produces vascular relaxation, mediated via the $CGRP_1$ receptor[167-169]. Current evidence points to the existence of both NO endothelium-independent and endothelium-dependent pathways. The endothelium-independent mechanism is observed in the majority of tissues that have been studied to date, including the porcine coronary artery[170]. The ability of $\alpha$-CGRP to relax these tissues in the absence of endothelium implies that it acts directly on the SMCs to stimulate adenylate cyclase and intracellular cAMP production, as has been demonstrated in vitro including[172,173]. $\alpha$-CGRP has been shown to stimulate voltage gated-calcium release in smooth muccle cells by 350% within 1 hour, and in the longer term (24-48 h) increases the density of sarcolemmal dihydropyridine receptors by 30%[171]. An endothelium-dependent pathway also exists with a significant increase in both cAMP and cGMP dependent on the secretion of NO[174]. The ability of CGRP to stimulate vasodilation in the absence of endothelium-derived NO makes it an attractive agent for use in patients with endothelial dysfunction, characterized by reduced eNOS activation.

In many species and in humans, the coronary arteries receive innervation from a high density of $\alpha$-CGRP-containing nerve fibers[174,176]. It is felt that $\alpha$-CGRP can have a protective influence by dilating coronary arteries at locations of atheromatous stenoses, delaying the onset of myocardial ischemia in patients with chronic angina[177]. The therapeutic potential for systemic administration of $\alpha$-CGRP to offset the adverse effects of CAD and ischemia is limited by the effects of systemic administration. The most important facet of the activity of $\alpha$-CGRP that leads to adverse effects is its potency as a peripheral vasodilator. The requirement of local administration of $\alpha$-CGRP to yield therapeutic benefit in the cardiovascular system means that targeted gene delivery may be a relevant method of treatment.

Research Design

Plasmid Construction

The human $\alpha$-CGRP complete cDNA (Open Biosystems, Huntsville Ala.) is used for PCR amplification of the DNA sequence encoding the biologically active mature CGRP, which is then fused with the FLAG epitope by inserting mature CGRP cDNA into the HindIII/EocRV sites of the vector pFLAG-CMV3 (Sigma). We have created a clone expressing mature CGRP tagged with FLAG, which facilitates the identification of mature $\alpha$-CGRP expression by using an anti-FLAG antibody. The FLAG-$\alpha$-CGRP cassette is then inserted into the EcoRV/EcoRI sites of the $pMACSK^k$.tag (C) vector generating the double ($H$-$2K^k$ and $\alpha$-CGRP) expression vector pMACS-H-$2K^k$-hCGRP. Prostacyclin synthase cDNA will also be cloned into the $pMACSK^k$.tag (C) vector.

Recombinant Lentivirus Vector

In addition to transfection with the plasmid vector (section 3.2.5.4), for proof-of-principle a lentivirus vector will be used to transduce EPCs to provide long-term gene expression. The recombinant lentivirus will be custom manufactured by Cell Biolabs Inc. (San Diego, USA). Our lab has successfully used a lentivirus expression system in a previous project and we have a great deal of experience in lentiviral transduction of EPCs and immortalized cell lines[178].

Measurement of Vasodilator Expression

Measurement of $\alpha$-CGRP expression and activity: $\alpha$-CGRP expression will be determined by Western blotting analysis using an anti-FLAG antibody (Sigma). We have shown that conditioned media (CM) from COS-1 cells transfected with the vector pMACS-H-$2K^k$-hCGRP contains CGRP. The biological activity of CGRP is assessed by its ability to induce nerve growth factor (NGF) production in human keratinocytes[179].

Measurement of prostacyclin synthase expression and activity: Prostacyclin synthase present in transfected cells will be determined by Western blotting using an antibody against human prostacyclin synthase (R & D Systems). Prostacyclin synthase activity will be assessed by measuring the metabolite 6-keto-PGF1$\alpha$ in the CM by radioimmunoassay (Amersham Corp) per the manufacturer's instructions.

Transgenic expression timeline: We have shown that pMACS-H-$2K^k$-hCGRP transfected CHO cells produce H-$2K^k$ protein for up to 5 days, while cell morphology and viability are not affected (data not shown). We will determine the stability of gene expression (both H-$2K^k$ and vasodilators) in both plasmid transfected and lentiviral transduced EPCs at days 1, 3, 5 and 7 post engineering.

In Vivo Cell Capture

All experiments will be performed in male Juvenile Yorkshire swine (>30 kg). Arterial access will be obtained through a left carotid arteriotomy. Prior to device implantation, hyperemia will be induced in the 3 major coronary arteries by the administration of 200 µg of intracoronary nitroglycerin. Coronary angiograms will lie obtained, and on-line quantitative coronary angiography (QCA) performed. Coronary artery cross-sectional area (CSA) of a vessel segment distal to the site of device implantation will be determined by Intravascular Ultrasound (IVUS) and Optical Coherence Tomography (OCT). Doppler derived blood flow velocities will be measured using a 0.014" steerable Doppler guidewire (ComboWire XT, Volcano Corp., San Diego, Calif.), analyzed on a Combomap system (Volcano Corp.) and reported as average coronary peak flow velocity (APV). Volumetric coronary bloodflow (CBF) will be calculated from the relationship CBF=CSA×APV as previously validated[189]. For the evaluation of cell capture on a stent platform, 8 mm long COCR coronary stents will be coated with PDA/PEG/anti-H-2K$^k$ and deployed randomly to proximal segments of the three major epicardial coronary arteries at 1.1:1 stent to vessel ratio. To evaluate cell capture on ePTFE, a PDA/PEG/anti-H-2K$^k$ coated Jostent Graftmaster Coronary Stent Graft (ePTFE sandwiched between two SS stents, Abbott Vascular) will be used. Cell administration will then be accomplished using a prototype tandem balloon catheter (kindly provided by Cordis Corporation). The catheter consists of two distal highly compliant balloons that are inflated through a single inflation port. Once inflated, a localized infusion chamber 1.0 cm in length is created between the balloons. Distal blood flow is afforded by a central lumen, and solutions can be infused or aspirated to the chamber via 2 separated ports. With the tandem balloons inflated to 25 psi (1.7 atm), saline will be delivered through the instillation port to clear the chamber of blood. Stented arterial segments will be randomized to receive 3×10$^6$ EPCs genetically manipulated to over-express H-2K$^k$ and either prostacyclin or α-CGRP or empty vector (expressing H-2K$^k$ only). H-2K$^{k+}$ EPCs will be enriched using the MACSelect Kk System (Miltenyi Biotec) following the manufacturer's instruction prior to delivery. 2 ml of cell suspension will be administered at an infusion rate of 200 µL/min over 10 minutes, followed by a 10 minute dwell time. The arteriotomy site will then be closed, and the animals allowed to recover. A total of 64 animals will be treated, with 2 stents per animal (16 protacyclin synthase (8 COCR, 8 ePTFE) and 16 α-CGRP (8 COCR, 8 ePTFE) and their respective controls), for both transfected and transduced EPCs. Two animals from each group will be sacrificed 5 days after stent implantation. Coronary angiography and QCA will be performed and the stented segments explanted. The explanted arterial segments will be bisected longitudinally and half analyzed by standard histochemical analysis and half processed for SEM imaging. Segments for histochemical analysis will be placed in a 10% formalin/PBS solution, and five sections cut and stained with hematoxylin & eosin (HE) as well as elastin trichrome. The degree of neoinitmal hyperplasia and the inflammatory (Kornowski Score (0-3)) scores will be determined to assess for evidence of rejection of the delivered cells[181]. Segments will be prepared for SEM by fixation in 10% buffered formalin/PBS for 30 seconds and further fixed in 2% PFA with 2.5% glutaraldehyde (BDH Inc.) in 0.1 M sodium cacodylate buffer (Sigma) overnight. Post-fixation will be completed with 1% osmium tetroxide (Sigma) in 0.1M cacodylate buffer followed by serial dehydration with ethanol and subsequent critical point drying. Gold sputtering and microscopy will then be performed at the SEM facility, University of Toronto, following established protocols. SEM will be performed to assess surface endothelialization. 28 days after the index procedure, the remaining animals (6 per group) will be anesthetized and coronary angiography with QCA analysis will be performed. The vessels will then be interrogated using IVUS and OCT. Coronary doppler flow will be measured and CBF calculated. We hope to see significant increases in vessel caliber beyond the stented segment in animals receiving vasodilator expressing EPCs.

Anticipated Results

Antibody Functionalized Materials

We expect to show PDA/PEG surface modification will provide an effective platform for antibody immobilization and can be used to create bioactive coatings on a range of biomedical materials. This technology has applications for the development of pro-healing devices, and as a platform for localized delivery of therapeutic compounds to target tissues in vivo.

A potential confounder is the unpredictability of antibody modification and it is possible that inadequate immobilization and denaturing of the antibody may occur. Although the described oxidation and enzymatic techniques effectively immobilize several antibodies of the same isotype onto substrates, the degree of glycosylation and accessibility of the sugar moieties on antibodies is variable[182]. If the described immobilization techniques fail to provide adequate binding for in vivo applications, alternative immobilization strategies will be explored. Of particular interest is a new UV immobilization technique. It utilizes indole-3-butyric acid-PEG to bind antibodies via a conserved nucleotide binding site found on virtually all antibodies, regardless of isotype[183].

Cell Based Drug Delivery System

We expect to show that this unique cell-based, intracoronary administration of potent vasodilators will promote positive remodeling of porcine coronary arteries. This will provide proof-of-principle for a technique that could be translated to a viable clinical therapy for patients with "no options" for conventional revascularization strategies. The possible clinical benefits could be derived not only from the positive remodeling of the conduit coronary arteries, but also through flow-mediated arteriogenesis to ischemic territories not supplied by feeder coronary arteries. The technology also has potential to be used for the delivery of a myriad of therapeutic compounds to various target tissues in the body.

Although the antigenic load of H-2K$^k$ surface protein is exceedingly small, and unlikely to elicit a cellular immune response, if there is evidence of cell attrition or vessel wall inflammation in our early timepoints after stent implantation, we will change the surface marker/antibody system from H2Kk/anti-H-2K$^k$ to ΔLNGFR/anti-LNGFR (Miltenyi Biotec, CA). There is mounting evidence that the ΔLNGFR surface marker is less immunogenic[184], and there is published evidence of the long-term survival of autologous mesenchymal stem cells expressing ΔLNGFR in a porcine model of myocardial infarction[185].

Example 4 Polydopamine-PEG-Antibody Stent Coating

Polydopamine (PDA) Coating

Figure 4A:
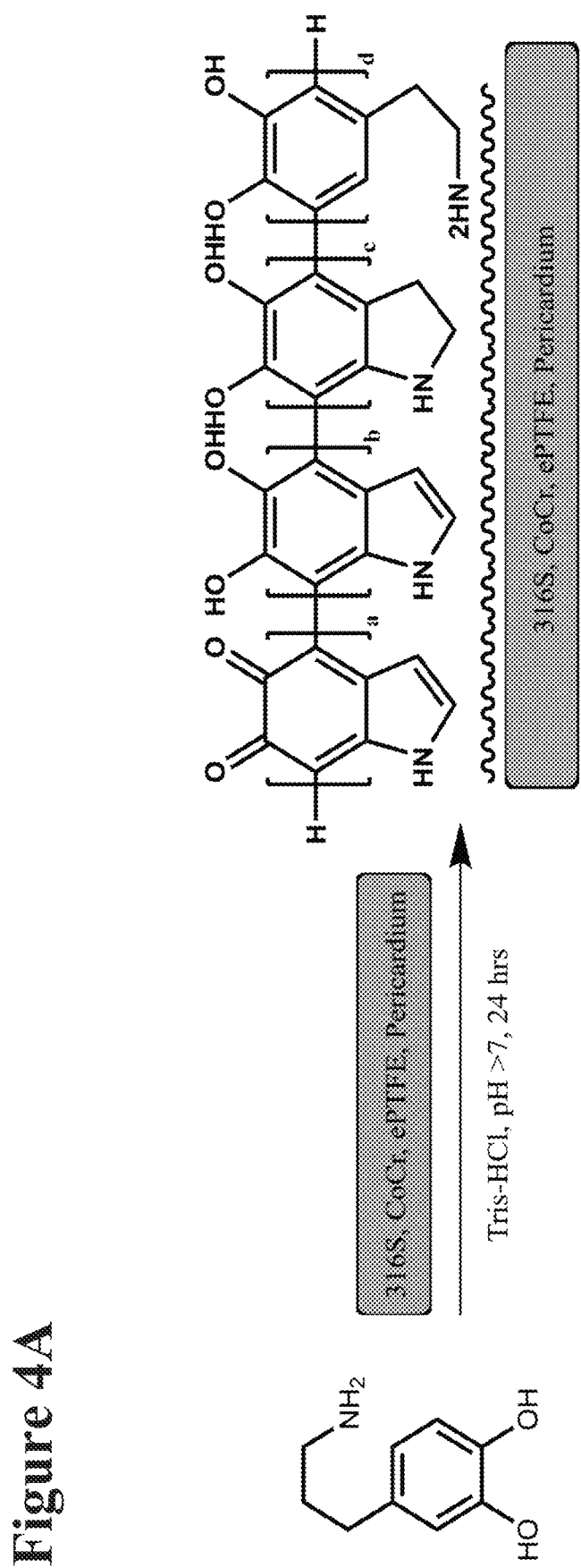

Stents (stainless steel and CoCr) were sonicated in the following liquids, deionised water, acetone, ethanol and water for 5-minute durations. The stents were then dried under air. The bovine pericardium grafts were not sonicated to avoid protein denaturation; however, to remove excess free aldehydes the grafts were pre-washed with PBS (pH 7.2) for 24 hours, then 0.5M TRIS-HCl (pH 6) for 1 hour and then rinsed with deionized water. Additionally, the pericardium and ePTFE grafts were not air dried but rather underwent solvent exchange from water to 10 mM Tris-HCl buffer (pH 8.6). Stents were then coated with polydopamine by dip coating in a dopamine hydrochloride solution (2 mg/ml) in 10 mM Tris-HCl buffer (pH 8.6) at room temperature for 24 hours with orbital mixing (FIGS. 4A-4B). A solution of 5-10 mg/ml dopamine hydrochloride was used when coating ePTFE and bovine pericardium grafts.

PEG Coating

Figure 6:
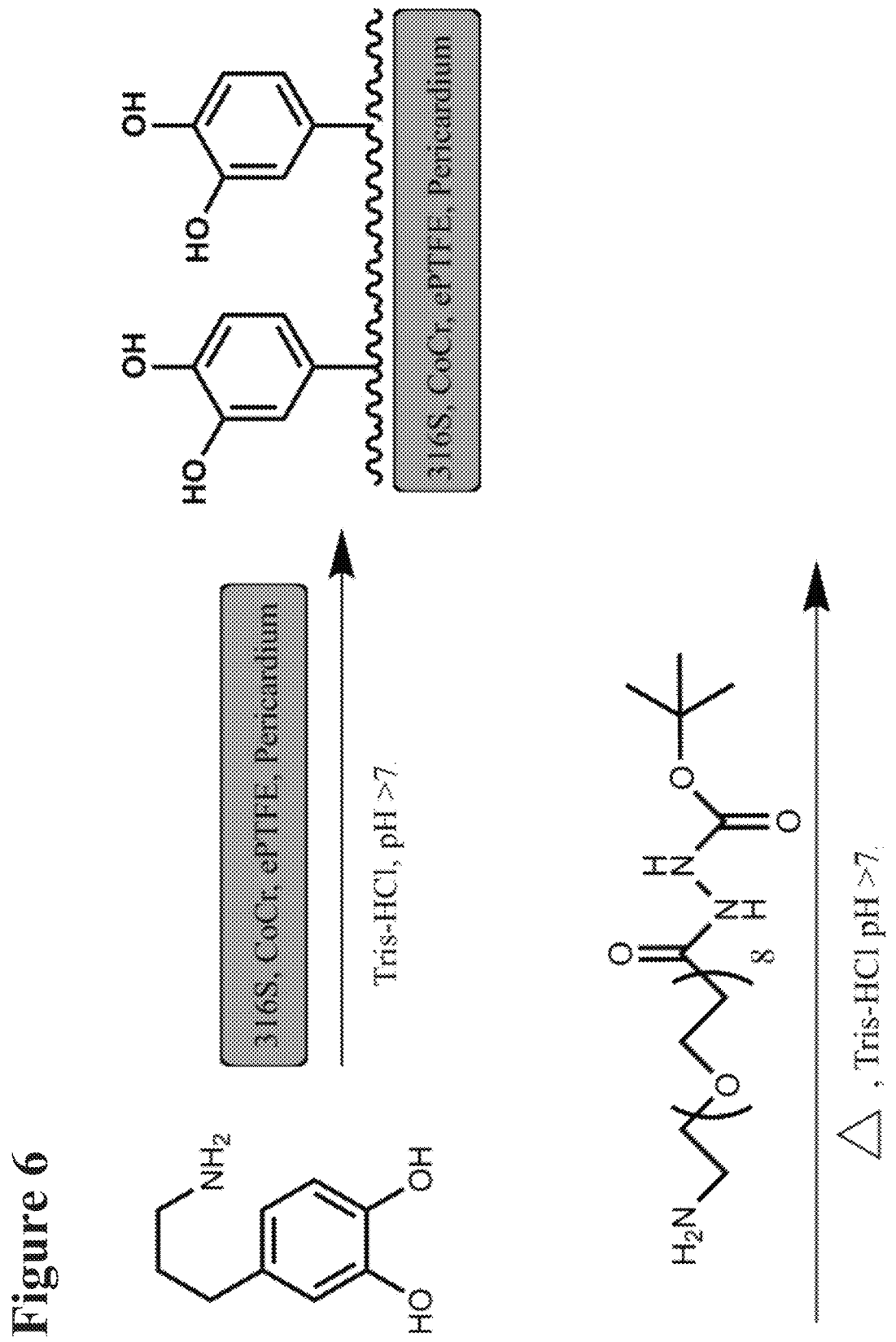
FIG. 6 shows an exemplary reaction scheme (oxidation method) for coating a substrate/intravascular material/medical device (e.g., 316L stainless steel (316L SS), cobalt-chromium (CoCr), ePTFE, or pericardium) with antibodies (e.g., anti-CD34 antibodies) bound to polydopamine via an intermediate PEG-linker. As an example, PEG is shown to conjugate to polydopamine via a Michael addition.
Figure 6:
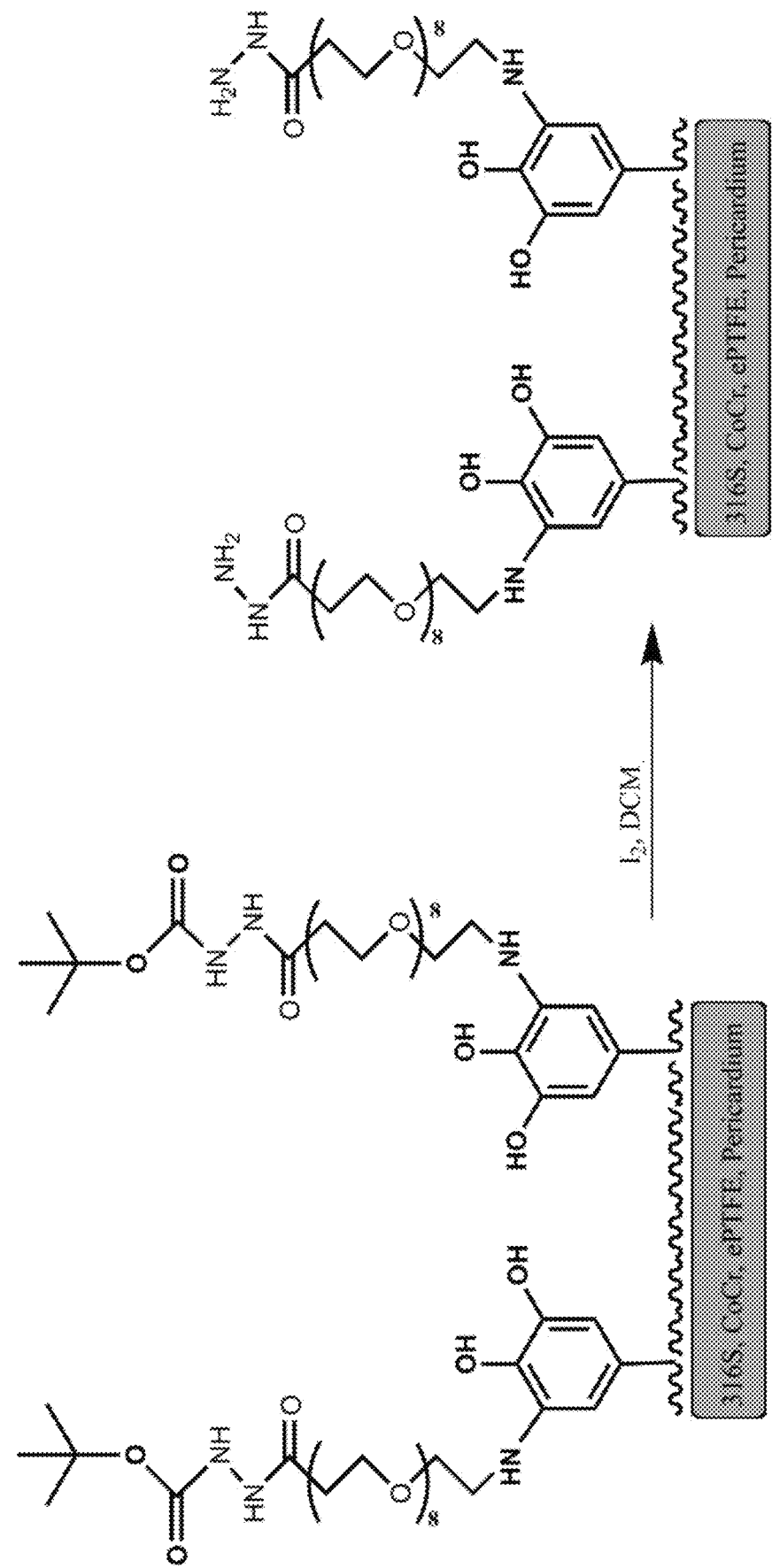
Figure 6:
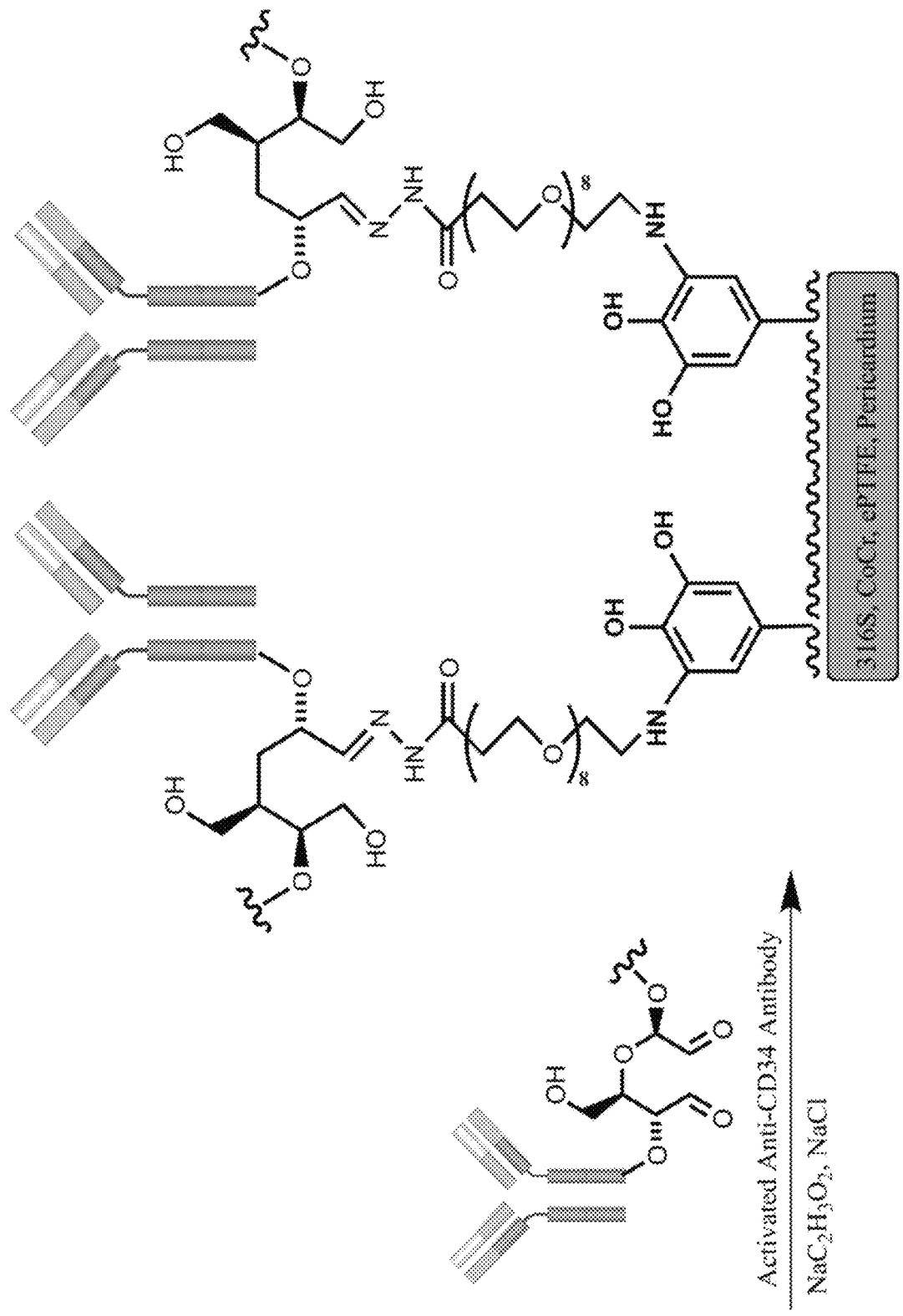
Figure 7:
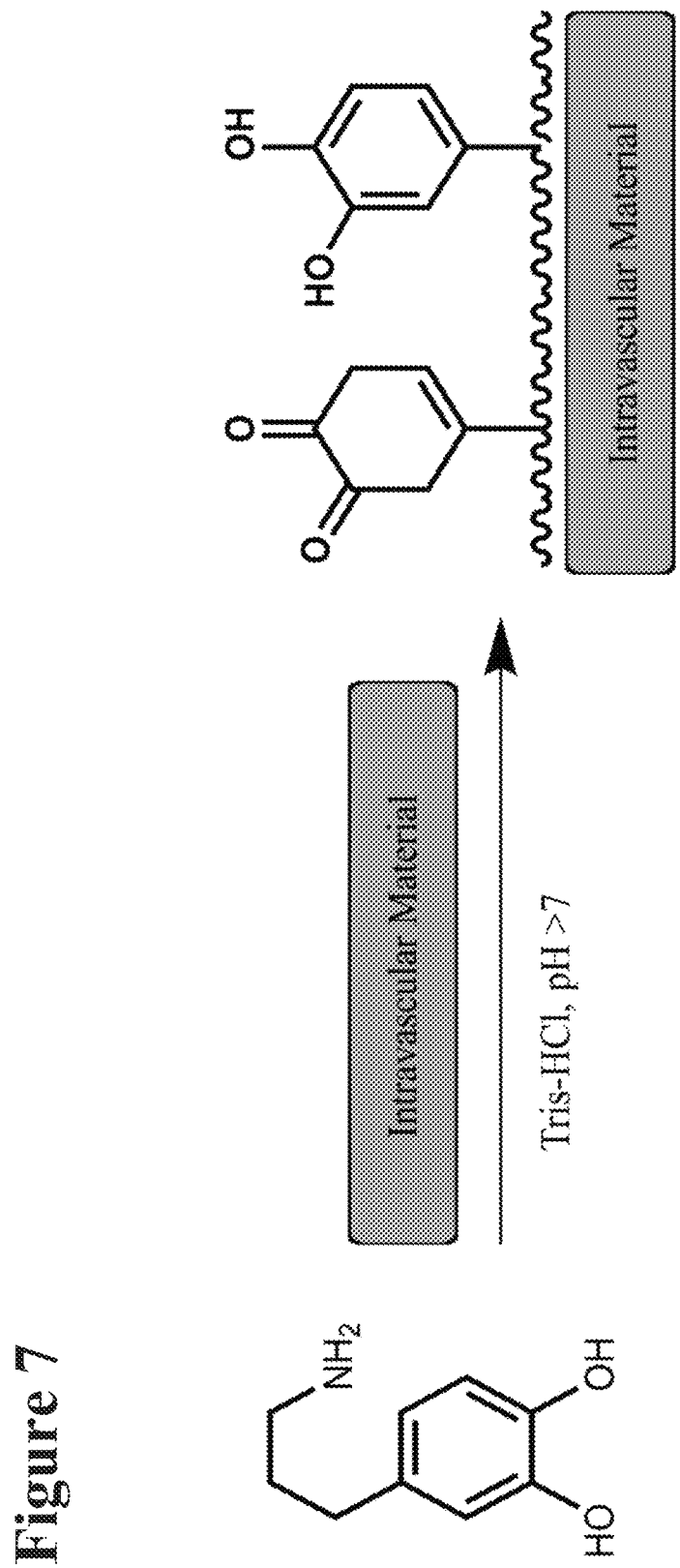
FIG. 7 shows an exemplary reaction scheme for coating a substrate/intravascular material/medical device (e.g., 316L stainless steel (316L SS), cobalt-chromium (CoCr), ePTFE, or pericardium) with antibodies (e.g., anti-CD34 antibodies) bound to polydopamine via an intermediate PEG-linker. As an example, PEG is shown to conjugate to polydopamine via a Michael addition or a Schiff Base reaction.
Figure 7:
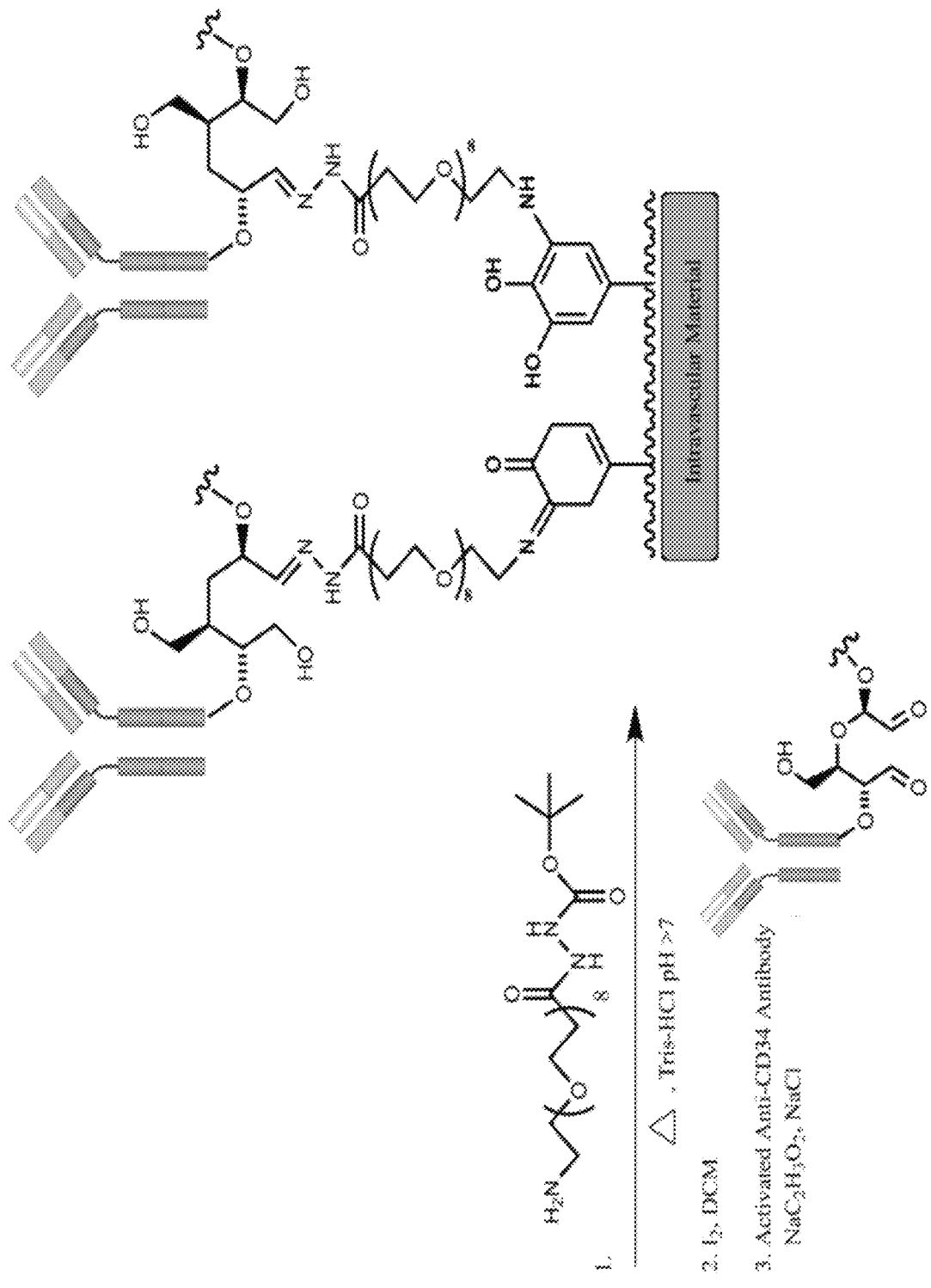
Figure 8A:
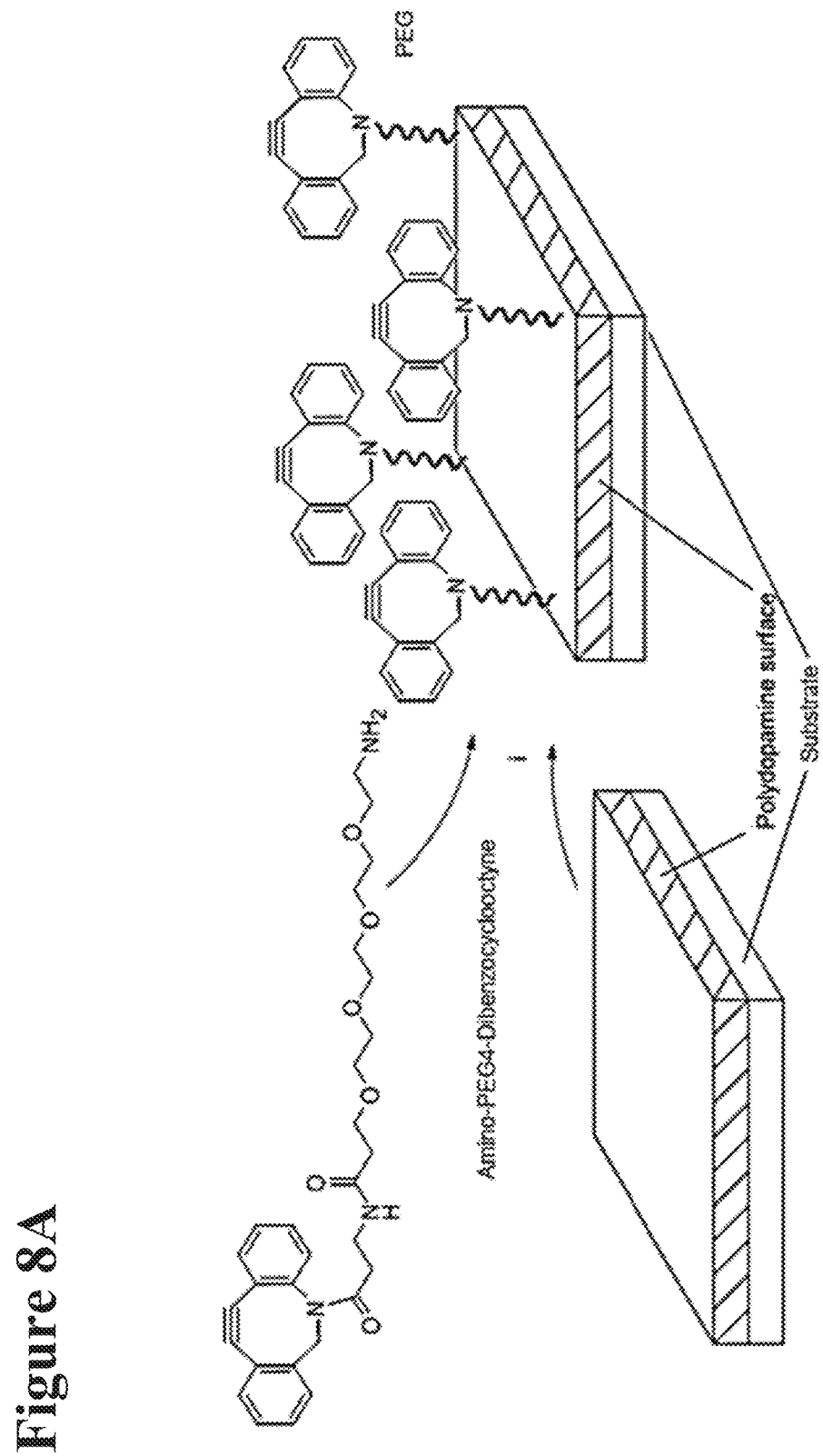
FIGS. 8A-8C shows an exemplary reaction scheme (enzyme method) for coating a substrate/intravascular material/medical device with antibodies bound to polydopamine via an intermediate PEG-linker.
Figure 8B:
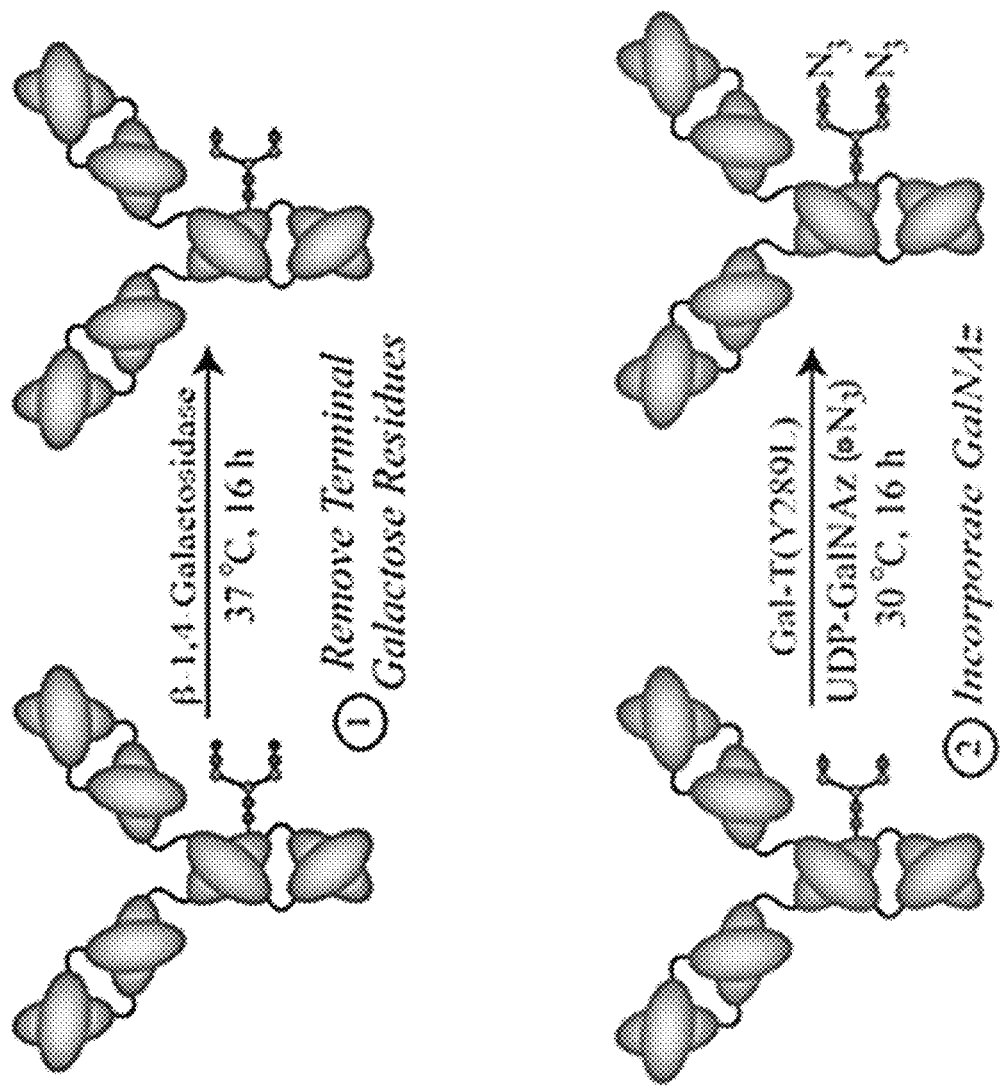
Figure 8C:
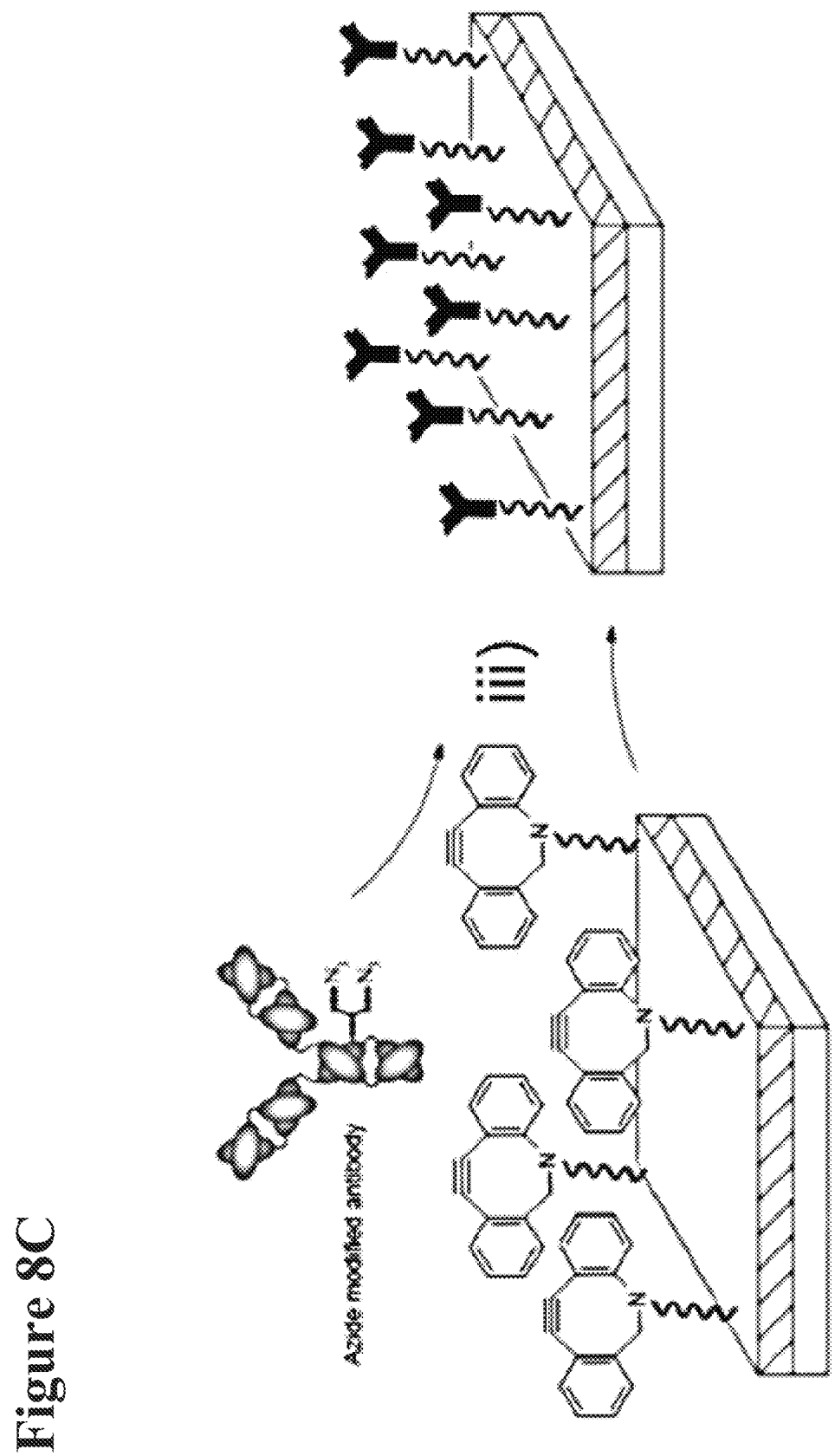
Figure 14:
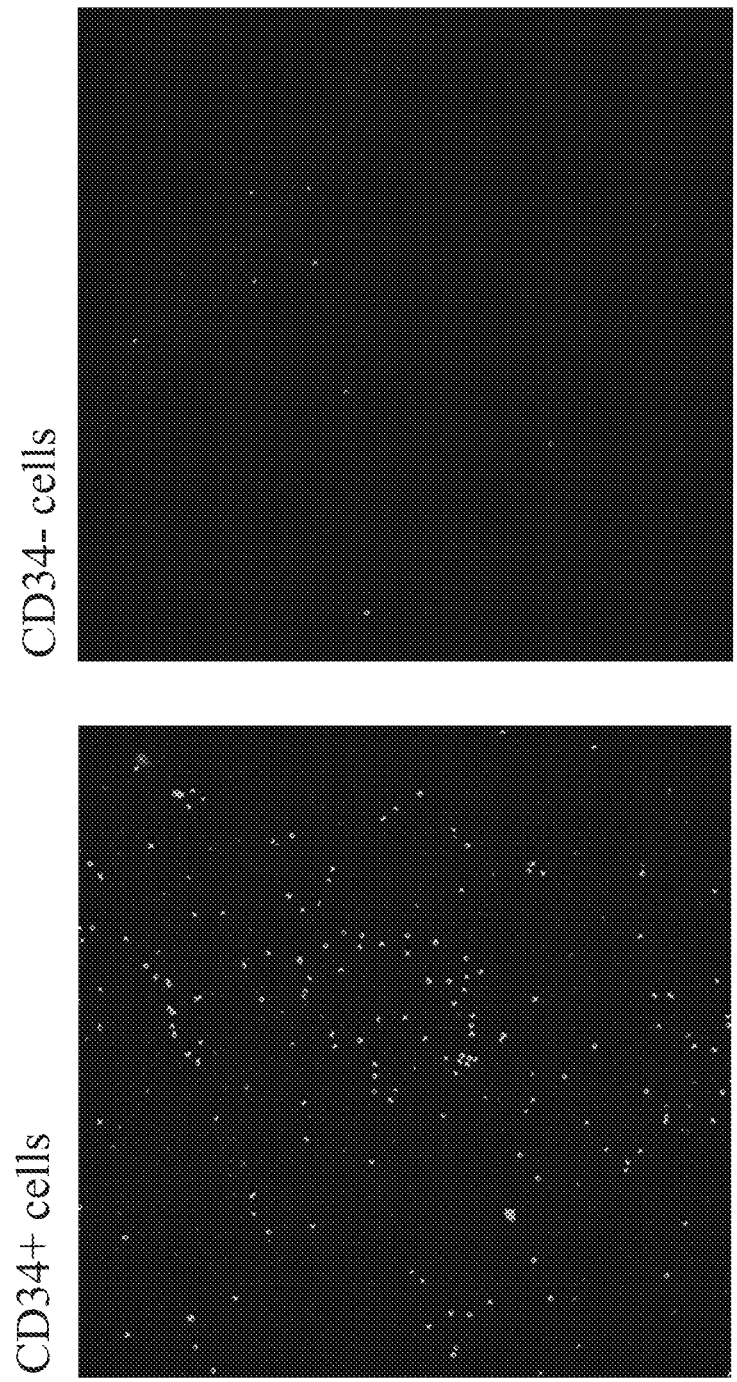
FIG. 14 shows capture of CD34-expressing Kg1a cells ("CD34+ cells") on bovine pericardium coated with anti-CD34 antibodies (BioLegend, #343602) via an intermediate Amino-dPEG$_8$-t-boc-hydrazide linker bound to polydopamine formed by oxidative self-polymerizaiion of dopamine. Coatings were blocked with bovine serum albumin (BSA) before incubation with cells. Bound cells were visualized by the nuclear dye Sytox Green staining on confocal microscopy. Control cells were CHO cells that do not express CD34 ("CD34− cells").

PDA-coated stents were rinsed with deionized water prior to reaction with 25 mg/ml t-Boc-hydrazide-PEG$_8$-amine MW:555.66 g/mol (Quanta Biodesign) in Tris-HCl buffer (pH 8.6) The reaction was carried out at 50 degrees Celsius for 24 hours. (FIGS. 6 and 7). The stents were then washed at room temperature and dried. Note that ePTFE and bovine pericardium were not dried but rather underwent solvent exchange from water, to acetone to dichloromethane (DCM). The PEGylated stents were then deprotected by removal of the t-boc functional group with iodine (I$_2$) at 2 mg/ml in DCM for 5 hours at room temperature with constant air flow and exhaust for $CO_2$ by-product release. Once the reaction was complete the stents were then washed with DCM and dried under nitrogen/argon. For bovine pericardium and ePTFE grafts, the materials were kept wet by solvent exchange from DCM to ethanol to deionized water before further processing.

Antibody Oxidation

Figure 5:
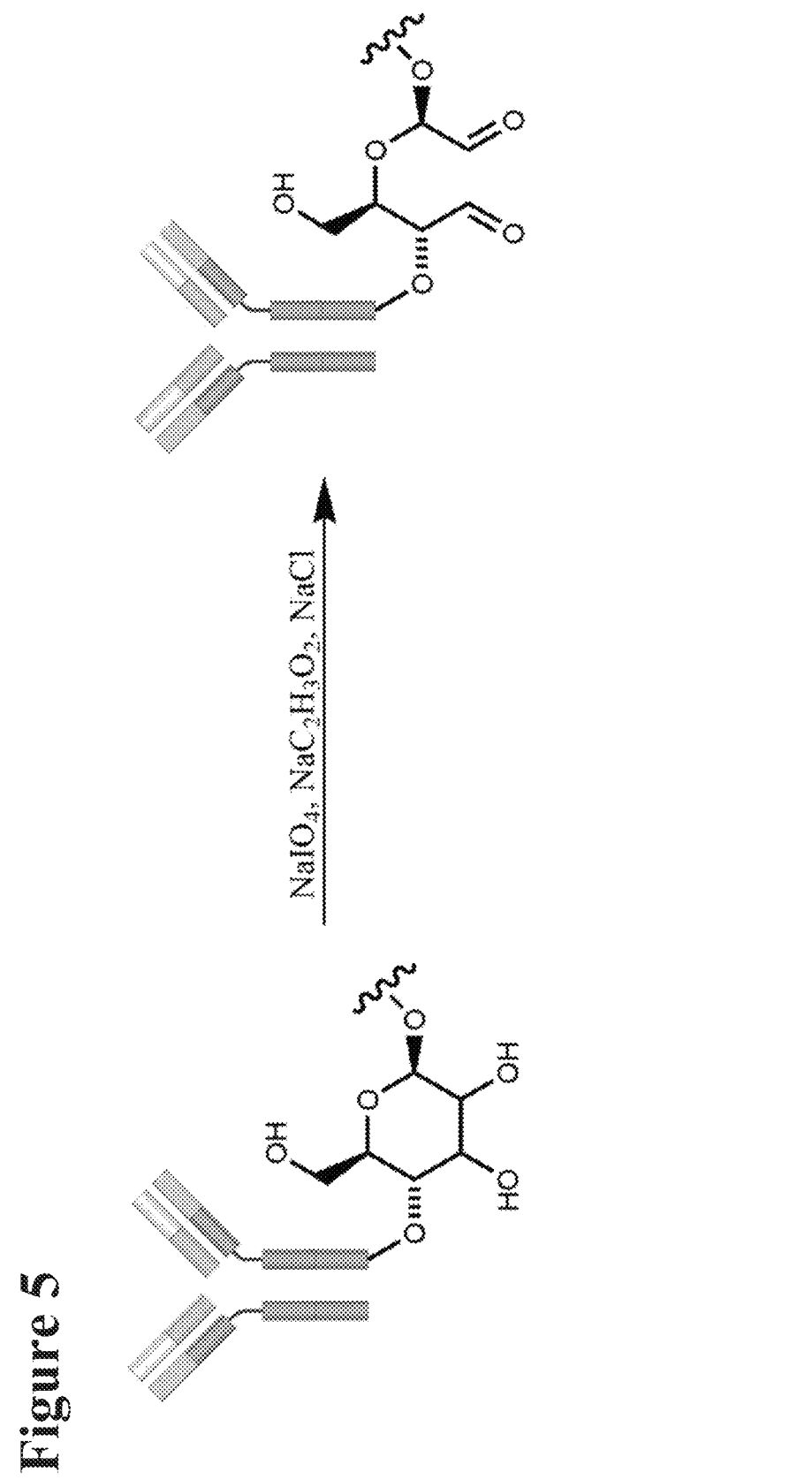
FIG. 5 shows an exemplary reaction scheme for the oxidative activation of antibodies or antibody fragments for later coupling to nucleophilic presenting surfaces.

The selected antibody was dissolved in a buffer solution containing 20 mM sodium acetate and 15 mM sodium chloride at a pH ranging from pH 4-6.5). The antibody was then oxidized with sodium periodate (FIG. 5). The reaction flask was covered in aluminum foil to prevent light exposure. The oxidized antibody was purified by column chromatography with a CPD Mini Trap G-25 column (GE Life Sciences). The removal of the oxidant and the presence of the purified antibody was confirmed via UV spectroscopy.

Antibody Conjugation to PDA-PEG

The PDA-PEG coated stent was immersed in the purified antibody solution. After reaction, the stent was removed, washed and left in PBS pH 7.2 until further testing (FIGS. 6 and 7).

Example 5 Coating Biocompatibility: Cell Toxicity Assay

Cell toxicity of anti-CD34 antibody-coated ePTFE surface was assessed. HUVECs (about 30% CD34 positivity) were seeded onto the coated surface. 24 hours and 48 hours after seeding, cells grown on the surface were stained with fluorescence dye and observed under fluorescence microscope.

Example 6

The aim of this study is to develop a novel approach for the promotion of positive coronary artery remodeling to improve distal flow using a technique for the localized capture of genetically modified EPCs. We hypothesize that the chronic intracoronary administration of potent vasodilators will increase coronary flow and result in an increase in vessel caliber through positive remodeling of the vessel. We intend to target the delivery of EPCs, genetically modified to express potent vasodilators, to promote flow-dependent positive remodeling of epicardial coronary arteries.

A stent (e.g., cobalt chromium stent, 9 mm long), coated with PDA/PEG/anti-H-2K$^k$ antibodies, is implanted upstream of the targeted vessel site in vitro or in a subject (e.g., an experimental animal or a patient).

Genetically modified cells (e.g., transfected with a bioistronic vector encoding either PGIS or α-CGRP) are administered to in vitro system or to the subject, e.g., delivered through the wire port of a standard balloon catheter, and released into isolated lumen of vessel. Genetically modified cells proliferate and express proteins such as PGIS or α-CGRP (cells expected to express CGRP for >16 days (Nagaya et al. 2003)). α-CGRP proteins travel downstream and attaches to CGRP1-receptor. Vessel dilates in response to released GGRP protein. Long-term effects include positive remodeling of the vessel.

Methods

Genetic Modification of EPCs

Porcine bone marrow derived EPCs were isolated and cultured according to a protocol previously established in our lab. A double-gene (H-2K$^k$ and human α-CGRP) expression vector was constructed and introduced into EPCs using electroporation. For example, plasmid pMACS K$^k$.II (Miltyneyi Biotec) expressing the truncated mouse MHC class 1 molecule H-2K$^k$ was constructed. Genetically modified EPCs were assayed for H-2K$^k$ and α-CGRP production by flow cytometry and Western blotting respectively. α-CGRP biological activity was assayed.

In Vitro Cell Binding Assay

Anti-H-2K$^k$ antibody coated substrates were blocked with PBS containing 2% BSA. EPCs expressing H-2K$^k$ were mixed with BSA-blocked H-2K$^k$ Ab-coated substrates, and incubated at room temperature for 1 hour. Unbound cells were washed off with PBS and bound cells were fixed and stained with the fluorescent nuclear dye Sytox Green, and observed under fluorescent microscopy. The fluorescent intensity was also measured using a fluorescence reader.

Results

Dual Expression (H-2K$^k$ and α-CGRP) by Genetically Modified Pig EPCs

67% of pig EPCs express H-2K$^k$ 24 hours after genetic modification. Double expression vector modified pig EPCs also express α-CGRP.

α-CGRP Biological Activity Assay

CGRP biological activity was assayed by its ability to up-regulate nerve growth factor (NGF) expression in keratinocytes, e.g., in an ELISA assay.

CONCLUSIONS

The new coating technology can be applied to various materials (stainless steel, cobalt chromium, ePTFE, pericardium etc.).

Antibodies, such as anti-CD34 and anti-H-2K$^k$ antibodies, can be immobilized on various vascular device with the new coating technology.

Porcine EPCs can be genetically engineered to express the potent vasodilator α-CGRP and/or a foreign antigen, e.g., H-2K$^k$ (or truncated H-2K$^k$), that can be employed for cell capture. Anti-H-2K$^k$ antibody-coated vascular materials can capture EPCs expressing H-2K$^k$ (or truncated H-2K$^k$) in vitro and in vivo.

Example 7

In situ accessibility of Fab and Fc domains of immobilized antibodies will be analyzed according to Saha et al.

Analyst 142:4247-4256 (2017). Fab domain accessibility assay—a known amount of a monoclonal antibody, e.g., anti-CD34, coated devices (e.g., disks, ePTFE grafts, stents) will be incubated with a molar excess (relative to the molar amount of bound antibody) of an antigen, e.g., soluble CD34, which is capable of binding to the bound monoclonal antibody. Using a molar excess will saturate available antibody domains. After incubation, the coated devices will be washed and a second, 125I radiolabeled monoclonal antibody which binds to a different epitope from the first monoclonal antibody will be added in a molar excess (relative to the amount of bound monoclonal antibody). The devices will be incubated for a period of time ranging from about 1 hr to about 3 hours, washed, e.g., with Phosphate buffered sale (PBS) and radioactivity (cps) measured in a gamma counter. Stocks of different known concentrations of 125I radiolabeled second monoclonal antibody in solution will be taken as a control. The amount of bound second radiolabeled monoclonal antibody in the Fab accessibility assay will then be calculated by subtracting the signal of monoclonal antibody coated devices from the final signal after binding of the second radiolabeled monoclonal antibody. Saha et al. Analyst 142:4247-4256 (2017). Other techniques used to determine the activity, accessibility and orientation of immobilized antibodies, include, atomic force microscopy, neutron reflection, spectroscopic ellipsometry and mass spectrometry. Id.

Polydopamine-PEG-antibody coated substrates, such as grafts, stents, disks, nanoparticles, etc. (e.g., metallic or polymeric) will be prepared as set forth in Example 4. Antibodies, e.g., monoclonal anti-CD34 antibodies, will be coupled to the Polydopamine-PEG moieties as set forth above. A second anti-CD34 monoclonal antibody, where the second monoclonal antibody is directed to an epitope on the CD34 molecule different from the monoclonal, anti-CD34 antibody which is coupled to the polydopamine-PEG, will be radiolabeled (iodination reagent (or 'Iodo-gen': 1,3,4,6-tetrachloro-3α,6α-diphenylglycouril) from Thermo Fisher Scientific (Cat. No. 28601)). In certain embodiments, if the antigen has multiple epitope sites which are the same, the second monoclonal antibody can be directed to the same site. The binding of the radiolabeled anti-CD34 monoclonal antibody to CD34 bound to anti-CD34-Polydopamine-PEG will be measured as follows.

Anti-CD34-Polydopamine-PEG coated disks will be incubated with a molar excess of soluble CD34 in PBS for 1 hour (10 mM phosphate buffered saline, pH 7.4). A molar excess of CD34 will be used in order to saturate the available antibody domains. After incubation, the anti-CD34-Polydopamine-PEG coated disks will be washed twice with PBS buffer and the 125I radiolabeled, second anti-CD34 monoclonal antibody will be added for the sandwich assay binding. A molar excess of the second monoclonal antibody will be used. After incubation for 1 h, the anti-CD34-Polydopamine-PEG coated disks will be washed three times with PBS and re-suspended in final 100 μl of PBS buffer for measuring the final radioactivity (cps) in a gamma counter. The amount of bound radiolabeled anti-CD34 monoclonal antibody will be determined by the signal after binding of the radiolabeled, anti-CD34, monoclonal antibody.

The binding of the radiolabeled, anti-CD34 antibody to polydopamine-PEG-antibody coated disks will be greater than the binding of radiolabeled, anti-CD34 coated disks lacking PEG or polydopamine. Fab accessibility scale will be expressed as a mass ratio and as a number ratio.

Cell adhesion may be assessed using a suitable method, such as cell adhesion assays. Adherent cells may be quantified using colorimetric or fluorometric detection.

REFERENCES

1. Ross R. Atherosclerosis is an inflammatory disease. Am Heart J. 1999; 138(5 Pt 2):S419-20.
2. American Heart Association. 2002 Heart and Stroke Statistical Update. Dallas, Tex.: American Heart Association.
3. Antiplatelet Trialists' Collaboration. Collective overview of randomized trials of antiplatelet therapy—II: Maintenance of vascular graft or arterial patency by antiplatelet therapy. Antiplatelet Trialists' Collaboration. Brit. Med. J. 1994; 308:159-68.
4. Bearn P E, Seddon A M, McCollum C N, Marston A. Mesothelial seeding of knitted Dacron, Br. J. Surg. 1993; 80:587-91.
5. Wilcox J. Thrombin and other potential mechanisms underlying restenosis. Circulation. 1991; 84:432-35.
6. Schwartz S M. Serum derived growth factor is thrombin? J. Clin. Invest. 1993; 91:4.
7. Hedin U, Frebelis S, Snachez J, Dryjski M, Swedenberg J. Antithrombin III inhibits thrombin-induced proliferation in human arterial smooth muscle cells. Arterioscler. Thromb. Vasc. Biol. 1994; 14:254-60.
8. Pevec W C, Darling R C, L'Italien G J, Abbott W M. Femoropopliteal reconstruction with knitted, nonvelour Dacron versusexpanded polytetrafluoroethylene. J. Vasc. Surg. 1992; 16:60-5.
9. Tassiopoulos A, Greisler H P. Angiogenic mechanisms of endothelialization of cardiovascular implants: a review of recent investigative strategies. J. Biomat. Sci. Polymer. Edn. 2000; 11:1275-84.
10. Clowes A W, Kirkman T R, Reidy M A. Mechanisms of arterial graft healing. Rapid transmural capillary ingrowth provides a source of intimal endothelium and smooth muscle in porous PTFE prostheses. Am. J. Pathol. 1986; 123:220-30.
11. Kohler T R, Stratton J R, Kirkman T R. Johansen K H, Zierler B K, Clowes A W. Conventional versus high-porosity polytetrafluorethylene grafts: clinical evaluation. Surgery 1992; 112:901-7.
12. Shi Q, Wu MH-D, Hayashida N, et al. Proof of fallout endothelialization of impervious Dacron grafts in the aorta and inferior vena cava of the dog. J. Vasc. Surg. 1994; 20:546-56.
13. Shi Q, Wu MH-D, Fujita Y, et al. Genetic tracing of arterial graft flow surface endothelialization in allogenic marrow transplanted dogs. Cardiovasc Surg. 1999; 7:98-105.
14. Shi Q, Rafii S, Wu M H, et al. Evidence for circulating bone marrow derived endothelial cells. Blood. 1998; 92:362-7.
15. Kearney M, Pieczek A, Haley L, et al. Histopathology of In-Stent Restenosis in Patients With Peripheral Artery Disease. Circulation. 1997; 95:1998-2002.
16. Kidane A G, Salacinski H, Tiwari A, Bruckdorfer K R, Seifalian A M. Anticoagulant and Antiplatelet Agents: Their Clinical and Device Application(s) Together with Usages to Engineer Surfaces. Biomacromolecules. 2004; 5:798-813.
17. Lüscher T F, Barton M. Biology of the endothelium. Clin. Cardiol. 1997; 20(11 Suppl 2):3-10.

18. Herring M, Gardner A, Glover J. A single-staged technique for seeding vascular grafts with autogenous endothelium. Surgery. 1978; 84:498-504.
19. Zilla P, Fasol R, Dudeck U, et al. In situ calculation, microgrid follow-up and low-density plating provide first passage endothelial cell masscultures for in vitro lining. J. Vasc. Surg. 1990; 12:180-9.
20. Mansfield P B, Wechezak A R, Sauvage L R. Preventing thrombus on artificial vascular surfaces: true endothelial cell linings. Trans. Am. Soc. Artif. Intern. Organs. 1975; 21:264-72.
21. Herring M, Gardner A, Glover J. Seeding endothelium onto canine arterial prostheses. The effects of graft design. Arch. Surg. 1979; 114:679-82.
22. Allen B T, Long J A, Clark R E, et al. Influence of endothelial cell seeding on platelet deposition and patency in small-diameter Dacron arterial grafts. J. Vasc. Surg. 1984; 1:224-33.
23. Belden T A, Schmidt S P, Falkow L J, Sharp W V. Endothelial cell seeding of small-diameter vascular grafts. Trans. Am. Soc. Artif. Intern. Organs. 1982; 28:173-7.
24. Burkel W E, Vinter D W, Ford J W, et al. Sequential studies of healing in endothelial seeded vascular prostheses: histologic and ultrastructure characteristics of graft incorporation. J. Surg. Res. 1981; 30:305-24.
25. Graham L M, Burkel W E, Ford J W, et al. Immediate seeding of enzymatically derived endothelium in Dacron vascular grafts. Early experimental studies with autologous canine cells. Arch. Surg. 1980; 115:1289-94.
26. Herring M, Baughman S, Glover J, et al. Endothelial seeding of Dacron and polytetrafluoroethylene grafts, the cellular events of healing. Surgery. 1984; 96:745-55.
27. Kempczinski R F, Rosenman J E, Pearce W H, et al. Endothelial cell seeding of a new PTFE vascular prosthesis. J. Vasc. Surg. 1985; 2:424-9.
28. Schmidt S P, Hunter T J, Falkow L J, Evancho M M, Sharp W V. Effects of antiplatelet agents in combination with endothelial cell seeding on small-diameter Dacron vascular graft performance in the canine carotid artery model. J. Vasc. Surg. 1985; 2:898-906.
29. Schmidt S P, Hunter T J, Hirko M, et al. Small-diameter vascular prostheses: two designs of PTFE and endothelial cell-seeded and nonseeded Dacron. J. Vasc. Surg. 1985; 2:292-7.
30. Stanley J C, Burkel W E, Ford J W, et al. Enhanced patency of small-diameter, externally supported Dacron iliofemoral grafts seeded with endothelial cells. Surgery. 1982; 92:994-1005.
31. Herring M, Baughman S, Glover J. Endothelium develops on seeded human arterial prosthesis: a brief clinical note. J. Vasc. Surg. 1985; 2:727-30.
32. Herring M, Gardner A, Glover J. Seeding human arterial prostheses with mechanically derived endothelium. The detrimental effect of smoking. J. Vasc. Surg. 1984; 1:279-89.
33. Herring M, Smith J, Dalsing M, et al. Endothelial seeding of polytetrafluoroethylene femoral popliteal bypasses: the failure of low-density seeding to improve patency. J. Vasc. Surg. 1994; 20:650-5.
34. Herring M B, Compton R S, LeGrand D R, et al. Endothelial seeding of polytetrafluoroethylene popliteal bypasses. A preliminary report. J. Vasc. Surg. 1987; 6:114-8.
35. Jensen N, Lindblad B, Bergqvist D. Endothelial cell seeded dacron aortobifurcated grafts: platelet deposition and long-term follow-up. J. Cardiovasc. Surg. 1994; 35:425-9.
36. Ortenwall P, Wadenvik H, Kutti J, Risberg B. Reduction in deposition of indium 111-labeled platelets after autologous endothelial cell seeding of Dacron aortic bifurcation grafts in humans: a preliminary report. J. Vasc. Surg. 1987; 6:17-25.
37. Ortenwall P, Wadenvik H, Risberg B. Reduced platelet deposition on seeded versus unseeded segments of expanded polytetrafluoroethylene grafts: clinical observations after a 6-month follow-up. J. Vasc. Surg. 1989; 10:374-80.
38. Ortenwall P, Wadenvik H, Kutti J, Risberg B. Endothelial cell seeding reduces thrombogenicity of Dacron grafts in humans. J. Vasc. Surg. 1990; 11:403-10.
39. Smyth J V, Welch M, Carr H M, et al. Fibrinolysis profiles and platelet activation after endothelial cell seeding of prosthetic vascular grafts. Ann. Vasc. Surg. 1995; 9:542-6.
40. Zilla P, Fasol R, Deutsch M, et al. Endothelial cell seeding of polytetrafluoroethylene vascular grafts in humans: a preliminary report. J. Vasc. Surg. 1987; 6:535-41.
41. Hess F, Steeghs S, Jerusalem R, et al. Patency and morphology of fibrous polyurethane vascular prostheses implanted in the femoral artery of dogs after seeding with subcultivated endothelial cells. Eur. J. Vasc. Surg. 1993; 7:402-8.
42. Köveker G B, Graham L M, Burkel W E, et al. Extracellular matrix preparation of expanded polytetrafluoroethylene grafts seeded with endothelial cells: influence on early platelet deposition, cellular growth, and luminal prostacyclin release. Surgery. 1991; 109:313-9.
43. Seeger J M, Klingman N. Improved endothelial cell seeding with cultured cells and fibronectin-coated grafts. J. Surg. Res. 1985; 38:641-7.
44. Seeger J M, Klingman N. Improved in vivo endothelialization of prosthetic grafts by surface modification with fibronectin. J. Vasc. Surg. 1988; 8:476-82.
45. Zilla P, Preiss P, Groscurth P, et al. In vitro-lined endothelium initial integrity and ultrastructural events. Surgery 1994; 116:524-34.
46. Zilla P, Deutsch M, Meinhart J. et al. Clinical in vitro endothelialization of femoropopliteal bypass grafts: an actuarial follow-up over three years. J. Vasc. Surg. 1994; 19:540-8.
47. Deutsch M, Meinhart J, Vesely M. In vitro endothelialization of expanded polytetrafluoroethylene grafts: a clinical case report after 41 months of implantation. J. Vasc. Surg. 1997; 25:757-63.
48. Deutsch M, Meinhart J, Fischlein T, Preiss P, Zilla P. Clinical autologous in vitro endothelialization of infrainguinal ePTFE grafts in 100 patients, a 9-year experience. Surgery. 1999; 126:847-55.
49. Hsu S, Tseng H, Wu M. Comparative In vitro evaluation of two different preparations of small diameter polyurethane vascular grafts. Artif. Organs. 2000:24:119-28.
50. Laube H R, Duwe J, Rutsch W, Konertz W. Clinical experience with autologous endothelial cell-seeded polytetrafluoroethylene coronary artery bypass grafts. J. Thorac. Cardiovasc. Surg. 2000; 120:134-41.
51. Magometschnigg H, Kadletz M, Vodrazka M, et al. Prospective clinical study with in vitro endothelial cell lining of expanded polytetrafluoroethylene grafts in crural repeat reconstruction. J. Vasc. Surg. 1992; 15:527-35.
52. Meinhart J G, Deutsch M, Fischlein T, et al. Clinical autologous in vitro endothelialization of 153 infrainguinal ePTFE grafts. Ann. Thorac. Surg. 2001; 71:S327-S33

53. Swedenborg J, Bengtsson L, Clyne N, et al. In vitro endothelialisation of arteriovenous loop grafts for haemodialysis. Eur. J. Vasc. Endovasc. Surg. 1997; 13:272-7.
54. Williams S K, Kleinert L B, Rose D, McKenney S. Origin of endothelial cells that line expanded polytetrafluorethylene vascular grafts sodded with cells from microvascularized fat. J. Vasc. Surg. 1994; 19:594-604.
55. Williams S K, Rose D G, Jarrell B E. Microvascular endothelial cell sodding of ePTFE vascular grafts: improved patency and stability of the cellular lining. J. Biomed. Mater. Res. 1994; 28:203-12.
56. Ahlswede K M, Williams S K. Microvascular endothelial cell sodding of 1-mm expanded polytetrafluoroethylene vascular grafts. Arterioscler. Thromb. 1994.14:25-31.
57. Wang Z G, Li G, Wu J, el al. Enhanced patency of venous Dacron grafts by endothelial cell sodding. Ann. Vasc. Surg. 1993; 7:429-36.
58. Williams S K, Carter T, Park P K, et al. Formation of a multilayer cellular lining on a polyurethane vascular graft following endothelial cell sodding. J. Biomed. Mater. Res. 1992; 26:103-17.
59. Williams S K, Schneider T, Kapelan B, Jarrell B E. Formation of a functional endothelium on vascular grafts. J. Electron. Microsc. Tech. 1991; 19:439-51.
60. Park P K, Jarrell B E, Williams S K, et al. Thrombus-free, human endothelial surface in the midregion of a Dacron vascular graft in the splanchnic venous circuit-observations after nine months of implantation. J. Vasc. Surg. 1990; 11:468-75.
61. Motwani M S, Rafiei Y, Tzifa A, Seifalian A M. In situ endothelialization of intravascular stents from progenitor stem cells coated with nanocomposite and functionalized biomolecules. Biotechnol. Appl. Biochem. 2011; 58:2-13.
62. Garipcanl B, Maenz S, Pham T. Image Analysis of Endothelial Microstructure and Endothelial Cell Dimensions of Human Arteries—A Preliminary Study. Adv. Eng. Mater. 2011; 13:B54-B57.
63. Yazdani S K, Kolodgie E D, Virmani R. Ex vivo and preclinical assessment of an endothelial progenitor cell capturing bioengineered stent. Minerva Cardioangiol. 2012; 60:11-21.
64. Silber S, Damman P, Klomp M, et al. Clinical results after coronary stenting with the Genous™ Bio-engineered R stent™: 12-month outcomes of the e-HEALING (Healthy Endothelial Accelerated Lining Inhibits Neointimal Growth) worldwide registry. EuroIntervention. 2011; 6:819-25.
65. Barbato E, Wijns W. Autologous cell therapy for enhanced endovascular repair after coronary stent implantation. EuroIntervention. 2011; 6:794-797.
66. Lee Y B, Shin Y M, Lee J, et al. Polydopamine-mediated immobilization of multiple bioactive molecules for the development of functional vascular graft materials. Biomaterials. 2012.
67. Nystrom D, Malmstrom E, Hult A, et al. Biomimetic surface modification of honeycomb films via a "grafting from" approach. Langmuir. 2010; 26:12748-54.
68. von der Mark K, Park J, Bauer S, Schmuki P. Nanoscale engineering of biomimetic surfaces: cues from the extracellular matrix. Cell. Tissue Res. 2010; 339:131-53.
69. Wessely R. New drug-eluting stent concepts. Nat. Rev. Cardiol. 2010; 7:194-203.
70. Zelikin A N. Drug releasing polymer thin films: New era of surface-mediated drug delivery. ACS Nano. 2010; 4:2494-2509.
71. Lee H, Dellatore S M, Miller W M, Messersmith P B. Mussel-inspired surface chemistry for multifunctional coatings. Science. 2007; 318:426-30.
72. Lynge M E, van der Westen R, Postma A, Stadler B. Polydopamine—a nature-inspired polymer coating for biomedical science. Nanoscale. 2011; 3:4916-28.
73. Lee J H, Lee H B, Andrade J D. Blood compatibility of polyethylene oxide surfaces. Prog. Polym. Sci. 1995; 20:1043-79.
74. Han D K, Park K D, Ryu G H, et al. Plasma protein adsorption to sulfonated poly(ethylene oxide)-grafted polyurethane surface. J. Biomed. Mater. Res. 1996:30:23-30.
75. Han D K, Jeong S Y, Kim Y H, Min B G, Cho H I. Negative cilia concept for thromboresistance: Synergistic effect of PEO and sulfonate groups grafted onto polyurethanes. J. Biomed. Mater. Res. 1991; 25:561-75.
76. Zhang F, Kang E T, Neoh K G, Huang W. Modification of gold surface by grafting of poly(ethylene glycol) for reduction in protein adsorption and platelet adhesion. J. Biomater. Sci. Polym. Edn. 2001; 12:515-31.
77. Han D K, Hubbell J A. Synthesis of polymer network scaffolds from l-lactide and poly(ethylene glycol) and their interaction with cells. Macromolecules. 1997; 30:6077-83.
78. Chen Y J, Kang E T, Neoh K G, Wang P, Tan K L. Surface modification of polyaniline film by grafting of poly(ethylene glycol) for reduction in protein adsorption and platelet adhesion. Synth. Met. 2000; 110:47-55.
79. Zhang F, Kang E T, Neoh K G, Wang P, Tan K L. Surface modification of stainless steel by grafting of poly(ethylene glycol) for reduction in protein adsorption. Biomaterials. 2001; 22:1541-8.
80. Wang P, Tan K L, Kang E T. Surface modification of poly(tetrafluoroethylene) films via grafting of poly(ethylene glycol) for reduction in protein adsorption. J. Biomater. Sci. Polym. Ed. 2000; 11:169-86.
81. Zeng R, Luo Z, Zhou D, Cao F, Wang Y. A novel PEG coating immobilized onto capillary through polydopamine coating for separation of proteins in CE. Electrophoresis. 2010; 31:3334-41.
82. Proks V, Jaroš J, Pop-Georgievski O, et al. "Click & Seed" approach to the biomimetic modification of material surfaces. Macromol. Biosci. 2012; 12:1232-42.
83. Wilson D S, Nock S. Functional protein microarrays. Curr. Opin. Chem. Biol. 2001; 6:81-5.
84. Butler J E, Ni L, Nessler R, et al. The physical and functional behavior of capture antibodies adsorbed on polystyrene. J. Immunol. Methods. 1992; 150:77-90.
85. Ghani R, Iqbal A, Akhtar N, et al. Identification of different stages of hepatitis B infection with enzyme linked immunosorbant assay (ELISA) and polymerase chain reaction (PCR) assay. J. Med. Plants Res. 2011; 5:2572-76.
86. Li X, Conklin L, Alex P. New serological biomarkers of inflammatory bowel disease. World J. Gastroenterol. 2008; 14:5115-24.
87. Moelans C B, de Weger R A, Van der Wall E, van Diest P J. Current technologies for HER2 testing in breast cancer. Crit. Rev. Oncol. Hematol. 2011:80:380-92.
88. Niitsu T. Associations of serum brain-derived neurotrophic factor with cognitive impairments and negative symptoms in schizophrenia. Prog. Neuropsychopharmacol. Biol. Psychiatry. 2011; 35:1836-40.
89. Shephard G S. Determination of mycotoxins in human foods. Chem. Soc. Rev. 2008; 37:2468-77.

90. Xiong Q, Ge F. Identification and evaluation of a panel of serum biomarkers for predicting response to thalidomide in multiple myeloma patients. Expert Rev. Proteomics. 2011; 8:439-42.
91. Yotsumoto H. Specific immune-based diagnosis of tuberculosis infection. Rinsho Byori. 2008; 56:1026-33.
92. Kausaite-Minkstimiene A, Ramanaviciene A, Kirlyte J, Ramanavicius A. Comparative study of random and oriented antibody immobilization techniques on the binding capacity of immunosensor. Anal. Chem. 2010; 82:6401-08.
93. Butler J E, Ni L, Brown W R, et al. The immunochemistry of sandwich ELISAs: VI. Greater than 90% of monoclonal and 75% of polyclonal anti-fluorescyl capture antibodies (CAbs) are denatured by passive adsorption. Mol. Immunol. 1993; 30:1165-75.
94. Butler J E, Ni L, Nessler R, et al. The physical and functional-behavior of capture antibodies adsorbed on polystyrene. J. Immunol. Methods. 1992; 150:77-90.
95. Rotmans J I, Heyligers J M, Verhagen H J, et al. In vivo cell seeding with anti-CD34 antibodies successfully accelerates endothelialization but stimulates intimal hyperplasia in porcine arteriovenous expanded polytetrafluoroethylene grafts. Circulation. 2005; 112:12-8.
96. Mrówczyński W, Rungatscher A, Buchegger F, Tille J-C, Namy S, Ratib O, Kutryk M, Walpoth B H. Biological effects of anti-CD34-coated ePTFE vascular graft. Early in vivo experimental results. Kardiochirurgia i Torakochirurgia Polska 2014; 11:182-90.
97. Patel N, Davies M, Hartshorne M, et al. Immobilization of protein molecules onto homogeneous and mixed carboxylate-terminated self-assembled monolayers. Langmuir. 1997; 13:6485-90.
98. MacBeath G, Schreiber S. Printing proteins as microarrays for high-throughput function determination. Science. 2000; 289:1760-63.
99. Faye C, Chamieh J, Moreau T, et al. In situ characterization of antibody grafting on porous monolithic supports. Anal. Biochem. 2012; 420:147-54.
100. Lin Q, Ding X, Qiu F, et al. In situ endothelialization of intravascular stents coated with an anti-CD34 antibody functionalized heparin-collagen multilayer. Biomaterials. 2010; 31:4017-25.
101. Johnsson B, Löfås S, Lindquist G, et al. Comparison of methods for immobilization to carboxymethyl dextran sensor surfaces by analysis of the specific activity of monoclonal antibodies. J. Mol. Recognit. 1995; 8:125-31.
102. Lin J N, Chang I N, Andrade J D, Herron J N, Christensen D A. Comparison of site-specific coupling chemistry for antibody immobilization on different solid supports. J. Chromatogr. 1991; 542:41-54.
103. O'Shannessy D J, Hoffman W L. Site-directed immobilization of glycoproteins on hydrazide-containing solid supports. Biotechnol. Appl. Biochem. 1987; 9:488-96.
104. Hoffman W L, O'Shannessy D J. Site-specific immobilization of antibodies by their oligosaccharide moieties to new hydrazide derivatized solid supports. J. Immunol. Methods. 1988; 112:113-20.
105. Turková J. Oriented immobilization of biologically active proteins as a tool for revealing protein interactions and function. J. Chromatogr. B. 1999; 722:11-31.
106. Wimalasena R L, Wilson G S. Factors affecting the specific activity of immobilized antibodies and their biologically active fragments. J. Chromatogr. 1991; 572:85-102.
107. Yuan Y, Yin M. Qian J, Liu C. Site-directed immobilization of antibodies onto blood contacting grafts for enhanced endothelial cell adhesion and proliferation. Soft Matter. 2011; 7:7207-16.
108. Kang J H, Choi H J, Hwang S Y. Improving immunobinding using oriented immobilization o fan oxidized antibody. J. Chromatogr. A. 2007; 1161:9-14.
109. Boeggeman E, Ramakrishnan B, Pasek M, et al. Site specific conjugation of fluoroprobes to the remodeled Fc N-glycans of monoclonal antibodies using mutant glycosyltransferases: application for cell surface antigen detection. Bioconjug. Chem. 2009; 20:1228-36.
110. Zeglis B M, Davis C B, Aggeler R, et al. Enzyme-Mediated Methodology for the Site-Specific Radiolabeling of Antibodies Based on Catalyst-Free Click Chemistry. Bioconjug. Chem. 2013; 24:1057-67.
111. Yang W J, Cai T, Neoh K G, et al. Biomimetic anchors for antifouling and antibacterial polymer brushes on stainless steel. Langmuir. 2011; 27:7065-76.
112. Wei Q, Li B, Yi N, et al. Improving the blood compatibility of material surfaces via biomolecule-immobilized mussel-inspired coatings. J. Biomed. Mater. Res. A. 2011; 96:38-45.
113. Zeng R, Luo Z, Zhou D, Cao F, Wang Y. A novel PEG coating immobilized onto capillary through polydopamine coating for separation of proteins in CE. Electrophoresis. 2010; 31:3334-41.
114. "Biological Evaluation of Medical Devices," ISO 10993, parts 1-12. (Geneva: International Organization for Standardization, various dates).
115. "Use of International Standard ISO 10993, Biological Evaluation of Medical Devices-Part 1: Evaluation and Testing" G95-1 (Rockville, Md.: Department of Health and Human Services, FDA, 1995).
116. "Testing Methods to Evaluate Biological Safety of Medical Devices, Notice from the Office Medical Devices Evaluation Number 36" (Pharamaceutical and Food Safety Bureau, Ministry of Health, Labour and Welfare, Mar. 19, 2003).
117. "A Practical Guide to ISO 10993," parts 1-12, Medical Device & Diagnostic Industry 20, no. 1, 2, 4-12, and 21, no. 1 (January 1998-January 1999).
118. Food and Drug Administration 2005. Guidelines for industry and FDA staff, non-clinical tests and recommended labeling for intravasular stents and associated delivery systems. http://www.fda.gov/cdrh/ode/guidance/1545.pdf
119. Pache J, Kastrati A, Mehilli J. Intracoronary stenting and angiographic results, strut thickness effect on restenosis outcome (ISAR-STEREO-2) trial. J. Am. Coll. Cardiol. 2003; 41:1283-8.
120. Horny P, Turgeon S, Hale P, Lewis F, Mantovi D. PEEM/NEXAFS analysis of ultrathin fluorocarbon films for coated stents. Canadian Light Source 2007 Annual Report. http://www.lightsource.ca/about/pdf/activity_report_2007/all_inclusive_web.pdf
121. Savage P, O'Donnell B P, McHugh P E, Murphy B P, Quinn D F. Coronary stent strut size dependent stress-strain response investigated using micromechanical finite element models. Ann. Biomed. Eng. 2004; 32:202-11.
122. Chua S N D, MacDonald B J, Hashmi M S J. Finite element simulation of stent and balloon interaction. J. Mater. Process. Technol. 2003; 143-144:591-7.
123. Dumoulin C, Cochelin B. Mechanical behaviour modelling of balloon-expandable stents. J. Biomech. 2000; 33:1461-70.

124. Etave F, Finet G, Boivin M, Boyer J-C, Rioufol G, Thollet G. Mechanical properties of coronary stents determined by using finite element analysis. J. Biomech. 2001; 34:1065-75.

125. Migliavacca F, Petrini L, Colombo M, Auricchio F, Pietrabissa R. Mechanical behavior of coronary stents investigated through the finite element method. J. Biomech. 2002; 35:803-11.

126. Migliavacca F, Petrini L, Montanari V, Quagliana I, Auricchio F and Dubini G. A predictive study of the mechanical behaviour of coronary stents by computer modelling. Med. Eng. Phys. 2005; 27:13-8.

127. Luo R, Tang L, Zhong S, Yang Z, Wang J, Weng Y, Tu Q, Jiang C, Huang N. In vitro investigation of enhanced hemocompatibility and endothelial cell proliferation associated with quinone-rich polydopamine coating. ACS Appl. Mater. Interfaces. 2013; 5:1704-14.

128. Lewis F, Maheux-Lacroix B, Turgeon S, Mantovani D. Adhesion assessment of ultra-thin plasma-polymerized coatings on stainless-steel stents using the small-punch test. In: Mittal K L, ed. Adhesion aspects of thin films Boston: VSP, 2007. p. 71-83.

129. Lewis F, Horny P, Halel P, Turgeon S, Tatoulian M, Mantovani D. Study of the adhesion of thin plasma fluorocarbon coatings resisting plastic deformation for stent applications. J. Phys. D. Appl. Phys. 41 045310, doi:10.1088/0022-3727/41/4/045310.

130. Owens D K, Wendt R C. Estimation of the surface free energy of polymers. J. Appl. Polym. Sci. 1969; 13:1741-7.

131. Li X, Tian X, Zhang J, et al. In vitro and in vivo evaluation of folate receptor-targeting amphiphilic copolymer-modified liposomes loaded with docetaxel. Int. J. Nanomedicine. 2011; 6:1167-84.

132. Strother T, Hamers R J, Smith L M. Covalent attachment of oligodeoxyribonucleotides to amine-modified Si (001) surfaces. Nucleic Acids Res. 2000; 28:3535-41.

133. Muscari C, Gamberini C, Basile I et al. Comparison between culture conditions improving growth and differentiation of blood and bone marrow cells committed to the endothelial cell lineage. Biol. Proceed. Online. 2010; 12:89-106.

134. Molloi S, Ersahin A, Tang J, et al. Quantification of volumetric coronary blood flow with dual-energy digital subtraction angiography. Circulation. 1996; 93:1919-27.

135. Thoma R. Untersuchungen uber die histogenese und histomechanick des gefassystems. Stuttgart, Germany: Enke; 1893.

136. Armstrong M L, Heistad D D, Marcus M L, Megan M B, Piegors D J. Structural and hemodynamic response of peripheral arteries of macaque monkeys to atherogenic diet. Arteriosclerosis. 1985; 5:336-46.

137. Glagov S, Weisenberg E, Zarins C K, Stankunavicius R, Kolettis G J. Compensatory enlargement of human atherosclerotic coronary arteries. N. Engl. J. Med. 1987; 316:1371-5.

138. Hermiller J B, Tenaglia A N, Kisslo K B. et al. In vivo validation of compensatory enlargement of atherosclerotic coronary arteries. Am. J. Cardiol. 1993; 71:665-8.

139. Alfonso F, Macaya C, Goicolea J, et al. Intravascular ultrasound imaging of angiographically normal coronary segments in patients with coronary artery disease. Am. Heart J. 1994,127:536-44.

140. Pasterkamp G, Wensing P J, Post M J, et al. Paradoxical arterial wall shrinkage may contribute to luminal narrowing of human atherosclerotic femoral arteries. Circulation. 1995; 91:1444-9.

141. Smits P C, Pasterkamp G, Quarles van Ufford M A, et al. Coronary artery disease: arterial remodelling and clinical presentation. Heart. 1999; 82:461-4.

142. von Birgelen C, Klinkhart W, Mintz G S, et al. Plaque distribution and vascular remodeling of ruptured and nonruptured coronary plaques in the same vessel: an intravascular ultrasound study in vivo. J. Am. Coll. Cardiol. 2001; 37:1864-70.

143. Pasterkamp G, Schoneveld A H, van Wolferen W, et al. The impact of atherosclerotic arterial remodeling on percentage of luminal stenosis varies widely within the arterial system. A postmortem study. Arterioscler. Thromb. Vasc. Biol. 1997; 17:3057-63.

144. Langille B L. Arterial remodeling: relation to hemodynamics. Can. J. Physiol. Pharmacol. 1996; 74:834-41.

145. Kramsch D M, Aspen A J, Abramowitz B M, Kreimendahl T, Hood W B Jr. Reduction of coronary atherosclerosis by moderate conditioning exercise in monkeys on an atherogenic diet. N. Engl. J. Med. 1981; 305:1483-9.

146. Tronc F, Wassef M, Esposito B. et al. Role of NO in flow-induced remodeling of the rabbit common carotid artery. Arterioscler. Thromb. Vasc. Biol. 1996; 16:1256-62.

147. Abbruzzese T A, Guzman R J, Martin R L, et al. Matrix metalloproteinase inhibition limits arterial enlargements in a rodent arteriovenous fistula model. Surgery. 1998; 124:328-34.

148. Lehoux S, Tedgui A. Signal transduction of mechanical stresses in the vascular wall. Hypertension. 1998; 32:338-45.

149. Di Stefano I, Koopmans D R, Langille B L. Modulation of arterial growth of the rabbit carotid artery associated with experimental elevation of blood flow. J. Vasc. Res. 1998; 35:1-7.

150. Kornowski R, Mintz G S, Lansky A J, et al. Paradoxic decreases in atherosclerotic plaque mass in insulin-treated diabetic patients. Am. J. Cardiol. 1998; 81:1298-304.

151. Tauth J, Pinnow E, Sullebarger J T, et al. Predictors of coronary arterial remodeling patterns in patients with myocardial ischemia. Am. J. Cardiol. 1997; 80:1352-1355.

152. Lim T T, Liang D H, Botas J, et al. Role of compensatory enlargement and shrinkage in transplant coronary artery disease: Serial intravascular ultrasound study. Circulation. 1997; 95:885-859.

153. Vane J R, Anggard E E, Botting R M. Regulatory functions of the vascular endothelium. N. Engl. J. Med. 1990; 323:27-36.

154. Vane J R, Botting R M. Pharmacodynamic profile of prostacyclin. Am. J. Cardiol. 1995; 75:3A-10A.

155. Negishi M, Sugimoto Y, Ichikawa A. Molecular mechanisms of diverse actions of prostanoid receptors. Biochim. Biophys. Acta. 1995; 1259:109-19.

156. Forman B M, Chen J, Evans R M. Hypolipidemic drugs, polyunsaturated fatty acids, and eicosanoids are ligands for peroxisome proliferator-activated receptors alpha and delta. Proc. Natl. Acad. Sci. USA. 1997; 94:4312-7.

157. Gupta R A, Tan J, Krause W F, et al. Prostacyclin-mediated activation of peroxisome proliferator-activated receptor delta in colorectal cancer. Proc. Natl. Acad. Sci. USA. 2000; 97:13275-80.

158. Hatae T, Wada M, Yokoyama C, Shimonishi M, Tanabe T. Prostacyclin-dependent apoptosis mediated by PPAR delta. J. Biol. Chem. 2001; 276:46260-7.

159. Moncada S, Vane J R. Pharmacology and endogenous roles of prostaglandin endoperoxides, thromboxane A2, and prostacyclin. Pharmacol. Rev. 1978; 30:293-331.
160. Vane J, Corin R E. Prostacyclin: a vascular mediator. Eur. J. Vasc. Endovasc. Surg. 2003; 26:571-8.
161. Geraci M, Gao B, Shepherd D, et al. Pulmonary prostacyclin synthase overexpression by adenovirus transfection and in transgenic mice. Chest. 1998:114:99S.
162. Nagaya N, Yokoyama C, Kyotani S, et al. Gene transfer of human prostacyclin synthase ameliorates monocrotaline-induced pulmonary hypertension in rats. Circulation. 2000; 102:2005-10.
163. Suhara H, Sawa Y, Fukushima N, et al. Gene transfer of human prostacyclin synthase into the liver is effective for the treatment of pulmonary hypertension in rats. J. Thorac. Cardiovasc. Surg. 2002; 123:855-61.
164. Todaka T, Yokoyama C, Yanamoto H, et al. Gene transfer of human prostacyclin synthase prevents neointimal formation after carotid balloon injury in rats. Stroke. 1999; 30:419-26.
165. Yamada M, Numaguchi Y, Okumura K, et al. Prostacyclin synthase gene transfer modulates cyclooxygenase-2-derived prostanoid synthesis and inhibits neointimal formation in rat balloon-injured arteries. Arterioscler. Thromb. Vasc. Biol. 2002; 22:256-62.
166. Numaguchi Y, Okumura K, Harada M, et al. Catheter-based prostacyclin synthase gene transfer prevents in-stent restenosis in rabbit atheromatous arteries. Cardiovasc. Res. 2004; 61:177-185
167. Bell D, McDermott B J. Calcitonin gene-related peptide in the cardiovascular system: characterization of receptor populations and their (patho)physiological significance. Pharmacol. Rev. 1996; 48:253-88.
168. Brain S D, Cambridge H. Calcitonin gene-related peptide: vasoactive effects and potential therapeutic role. Gen. Pharmacol. 1996; 27:607-11.
169. Marshall I. Mechanism of vascular relaxation by the calcitonin gene-related peptide. Ann. NY Acad. Sci. 1992; 657:204-15.
170. Yoshimoto R, Mitsui-Saito M, Ozaki H, Karaki H. Effects of adrenomedullin and calcitonin gene-related peptide on contractions of the rat aorta and porcine coronary artery. Br. J. Pharmacol. 1998; 123:1645-54.
171. Vega A V, Avila G. CGRP, a vasodilator neuropeptide that stimulates neuromuscular transmission and EC coupling. Curr. Vasc. Pharacol. 2010; 8:394-403.
172. Hirata Y, Takagi Y, Takata S, et al. Calcitonin gene-related peptide receptor in cultured vascular smooth muscle and endothelial cells. Biochem. Biophys. Res. Commun. 1988; 151:1113-21.
173. Wellman G C, Quayle J M, Standen N B. ATP-sensitive K+ channel activation by calcitonin gene-related peptide and protein kinase A in pig coronary arterial smooth muscle. J. Physiol. 1998; 507:117-29.
174. Gray D W, Marshall I. Human alpha-calcitonin gene-related peptide stimulates adenylate cyclase and guanylate cyclase and relaxes rat thoracic aorta by releasing nitric oxide. Br. J. Pharmacol. 1992; 107:691-6.
175. Franco-Cereceda A. Calcitonin gene-related peptide and tachykinins in relation to local sensory control of cardiac contractility and coronary vascular tone. Acta. Physiol. Scand. Suppl. 1988; 569:1-63
176. Gulbenkian S, Saetrum Opgaard O, Ekman R, et al. Peptidergic innervation of human epicardial coronary arteries. Circ. Res. 1993; 73:579-88.
177. Uren N G, Seydoux C. Davies G J. Effect of intravenous calcitonin gene related peptide on ischaemia threshold and coronary stenosis severity in humans. Cardiovasc. Res. 1993; 27:1477-81.
178. Ward M R, Thompson K A, Isaac K, Vecchiarelli J, Zhang Q, Stewart D J, Kutryk M J. Nitric oxide synthase gene transfer restores activity of circulating angiogenic cells from patients with coronary artery disease. Mol. Ther. 2011; 19:1323-1330.
179. Dallos A, Kiss M, Polyanka H, et al. Effects of the neuropeptides substance P, calcitonin gene-related peptide, vasoactive intestinal polypeptide and galanin on the production of nerve growth factor and inflammatory cytokines in cultured human keratinocytes. Neuropeptides. 2006; 40:251-63.
180. Chou T M, Sudhir K, Iwanaga S, Chatterjee K, Yock P G. Measurement of volumetric coronary blood flow by simultaneous intravascular two-dimensional and Doppler ultrasound: validation in an animal model. Am. Heart J. 1994; 128:237-43.
181. Kornowski R, Hong M K, Tio F O, et al. In-stent restenosis: contributions of inflammatory responses and arterial injury to neointimal hyperplasia. J. Am. Coll. Cardiol. 1998; 31:224-30.
182. Franco E J, Hofstetter H, Hofstetter O. A comparative evaluation of random and site-specific immobilization techniques for the preparation of antibody-based chiral stationary phases. J. Sep. Sci. 2006; 29:1458-69.
183. Alves N J, Kiziltepe T, Bilgicer B. Oriented surface immobilization of antibodies at the conserved nucleotide binding site for enhanced antigen detection. Laugmuir. 2012; 28:9640-8.
184. Giaretta I, Madeo D, Bonagur R, et al. A comparative evaluation of gene transfer into blood cells using the same retroviral backbone for independent expression of the EGFP and ΔLNGFR marker genes. Haematologica. 2000; 85:680-9.
185. Perin E C, Tian M, Marini F C III, et al. Imaging long-term fate of intramyocardially implanted mesenchymal stem cells in a porcine myocardial infarction model. PLoS ONE. 2011; 6:e22949.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A medical device having a coating, wherein the medical device is an artificial heart valve, a vascular stent graft or a synthetic graft, wherein the coating comprises (i) polydopamine, (ii) a polyether derivative, and (iii) antibodies, wherein the polydopamine is coated on the medical device and is covalently linked to the polyether derivative, and the polyether derivative is covalently linked to an Fc region of the antibodies, wherein the polyether derivative has an average molecular weight ranging from 200 Daltons to 1,000 Daltons, the antibodies specifically bind to a cell surface antigen of endothelial progenitor cells or endothelial cells, and wherein the cell surface antigen is CD34.

2. The medical device of claim 1, wherein the polyether derivative is polyethylene glycol (PEG), a polyethylene glycol (PEG) derivative, polypropylene glycol (PPG), a polypropylene glycol (PPG) derivative, or combinations thereof.

3. The medical device of claim 2, wherein the polyether derivative is PEG.

4. The medical device of claim 1, wherein the polyether derivative has an average molecular weight ranging from 200 Daltons to 350 Daltons.

5. The medical device of claim 1, further comprising a biocompatible polymer selected from the group consisting of polytetrafluoroethylene (PTFE), expanded PTFE (ePTFE), polyethylene terephthalate, polyethylene, polyurethane, polypropylene, combinations thereof, and derivatives thereof.

6. The medical device of claim 1, wherein the coating further comprises a pharmaceutical substance.

7. The medical device of claim 6, wherein the pharmaceutical substance inhibits smooth muscle cell migration and/or proliferation.

8. The medical device of claim 6, wherein the pharmaceutical substance is paclitaxel, rapamycin, a rapamycin derivative, sirolimus, everolimus, tacrolimus, biolimus, biolimus A-9, or combinations thereof.

9. A medical device having a coating, wherein the medical device is an artificial heart valve, a vascular stent graft or a synthetic graft, wherein the coating comprises (i) polydopamine, (ii) a polyether derivative, and (iii) antibodies, wherein the polydopamine is coated on the medical device and is covalently linked to the polyether derivative, and the polyether derivative is covalently linked to an amine group on a modified polyethylene glycol linker to the Fc region of the antibodies through an oxidized polysaccharide, the polyether derivative has an average molecular weight ranging from 200 Daltons to 1,000 Daltons, the antibodies specifically bind to a cell surface antigen of endothelial progenitor cells or endothelial cells, and wherein the cell surface antigen is CD34.

* * * * *